United States Patent
Finlay et al.

(10) Patent No.: US 10,294,221 B2
(45) Date of Patent: *May 21, 2019

(54) 1, 3, 4-THIADIAZOLE COMPOUNDS AND THEIR USE IN TREATING CANCER

(71) Applicants: AstraZeneca AB, Sodertalje (SE); Cancer Research Technology Limited, London (GB)

(72) Inventors: Maurice Raymond Verschoyle Finlay, Cambridge (GB); Chukuemeka Tennyson Ekwuru, Cambridge (GB); Mark David Charles, Cambridge (GB); Piotr Antoni Raubo, Cambridge (GB); Jonathan James Gordon Winter, Cambridge (GB); Johannes Wilhelmus Maria Nissink, Cambridge (GB)

(73) Assignees: AstraZeneca AB, Sodertalje (SE); Cancer Research Technology Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/025,455

(22) Filed: Jul. 2, 2018

(65) Prior Publication Data
US 2018/0305349 A1    Oct. 25, 2018

Related U.S. Application Data

(63) Continuation of application No. 15/314,562, filed as application No. PCT/GB2015/051537 on May 27, 2015, now Pat. No. 10,040,788.

(30) Foreign Application Priority Data

May 30, 2014    (GB) .................... 1409624.2

(51) Int. Cl.
C07D 417/14    (2006.01)
C07B 59/00    (2006.01)

(52) U.S. Cl.
CPC .......... *C07D 417/14* (2013.01); *C07B 59/002* (2013.01); *C07B 2200/05* (2013.01); *C07B 2200/13* (2013.01)

(58) Field of Classification Search
None
See application file for complete search history.

(56) References Cited

U.S. PATENT DOCUMENTS

2014/0142081 A1    5/2014    Lemieux et al.

FOREIGN PATENT DOCUMENTS

| WO | WO 2012/170664 A2 | 12/2012 |
|---|---|---|
| WO | WO 2013/078123 A1 | 5/2013 |
| WO | WO 2014/078645 A1 | 5/2014 |
| WO | WO 2014/079011 A1 | 5/2014 |
| WO | WO 2014/079136 A1 | 5/2014 |
| WO | WO 2014/079150 A1 | 5/2014 |
| WO | WO 2014/081925 A1 | 5/2014 |
| WO | WO 2014/089048 A1 | 6/2014 |

OTHER PUBLICATIONS

Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Chen et al. Targeting Glutamine Induces Apoptosis: A Cancer Therapy Approach. International Journal of Molecular Sciences, 2015, 16, 22830-22855.*
Thomas, Ajit G. et al., "Small molecule glutaminase inhibitors block glutamate release from stimulated microglia", Biochemical and Biophysical Research Communications, vol. 443, No. 1, Jan. 1, 2014, pp. 32-36.
Gross, Matthew I. et al., "Antitumor Activity of the Glutaminase Inhibitor CB-839 in Triple-Negative Breast Cancer", Molecuar Cancer Therapeutics, Feb. 12, 2014, pp. 890-901.

* cited by examiner

*Primary Examiner* — Po-Chih Chen

(57) ABSTRACT

The specification relates to compounds of Formula (I):

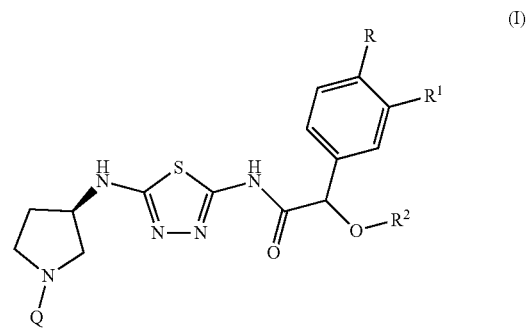

and pharmaceutically acceptable salts thereof, where Q, R, $R^1$ and $R^2$ have any of the meanings defined herein. The specification also relates to the use of such compounds and salts thereof to treat or prevent GLS1 mediated disease, including cancer. The specification further relates to crystalline forms of compounds of Formula (I) and pharmaceutically acceptable salts thereof; pharmaceutical compositions comprising such compounds and salts; kits comprising such compounds and salts; methods of manufacture of such compounds and salts; intermediates useful in the manufacture of such compounds and salts; and to methods of treating GLS1 kinase mediated disease, including cancer, using such compounds and salts.

11 Claims, 3 Drawing Sheets

Figure 1: X-Ray Powder Diffraction Pattern of Form D of (2S)-2-methoxy-2-phenyl-N-[5-[[(3R)-1-pyridazin-3-ylpyrrolidin-3-yl]amino]-1,3,4-thiadiazol-2-yl]acetamide
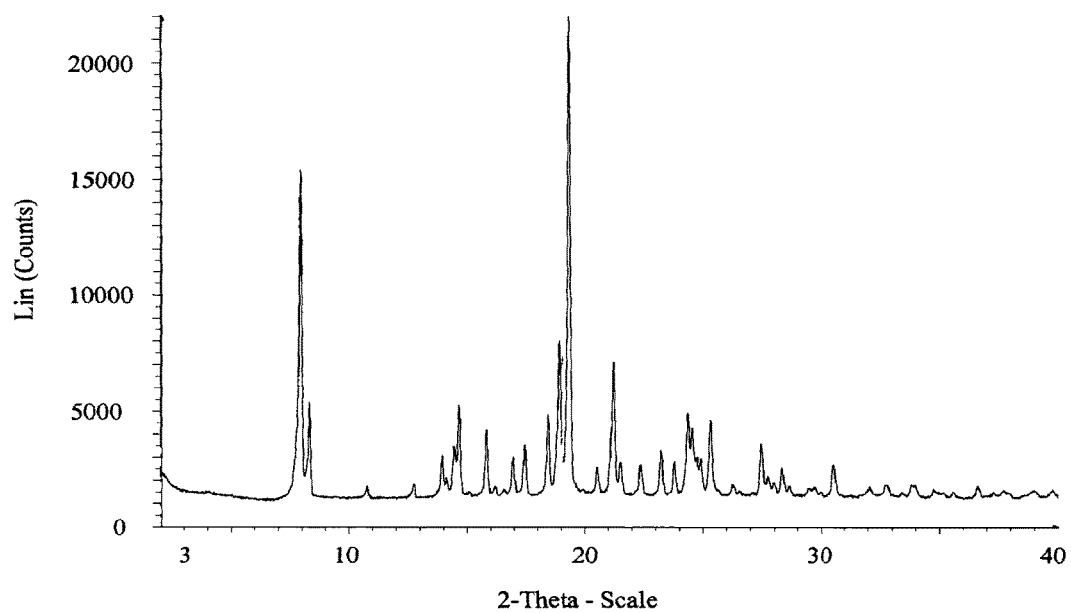

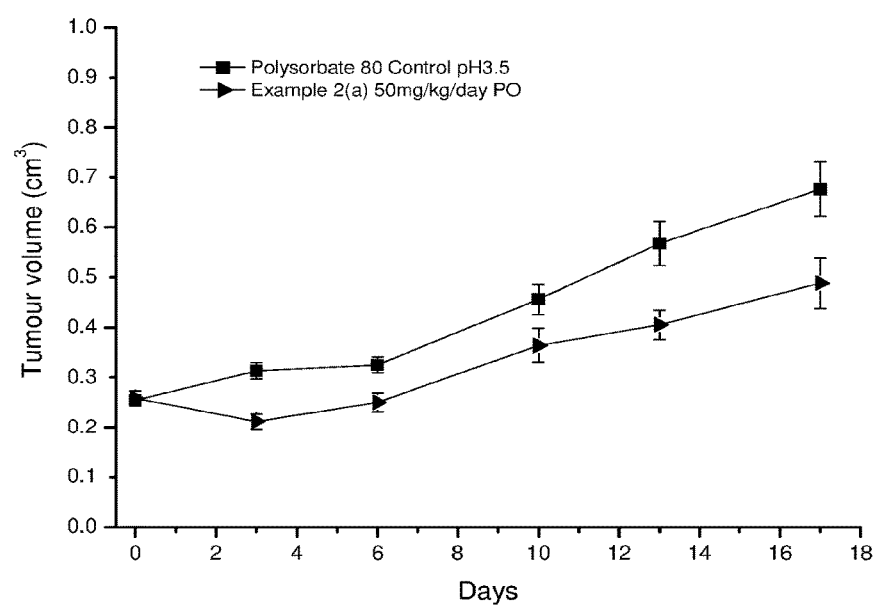
Figure 2: Tumour Growth Inhibition in the Mouse Xenograft Model by (2S)-2-Methoxy-2-phenyl-N-[5-[[(3R)-1-pyridazin-3-ylpyrrolidin-3-yl]amino]-1,3,4-thiadiazol-2-yl]acetamide

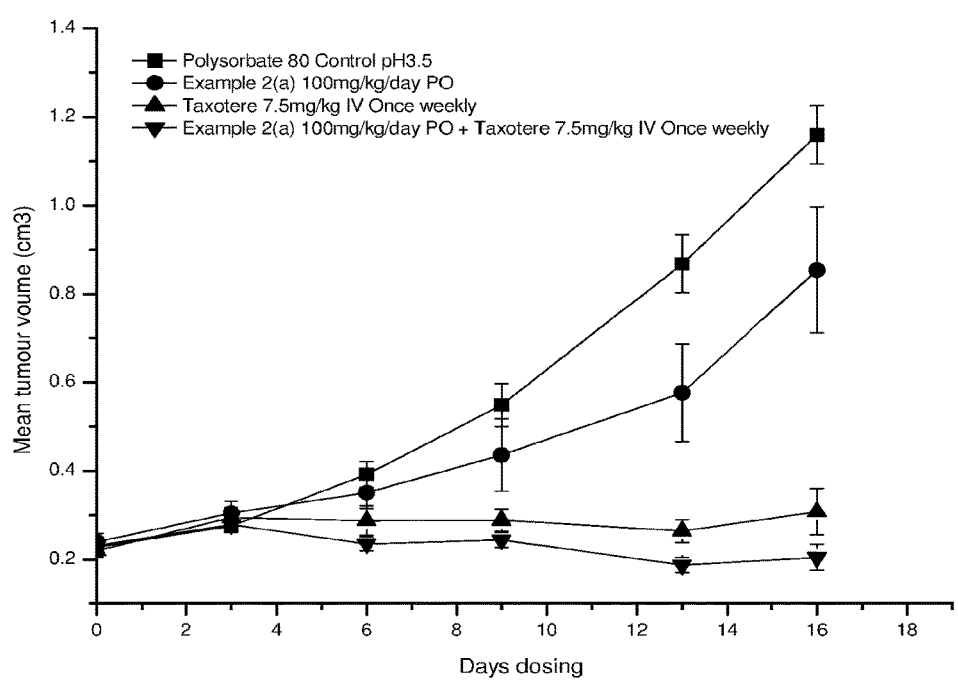
Figure 3: Tumour Growth Inhibition in the Mouse Xenograft Model by (2S)-2-Methoxy-2-phenyl-N-[5-[[(3R)-1-pyridazin-3-ylpyrrolidin-3-yl]amino]-1,3,4-thiadiazol-2-yl]acetamide in Combination with Taxotere®

1,3,4-THIADIAZOLE COMPOUNDS AND THEIR USE IN TREATING CANCER

This application is a Continuation of U.S. application Ser. No. 15/314,562 filed Nov. 29, 2016 which is the US National Stage under 35 U.S.C § 371 of International Application No. PCT/GB2015/051537 (filed 27 May 2015) which claims priority under 35 U.S.C. § 119(a)-(d) to GB Application No. 1409624.2 filed on 30 May 2014.

FIELD OF INVENTION

The specification generally relates to substituted 1,3,4-thiadiazole compounds and pharmaceutically acceptable salts thereof. These compounds act on the glutaminase 1 enzyme ("GLS1"), and the specification therefore also relates to the use of such compounds and salts thereof to treat or prevent GLS1 mediated disease, including cancer. The specification further relates to crystalline forms of compounds of substituted 1,3,4-thiadiazole compounds and pharmaceutically acceptable salts thereof; pharmaceutical compositions comprising such compounds and salts; kits comprising such compounds and salts; methods of manufacture of such compounds and salts; intermediates useful in the manufacture of such compounds and salts; and to methods of treating GLS1 kinase mediated disease, including cancer, using such compounds and salts.

BACKGROUND

Glutamine is the most abundant plasma amino acid and is involved in many growth promoting pathways. In particular, glutamine is involved in oxidation in the TCA cycle and in maintaining cell redox equilibrium, and also provides nitrogen for nucleotide and amino acid synthesis (Curi et al., *Front. Biosc.* 2007, 12, 344-57; DeBardinis and Cheng, *Oncogene* 2009, 313-324). Many cancer cells rely on glutamine metabolism as a consequence of metabolic changes in the cell, including the Warburg effect where glycolytic pyruvate is converted to lactic acid rather than being used to create Acetyl CoA (Koppenol et al., *Nature Reviews* 2011, 11, 325-337). As a consequence of this reliance on glutamine metabolism, such cancer cells are sensitive to changes in exogenous glutamine levels. Furthermore, there is much evidence to suggest that glutaminolysis plays a key role in certain cancer types (Hensley et al., *J. Clin. Invest.* 2013, 123, 3678-3684), and is associated with known oncogenic drivers such as Myc (Dang, *Cancer Res.* 2010, 70, 859-863).

The first step of glutamine catabolism to glutamate is catalysed by glutaminase, which exists as 2 isoforms GLS1 and GLS2, originally identified as being expressed in the Kidney and Liver respectively. Kidney glutaminase (GLS1) is known to be more ubiquitously expressed than Liver glutaminase (GLS2), and has 2 splice variants, KGA and the shorter GAC isoform, both of which are located in the mitochondria. (Elgadi et al., *Physiol. Genomics* 1999, 1, 51-62; Cassago et al., *Proc. Natl. Acad. Sci.* 2012, 109, 1092-1097). GLS1 expression is associated with tumour growth and malignancy in a number of disease types (Wang et al., *Cancer Cell* 2010, 18, 207-219; van der Heuval et al., *Cancer Bio. Ther.* 2012, 13, 1185-1194). Inhibitors of GLS1 are therefore expected to be useful in the treatment of cancer, as monotherapy or in combination with other anti-cancer agents.

SUMMARY OF INVENTION

Briefly, this specification describes, in part, a compound of Formula (I):

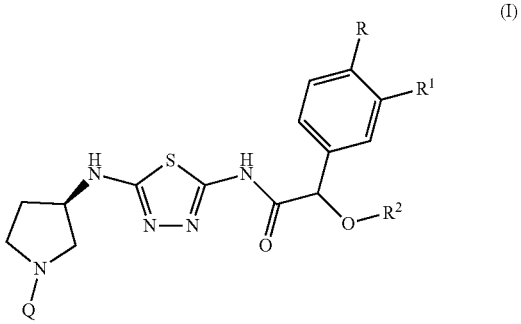

or a pharmaceutically acceptable salt thereof, where:
Q is pyridazin-3-yl, 1,2,4-triazin-3-yl or 1,2,4-triazin-6-yl;
R is hydro, fluoro or methoxy;
$R^1$ is hydro, methoxy, difluoromethoxy or trifluoromethoxy; and
$R^2$ is methyl or ethyl.

This specification also describes, in part, a pharmaceutical composition which comprises a compound of Formula (I), or a pharmaceutically acceptable salt thereof, and at least one pharmaceutically acceptable diluent or carrier.

This specification also describes, in part, a compound of Formula (I), or a pharmaceutically acceptable salt thereof, for use in therapy.

This specification also describes, in part, a compound of Formula (I), or a pharmaceutically acceptable salt thereof, for use in the treatment of cancer.

This specification also describes, in part, the use of a compound of Formula (I), or a pharmaceutically acceptable salt thereof, for the manufacture of a medicament for the treatment of cancer.

This specification also describes, in part, a method for treating cancer in a warm blooded animal in need of such treatment, which comprises administering to said warm-blooded animal a therapeutically effective amount of a compound of Formula (I), or a pharmaceutically acceptable salt thereof.

BRIEF DESCRIPTION OF THE FIGURES

FIG. 1: X-Ray Powder Diffraction Pattern of Form D of (2S)-2-Methoxy-2-phenyl-N-[5-[[(3R)-1-pyridazin-3-ylpyrrolidin-3-yl]amino]-1,3,4-thiadiazol-2-yl]acetamide.

FIG. 2: Tumour Growth Inhibition in the Mouse Xenograft Model by (2S)-2-Methoxy-2-phenyl-N-[5-[[(3R)-1-pyridazin-3-ylpyrrolidin-3-yl]amino]-1,3,4-thiadiazol-2-yl]acetamide.

FIG. 3: Tumour Growth Inhibition in the Mouse Xenograft Model by (2S)-2-Methoxy-2-phenyl-N-[5-[[(3R)-1-pyridazin-3-ylpyrrolidin-3-yl]amino]-1,3,4-thiadiazol-2-yl]acetamide in Combination with Taxotere®.

DESCRIPTION OF ILLUSTRATIVE EMBODIMENTS

Many embodiments of the invention are detailed throughout the specification and will be apparent to a reader skilled in the art. The invention is not to be interpreted as being limited to any particular embodiment(s) thereof.

In the first embodiment there is provided a compound of Formula (I):

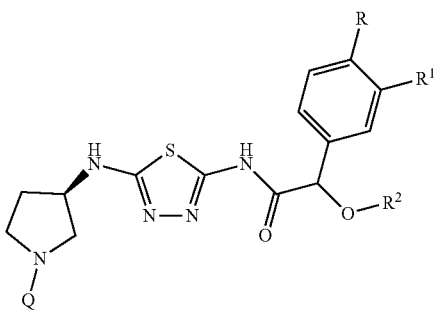

(I)

or a pharmaceutically acceptable salt thereof, where:

Q is pyridazin-3-yl, 1,2,4-triazin-3-yl or 1,2,4-triazin-6-yl;

R is hydro, fluoro or methoxy;

$R^1$ is hydro, methoxy, difluoromethoxy or trifluoromethoxy; and $R^2$ is methyl or ethyl.

In a further embodiment there is provided a compound of Formula (IA):

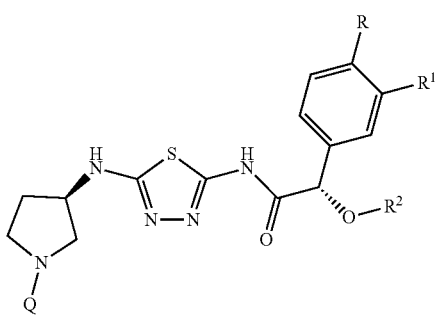

(IA)

or a pharmaceutically acceptable salt thereof, where:

Q is pyridazin-3-yl, 1,2,4-triazin-3-yl or 1,2,4-triazin-6-yl;

R is hydro, fluoro or methoxy;

$R^1$ is hydro, methoxy, difluoromethoxy or trifluoromethoxy; and $R^2$ is methyl or ethyl.

In a further embodiment there is provided a compound of Formula (IB):

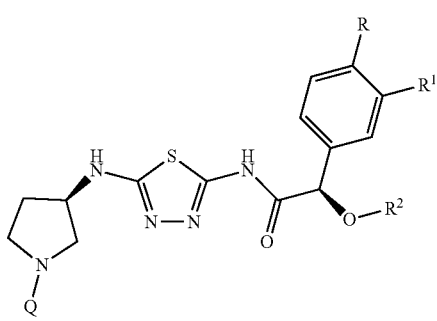

(IB)

or a pharmaceutically acceptable salt thereof, where:

Q is pyridazin-3-yl, 1,2,4-triazin-3-yl or 1,2,4-triazin-6-yl;

R is hydro, fluoro or methoxy;

$R^1$ is hydro, methoxy, difluoromethoxy or trifluoromethoxy; and $R^2$ is methyl or ethyl.

For the avoidance of doubt, compounds of Formula (IA) or (IB) are also compounds of Formula (I) as their structures fall within the definition of Formula (I).

Pyridazin-3-yl, 1,2,4-triazin-3-yl, and 1,2,4-triazin-6-yl rings have the following structures:

Pyridazin-3-yl    1,2,4-Triazin-3-yl    1,2,4-Triazin-6-yl

In the above structures the dashed line indicates the bonding position of the relevant group to the pyrrolidine nitrogen in formula (I), (IA) or (IB).

The term "pharmaceutically acceptable" is used to specify that an object (for example a salt, dosage form, diluent or carrier) is suitable for use in patients. An example list of pharmaceutically acceptable salts can be found in the *Handbook of Pharmaceutical Salts: Properties, Selection and Use*, P. H. Stahl and C. G. Wermuth, editors, Weinheim/Zürich: Wiley-VCH/VHCA, 2002. A suitable pharmaceutically acceptable salt of a compound of Formula (I), (IA) or (IB) is, for example, an acid-addition salt. An acid addition salt of a compound of Formula (I), (IA) or (IB) may be formed by bringing the compound into contact with a suitable inorganic or organic acid under conditions known to the skilled person. An acid addition salt may for example be formed using an inorganic acid selected from the group consisting of hydrochloric acid, hydrobromic acid, sulphuric acid, and phosphoric acid. An acid addition salt may also for example be formed using an organic acid selected from the group consisting of trifluoroacetic acid, methanesulfonic acid and benzenesulfonic acid.

Therefore, in one embodiment there is provided a compound of Formula (I) or a pharmaceutically acceptable salt thereof, where the pharmaceutically acceptable salt is a hydrochloric acid, hydrobromic acid, sulphuric acid, phosphoric acid, trifluoroacetic acid, methanesulfonic acid or benzenesulfonic acid salt. In one embodiment there is provided a compound of Formula (IA) or a pharmaceutically acceptable salt thereof, where the pharmaceutically acceptable salt is a hydrochloric acid, hydrobromic acid, sulphuric acid, phosphoric acid, trifluoroacetic acid, methanesulfonic acid or benzenesulfonic acid salt. In one embodiment there is provided a compound of Formula (IB) or a pharmaceutically acceptable salt thereof, where the pharmaceutically acceptable salt is a hydrochloric acid, hydrobromic acid, sulphuric acid, phosphoric acid, trifluoroacetic acid, methanesulfonic acid or benzenesulfonic acid salt.

In one embodiment there is provided a compound of Formula (I) or a pharmaceutically acceptable salt thereof, where the pharmaceutically acceptable salt is a hydrochloric acid or hydrobromic acid salt. In one embodiment there is provided a compound of Formula (IA) or a pharmaceutically acceptable salt thereof, where the pharmaceutically acceptable salt is a hydrochloric acid or hydrobromic acid salt. In one embodiment there is provided a compound of Formula (IB) or a pharmaceutically acceptable salt thereof, where the pharmaceutically acceptable salt is a hydrochloric acid or hydrobromic acid salt.

A further suitable pharmaceutically acceptable salt of a compound of Formula (I), (IA) or (IB) is a base-addition salt. A base addition salt of a compound of Formula (I), (IA) or (IB) may be formed by bringing the compound into contact with a suitable inorganic or organic base under conditions known to the skilled person. A base addition salt may for example be formed using an inorganic base selected from the group consisting of an alkali metal hydroxide (such as sodium, potassium, or lithium hydroxide) or an alkaline earth metal hydroxide (such as calcium hydroxide or magnesium hydroxide). A base addition salt may also be formed using an organic base selected from the group consisting of methylamine, dimethylamine, trimethylamine, piperidine, morpholine and tris-(2-hydroxyethyl)amine.

Therefore, in one embodiment there is provided a compound of Formula (I) or a pharmaceutically acceptable salt thereof, where the pharmaceutically acceptable salt is a sodium hydroxide, potassium hydroxide, lithium hydroxide, calcium hydroxide, magnesium hydroxide, methylamine, dimethylamine, trimethylamine, piperidine, morpholine or tris-(2-hydroxyethyl)amine salt. In one embodiment there is provided a compound of Formula (IA) or a pharmaceutically acceptable salt thereof, where the pharmaceutically acceptable salt is a sodium hydroxide, potassium hydroxide, lithium hydroxide, calcium hydroxide, magnesium hydroxide, methylamine, dimethylamine, trimethylamine, piperidine, morpholine or tris-(2-hydroxyethyl)amine salt. In one embodiment there is provided a compound of Formula (IB) or a pharmaceutically acceptable salt thereof, where the pharmaceutically acceptable salt is a sodium hydroxide, potassium hydroxide, lithium hydroxide, calcium hydroxide, magnesium hydroxide, methylamine, dimethylamine, trimethylamine, piperidine, morpholine or tris-(2-hydroxyethyl)amine salt.

In one embodiment there is provided a compound of Formula (I) or a pharmaceutically acceptable salt thereof, where the pharmaceutically acceptable salt is a hydrochloric acid, hydrobromic acid, sulphuric acid, phosphoric acid, trifluoroacetic acid, methanesulfonic acid, benzenesulfonic acid, sodium hydroxide, potassium hydroxide, lithium hydroxide, calcium hydroxide, magnesium hydroxide, methylamine, dimethylamine, trimethylamine, piperidine, morpholine or tris-(2-hydroxyethyl)amine salt. In one embodiment there is provided a compound of Formula (IA) or a pharmaceutically acceptable salt thereof, where the pharmaceutically acceptable salt is a hydrochloric acid, hydrobromic acid, sulphuric acid, phosphoric acid, trifluoroacetic acid, methanesulfonic acid, benzenesulfonic acid, sodium hydroxide, potassium hydroxide, lithium hydroxide, calcium hydroxide, magnesium hydroxide, methylamine, dimethylamine, trimethylamine, piperidine, morpholine or tris-(2-hydroxyethyl)amine salt. In one embodiment there is provided a compound of Formula (IB) or a pharmaceutically acceptable salt thereof, where the pharmaceutically acceptable salt is a hydrochloric acid, hydrobromic acid, sulphuric acid, phosphoric acid, trifluoroacetic acid, methanesulfonic acid, benzenesulfonic acid, sodium hydroxide, potassium hydroxide, lithium hydroxide, calcium hydroxide, magnesium hydroxide, methylamine, dimethylamine, trimethylamine, piperidine, morpholine or tris-(2-hydroxyethyl)amine salt.

A further embodiment provides any of the embodiments defined herein (for example the embodiment of claim 1) with the proviso that one or more specific Examples (for instance one, two or three specific Examples, or alternatively two specific Examples, or alternatively one specific Example) selected from the group consisting of Examples 1(a), 1(b), 2(a), 2(b), 3, 4(a), 4(b), 5(a), 5(b), 6(a), 6(b), 7(a), 7(b), 8(a), 8(b), 9(a), 9(b), 10(a), 10(b), 11, 12(a), 12(b), 13(a), 13(b), 14(a), 14(b), 15(a), 15(b), 16(a), 16(b), 17(a), 17(b), 18(a), 18(b), 19(a), 19(b), 20(a), 20(b), 21(a), 21(b), 22(a), 22(b), 23(a), 23(b), 24, 25(a), 25(b), 26(a), 26(b), 27(a), 27(b), 28(a), 28(b), 29(a), 29(b), 30(a), 30(b), 31(a), 31(b), 32(a), 32(b), 33(a), 34(a), 34(b) and 35(b) is individually disclaimed.

Some values of variable groups in Formula (I), (IA) or (IB), as well as in Formula (II) or (III) (as described hereinafter) are as follows. Such values may be used in combination with any of the definitions, claims (for example claim 1), or embodiments defined herein to provide further embodiments.

a) Q is 1,2,4-triazin-3-yl or 1,2,4-triazin-6-yl.
b) Q is pyridazin-3-yl or 1,2,4-triazin-3-yl.
c) Q is 1,2,4-triazin-3-yl.
d) Q is 1,2,4-triazin-6-yl.
e) Q is pyridazin-3-yl.
f) R is hydro or fluoro.
g) R is fluoro or methoxy.
h) R is hydro.
i) R is fluoro.
j) R is methoxy.
k) $R^1$ is hydro.
l) $R^1$ is methoxy, difluoromethoxy or trifluoromethoxy.
m) $R^1$ is methoxy or difluoromethoxy.
n) $R^1$ is methoxy or trifluoromethoxy.
o) $R^1$ is difluoromethoxy or trifluoromethoxy.
p) $R^1$ is methoxy.
q) $R^1$ is difluoromethoxy.
r) $R^1$ is trifluoromethoxy.
s) $R^2$ is methyl.
t) $R^2$ is ethyl.

In one embodiment there is provided a compound of Formula (I), or a pharmaceutically acceptable salt thereof, where:
Q is pyridazin-3-yl or 1,2,4-triazin-3-yl;
R is hydro;
$R^1$ is hydro, methoxy, difluoromethoxy or trifluoromethoxy; and
$R^2$ is methyl or ethyl.

In one embodiment there is provided a compound of Formula (I), or a pharmaceutically acceptable salt thereof, where:
Q is pyridazin-3-yl or 1,2,4-triazin-3-yl;
R is fluoro or methoxy;
$R^1$ is hydro, and
$R^2$ is methyl or ethyl.

In one embodiment there is provided a compound of Formula (I), or a pharmaceutically acceptable salt thereof, where:
Q is pyridazin-3-yl;
R is hydro, fluoro or methoxy;
$R^1$ is hydro; and
$R^2$ is methyl or ethyl.

In one embodiment there is provided a compound of Formula (IA), or a pharmaceutically acceptable salt thereof, where:
Q is pyridazin-3-yl or 1,2,4-triazin-3-yl;
R is hydro;
$R^1$ is hydro, methoxy, difluoromethoxy or trifluoromethoxy; and
$R^2$ is methyl or ethyl.

In one embodiment there is provided a compound of Formula (IA), or a pharmaceutically acceptable salt thereof, where:
Q is pyridazin-3-yl or 1,2,4-triazin-3-yl;
R is fluoro or methoxy;
$R^1$ is hydro, and
$R^2$ is methyl or ethyl.

In one embodiment there is provided a compound of Formula (IA), or a pharmaceutically acceptable salt thereof, where:
Q is pyridazin-3-yl;
R is hydro, fluoro or methoxy;
$R^1$ is hydro; and
$R^2$ is methyl or ethyl.

In one embodiment there is provided a compound of Formula (IB), or a pharmaceutically acceptable salt thereof, where:
Q is pyridazin-3-yl or 1,2,4-triazin-3-yl;
R is hydro;
$R^1$ is hydro, methoxy, difluoromethoxy or trifluoromethoxy; and
$R^2$ is methyl or ethyl.

In one embodiment there is provided a compound of Formula (IB), or a pharmaceutically acceptable salt thereof, where:
Q is pyridazin-3-yl or 1,2,4-triazin-3-yl;
R is fluoro or methoxy;
$R^1$ is hydro, and
$R^2$ is methyl or ethyl.

In one embodiment there is provided a compound of Formula (IB), or a pharmaceutically acceptable salt thereof, where:
Q is pyridazin-3-yl;
R is hydro, fluoro or methoxy;
$R^1$ is hydro; and
$R^2$ is methyl or ethyl.

In one embodiment there is provided a compound of Formula (I), or a pharmaceutically acceptable salt thereof, where the compound is selected from the group consisting of:
(2S)-2-Methoxy-2-phenyl-N-[5-[[(3R)-1-(1,2,4-triazin-3-yl)pyrrolidin-3-yl]amino]-1,3,4-thiadiazol-2-yl]acetamide;
(2R)-2-Methoxy-2-phenyl-N-[5-[[(3R)-1-(1,2,4-triazin-3-yl)pyrrolidin-3-yl]amino]-1,3,4-thiadiazol-2-yl]acetamide;
(2S)-2-Methoxy-2-phenyl-N-[5-[[(3R)-1-pyridazin-3-ylpyrrolidin-3-yl]amino]-1,3,4-thiadiazol-2-yl]acetamide;
(2R)-2-Methoxy-2-phenyl-N-[5-[[(3R)-1-pyridazin-3-ylpyrrolidin-3-yl]amino]-1,3,4-thiadiazol-2-yl]acetamide;
(2S)-2-Methoxy-2-phenyl-N-[5-[[(3R)-1-(1,2,4-triazin-6-yl)pyrrolidin-3-yl]amino]-1,3,4-thiadiazol-2-yl]acetamide;
(2S)-2-Methoxy-2-(3-methoxyphenyl)-N-[5-[[(3R)-1-(1,2,4-triazin-3-yl)pyrrolidin-3-yl]amino]-1,3,4-thiadiazol-2-yl]acetamide;
(2R)-2-Methoxy-2-(3-methoxyphenyl)-N-[5-[[(3R)-1-(1,2,4-triazin-3-yl)pyrrolidin-3-yl]amino]-1,3,4-thiadiazol-2-yl]acetamide;
(2S)-2-Methoxy-2-(3-methoxyphenyl)-N-[5-[[(3R)-1-pyridazin-3-ylpyrrolidin-3-yl]amino]-1,3,4-thiadiazol-2-yl]acetamide;
(2R)-2-Methoxy-2-(3-methoxyphenyl)-N-[5-[[(3R)-1-pyridazin-3-ylpyrrolidin-3-yl]amino]-1,3,4-thiadiazol-2-yl]acetamide;
(2S)-2-[3-(Difluoromethoxy)phenyl]-2-methoxy-N-[5-[[(3R)-1-(1,2,4-triazin-3-yl)pyrrolidin-3-yl]amino]-1,3,4-thiadiazol-2-yl]acetamide;
(2R)-2-[3-(Difluoromethoxy)phenyl]-2-methoxy-N-[5-[[(3R)-1-(1,2,4-triazin-3-yl)pyrrolidin-3-yl]amino]-1,3,4-thiadiazol-2-yl]acetamide;
(2S)-2-[3-(Difluoromethoxy)phenyl]-2-methoxy-N-[5-[[(3R)-1-pyridazin-3-ylpyrrolidin-3-yl]amino]-1,3,4-thiadiazol-2-yl]acetamide;
(2R)-2-[3-(Difluoromethoxy)phenyl]-2-methoxy-N-[5-[[(3R)-1-pyridazin-3-ylpyrrolidin-3-yl]amino]-1,3,4-thiadiazol-2-yl]acetamide;
(2S)-2-Methoxy-N-[5-[[(3R)-1-(1,2,4-triazin-3-yl)pyrrolidin-3-yl]amino]-1,3,4-thiadiazol-2-yl]-2-[3-(trifluoromethoxy)phenyl]acetamide;
(2R)-2-Methoxy-N-[5-[[(3R)-1-(1,2,4-triazin-3-yl)pyrrolidin-3-yl]amino]-1,3,4-thiadiazol-2-yl]-2-[3-(trifluoromethoxy)phenyl]acetamide;
(2S)-2-Methoxy-N-[5-[[(3R)-1-pyridazin-3-ylpyrrolidin-3-yl]amino]-1,3,4-thiadiazol-2-yl]-2-[3-(trifluoromethoxy)phenyl]acetamide;
(2R)-2-Methoxy-N-[5-[[(3R)-1-pyridazin-3-ylpyrrolidin-3-yl]amino]-1,3,4-thiadiazol-2-yl]-2-[3-(trifluoromethoxy)phenyl]acetamide;
(2S)-2-Ethoxy-2-phenyl-N-[5-[[(3R)-1-pyridazin-3-ylpyrrolidin-3-yl]amino]-1,3,4-thiadiazol-2-yl]acetamide;
(2S)-2-Methoxy-2-(4-methoxyphenyl)-N-[5-[[(3R)-1-pyridazin-3-ylpyrrolidin-3-yl]amino]-1,3,4-thiadiazol-2-yl]acetamide
(2R)-2-Ethoxy-2-phenyl-N-[5-[[(3R)-1-pyridazin-3-ylpyrrolidin-3-yl]amino]-1,3,4-thiadiazol-2-yl]acetamide;
(2S)-2-(4-Fluorophenyl)-2-methoxy-N-[5-[[(3R)-1-pyridazin-3-ylpyrrolidin-3-yl]amino]-1,3,4-thiadiazol-2-yl]acetamide;
(2R)-2-(4-Fluorophenyl)-2-methoxy-N-[5-[[(3R)-1-pyridazin-3-ylpyrrolidin-3-yl]amino]-1,3,4-thiadiazol-2-yl]acetamide;
(2S)-2-Ethoxy-2-(4-fluorophenyl)-N-[5-[[(3R)-1-pyridazin-3-ylpyrrolidin-3-yl]amino]-1,3,4-thiadiazol-2-yl]acetamide;
(2R)-2-Ethoxy-2-(4-fluorophenyl)-N-[5-[[(3R)-1-pyridazin-3-ylpyrrolidin-3-yl]amino]-1,3,4-thiadiazol-2-yl]acetamide;
(2S)-2-(4-Fluoro-3-methoxy-phenyl)-2-methoxy-N-[5-[[(3R)-1-pyridazin-3-ylpyrrolidin-3-yl]amino]-1,3,4-thiadiazol-2-yl]acetamide;
(2R)-2-(4-Fluoro-3-methoxy-phenyl)-2-methoxy-N-[5-[[(3R)-1-pyridazin-3-ylpyrrolidin-3-yl]amino]-1,3,4-thiadiazol-2-yl]acetamide;
(2S)-2-[3-(Difluoromethoxy)phenyl]-2-ethoxy-N-[5-[[(3R)-1-pyridazin-3-ylpyrrolidin-3-yl]amino]-1,3,4-thiadiazol-2-yl]acetamide;
(2R)-2-[3-(Difluoromethoxy)phenyl]-2-ethoxy-N-[5-[[(3R)-1-pyridazin-3-ylpyrrolidin-3-yl]amino]-1,3,4-thiadiazol-2-yl]acetamide;
(2S)-2-Ethoxy-N-[5-[[(3R)-1-pyridazin-3-ylpyrrolidin-3-yl]amino]-1,3,4-thiadiazol-2-yl]-2-[3-(trifluoromethoxy)phenyl]acetamide;
(2R)-2-Ethoxy-N-[5-[[(3R)-1-pyridazin-3-ylpyrrolidin-3-yl]amino]-1,3,4-thiadiazol-2-yl]-2-[3-(trifluoromethoxy)phenyl]acetamide; (2S)-2-(4-Fluorophenyl)-2-methoxy-N-[5-[[(3R)-1-(1,2,4-triazin-3-yl)pyrrolidin-3-yl]amino]-1,3,4-thiadiazol-2-yl]acetamide;
(2R)-2-(4-Fluorophenyl)-2-methoxy-N-[5-[[(3R)-1-(1,2,4-triazin-3-yl)pyrrolidin-3-yl]amino]-1,3,4-thiadiazol-2-yl]acetamide;

(2S)-2-Phenyl-N-[5-[[(3R)-1-pyridazin-3-ylpyrrolidin-3-yl]amino]-1,3,4-thiadiazol-2-yl]-2-(trideuteriomethoxy)acetamide;
(2R)-2-Phenyl-N-[5-[[(3R)-1-pyridazin-3-ylpyrrolidin-3-yl]amino]-1,3,4-thiadiazol-2-yl]-2-(trideuteriomethoxy)acetamide;
(2S)-2-[3-(Difluoromethoxy)phenyl]-2-methoxy-N-[5-[[(3R)-1-(1,2,4-triazin-3-yl)pyrrolidin-3-yl]amino]-1,3,4-thiadiazol-2-yl]acetamide;
(2R)-2-[3-(Difluoromethoxy)phenyl]-2-methoxy-N-[5-[[(3R)-1-(1,2,4-triazin-3-yl)pyrrolidin-3-yl]amino]-1,3,4-thiadiazol-2-yl]acetamide;
(2S)-2-Deuterio-2-phenyl-N-[5-[[(3R)-1-pyridazin-3-ylpyrrolidin-3-yl]amino]-1,3,4-thiadiazol-2-yl]-2-(trideuteriomethoxy)acetamide;
(2R)-2-Deuterio-2-phenyl-N-[5-[[(3R)-1-pyridazin-3-ylpyrrolidin-3-yl]amino]-1,3,4-thiadiazol-2-yl]-2-(trideuteriomethoxy)acetamide;
(2S)-2-Methoxy-2-(3-methoxyphenyl)-N-[5-[[(3R)-1-(1,2,4-triazin-6-yl)pyrrolidin-3-yl]amino]-1,3,4-thiadiazol-2-yl]acetamide;
(2R)-2-Methoxy-2-(3-methoxyphenyl)-N-[5-[[(3R)-1-(1,2,4-triazin-6-yl)pyrrolidin-3-yl]amino]-1,3,4-thiadiazol-2-yl]acetamide;
(2S)-2-Methoxy-N-[5-[[(3R)-1-(1,2,4-triazin-6-yl)pyrrolidin-3-yl]amino]-1,3,4-thiadiazol-2-yl]-2-[3-(trifluoromethoxy)phenyl]acetamide;
is (2R)-2-Methoxy-N-[5-[[(3R)-1-(1,2,4-triazin-6-yl)pyrrolidin-3-yl]amino]-1,3,4-thiadiazol-2-yl]-2-[3-(trifluoromethoxy)phenyl]acetamide;
(2S)-2-[3-(Difluoromethoxy)phenyl]-2-methoxy-N-[5-[[(3R)-1-(1,2,4-triazin-6-yl)pyrrolidin-3-yl]amino]-1,3,4-thiadiazol-2-yl]acetamide;
(2R)-2-[3-(Difluoromethoxy)phenyl]-2-methoxy-N-[5-[[(3R)-1-(1,2,4-triazin-6-yl)pyrrolidin-3-yl]amino]-1,3,4-thiadiazol-2-yl]acetamide;
(2S)-2-Methoxy-2-(4-methoxyphenyl)-N-[5-[[(3R)-1-(1,2,4-triazin-3-yl)pyrrolidin-3-yl]amino]-1,3,4-thiadiazol-2-yl]acetamide;
(2S)-2-(3,4-Dimethoxyphenyl)-2-methoxy-N-[5-[[(3R)-1-pyridazin-3-ylpyrrolidin-3-yl]amino]-1,3,4-thiadiazol-2-yl]acetamide;
(2R)-2-(3,4-Dimethoxyphenyl)-2-methoxy-N-[5-[[(3R)-1-pyridazin-3-ylpyrrolidin-3-yl]amino]-1,3,4-thiadiazol-2-yl]acetamide;
(2S)-2-(3,4-Dimethoxyphenyl)-2-methoxy-N-[5-[[(3R)-1-(1,2,4-triazin-3-yl)pyrrolidin-3-yl]amino]-1,3,4-thiadiazol-2-yl]acetamide;
(2R)-2-(3,4-Dimethoxyphenyl)-2-methoxy-N-[5-[[(3R)-1-(1,2,4-triazin-3-yl)pyrrolidin-3-yl]amino]-1,3,4-thiadiazol-2-yl]acetamide;
(2S)-2-Ethoxy-2-(3-methoxyphenyl)-N-[5-[[(3R)-1-(1,2,4-triazin-3-yl)pyrrolidin-3-yl]amino]-1,3,4-thiadiazol-2-yl]acetamide;
(2R)-2-Ethoxy-2-(3-methoxyphenyl)-N-[5-[[(3R)-1-(1,2,4-triazin-3-yl)pyrrolidin-3-yl]amino]-1,3,4-thiadiazol-2-yl]acetamide;
(2S)-2-Ethoxy-2-(4-methoxyphenyl)-N-[5-[[(3R)-1-pyridazin-3-ylpyrrolidin-3-yl]amino]-1,3,4-thiadiazol-2-yl]acetamide;
(2R)-2-Ethoxy-2-(4-methoxyphenyl)-N-[5-[[(3R)-1-pyridazin-3-ylpyrrolidin-3-yl]amino]-1,3,4-thiadiazol-2-yl]acetamide;
(2S)-2-Ethoxy-2-(4-methoxyphenyl)-N-[5-[[(3R)-1-(1,2,4-triazin-3-yl)pyrrolidin-3-yl]amino]-1,3,4-thiadiazol-2-yl]acetamide;
(2R)-2-Ethoxy-2-(4-methoxyphenyl)-N-[5-[[(3R)-1-(1,2,4-triazin-3-yl)pyrrolidin-3-yl]amino]-1,3,4-thiadiazol-2-yl]acetamide;
(2S)-2-Ethoxy-2-(3-methoxyphenyl)-N-[5-[[(3R)-1-pyridazin-3-ylpyrrolidin-3-yl]amino]-1,3,4-thiadiazol-2-yl]acetamide;
(2R)-2-Ethoxy-2-(3-methoxyphenyl)-N-[5-[[(3R)-1-pyridazin-3-ylpyrrolidin-3-yl]amino]-1,3,4-thiadiazol-2-yl]acetamide;
(2S)-2-Ethoxy-2-(4-fluoro-3-methoxy-phenyl)-N-[5-[[(3R)-1-pyridazin-3-ylpyrrolidin-3-yl]amino]-1,3,4-thiadiazol-2-yl]acetamide;
(2R)-2-Ethoxy-2-(4-fluoro-3-methoxy-phenyl)-N-[5-[[(3R)-1-pyridazin-3-ylpyrrolidin-3-yl]amino]-1,3,4-thiadiazol-2-yl]acetamide;
(2S)-2-(4-Fluoro-3-methoxy-phenyl)-2-methoxy-N-[5-[[(3R)-1-(1,2,4-triazin-3-yl)pyrrolidin-3-yl]amino]-1,3,4-thiadiazol-2-yl]acetamide;
(2R)-2-(4-Fluoro-3-methoxy-phenyl)-2-methoxy-N-[5-[[(3R)-1-(1,2,4-triazin-3-yl)pyrrolidin-3-yl]amino]-1,3,4-thiadiazol-2-yl]acetamide;
(2S)-2-Ethoxy-2-(4-fluoro-3-methoxy-phenyl)-N-[5-[[(3R)-1-(1,2,4-triazin-3-yl)pyrrolidin-3-yl]amino]-1,3,4-thiadiazol-2-yl]acetamide;
(2R)-2-Ethoxy-2-(4-fluoro-3-methoxy-phenyl)-N-[5-[[(3R)-1-(1,2,4-triazin-3-yl)pyrrolidin-3-yl]amino]-1,3,4-thiadiazol-2-yl]acetamide;
(2S)-2-Ethoxy-2-phenyl-N-[5-[[(3R)-1-(1,2,4-triazin-3-yl)pyrrolidin-3-yl]amino]-1,3,4-thiadiazol-2-yl]acetamide;
(2R)-2-Ethoxy-2-phenyl-N-[5-[[(3R)-1-(1,2,4-triazin-3-yl)pyrrolidin-3-yl]amino]-1,3,4-thiadiazol-2-yl]acetamide;
(2S)-2-Ethoxy-2-(4-fluorophenyl)-N-[5-[[(3R)-1-(1,2,4-triazin-3-yl)pyrrolidin-3-yl]amino]-1,3,4-thiadiazol-2-yl]acetamide; and
(2R)-2-Ethoxy-2-(4-fluorophenyl)-N-[5-[[(3R)-1-(1,2,4-triazin-3-yl)pyrrolidin-3-yl]amino]-1,3,4-thiadiazol-2-yl]acetamide In one embodiment there is provided a compound of Formula (I), or a pharmaceutically acceptable salt thereof, where the compound is selected from the group consisting of:
(2S)-2-Methoxy-2-phenyl-N-[5-[[(3R)-1-(1,2,4-triazin-3-yl)pyrrolidin-3-yl]amino]-1,3,4-thiadiazol-2-yl]acetamide;
(2R)-2-Methoxy-2-phenyl-N-[5-[[(3R)-1-(1,2,4-triazin-3-yl)pyrrolidin-3-yl]amino]-1,3,4-thiadiazol-2-yl]acetamide;
(2S)-2-Methoxy-2-phenyl-N-[5-[[(3R)-1-pyridazin-3-ylpyrrolidin-3-yl]amino]-1,3,4-thiadiazol-2-yl]acetamide;
(2R)-2-Methoxy-2-phenyl-N-[5-[[(3R)-1-pyridazin-3-ylpyrrolidin-3-yl]amino]-1,3,4-thiadiazol-2-yl]acetamide;
(2S)-2-Methoxy-2-phenyl-N-[5-[[(3R)-1-(1,2,4-triazin-6-yl)pyrrolidin-3-yl]amino]-1,3,4-thiadiazol-2-yl]acetamide;
(2S)-2-Methoxy-2-(3-methoxyphenyl)-N-[5-[[(3R)-1-(1,2,4-triazin-3-yl)pyrrolidin-3-yl]amino]-1,3,4-thiadiazol-2-yl]acetamide;
(2R)-2-Methoxy-2-(3-methoxyphenyl)-N-[5-[[(3R)-1-(1,2,4-triazin-3-yl)pyrrolidin-3-yl]amino]-1,3,4-thiadiazol-2-yl]acetamide;
(2S)-2-Methoxy-2-(3-methoxyphenyl)-N-[5-[[(3R)-1-pyridazin-3-ylpyrrolidin-3-yl]amino]-1,3,4-thiadiazol-2-yl]acetamide;
(2R)-2-Methoxy-2-(3-methoxyphenyl)-N-[5-[[(3R)-1-pyridazin-3-ylpyrrolidin-3-yl]amino]-1,3,4-thiadiazol-2-yl]acetamide;

(2S)-2-[3-(Difluoromethoxy)phenyl]-2-methoxy-N-[5-[[(3R)-1-(1,2,4-triazin-3-yl)pyrrolidin-3-yl]amino]-1,3,4-thiadiazol-2-yl]acetamide;
(2R)-2-[3-(Difluoromethoxy)phenyl]-2-methoxy-N-[5-[[(3R)-1-(1,2,4-triazin-3-yl)pyrrolidin-3-yl]amino]-1,3,4-thiadiazol-2-yl]acetamide;
(2S)-2-[3-(Difluoromethoxy)phenyl]-2-methoxy-N-[5-[[(3R)-1-pyridazin-3-ylpyrrolidin-3-yl]amino]-1,3,4-thiadiazol-2-yl]acetamide;
(2R)-2-[3-(Difluoromethoxy)phenyl]-2-methoxy-N-[5-[[(3R)-1-pyridazin-3-ylpyrrolidin-3-yl]amino]-1,3,4-thiadiazol-2-yl]acetamide;
(2S)-2-Methoxy-N-[5-[[(3R)-1-(1,2,4-triazin-3-yl)pyrrolidin-3-yl]amino]-1,3,4-thiadiazol-2-yl]-2-[3-(trifluoromethoxy)phenyl]acetamide;
(2R)-2-Methoxy-N-[5-[[(3R)-1-(1,2,4-triazin-3-yl)pyrrolidin-3-yl]amino]-1,3,4-thiadiazol-2-yl]-2-[3-(trifluoromethoxy)phenyl]acetamide;
(2S)-2-Methoxy-N-[5-[[(3R)-1-pyridazin-3-ylpyrrolidin-3-yl]amino]-1,3,4-thiadiazol-2-yl]-2-[3-(trifluoromethoxy)phenyl]acetamide;
(2R)-2-Methoxy-N-[5-[[(3R)-1-pyridazin-3-ylpyrrolidin-3-yl]amino]-1,3,4-thiadiazol-2-yl]-2-[3-(trifluoromethoxy)phenyl]acetamide;
(2S)-2-Ethoxy-2-phenyl-N-[5-[[(3R)-1-pyridazin-3-ylpyrrolidin-3-yl]amino]-1,3,4-thiadiazol-2-yl]acetamide;
(2S)-2-Methoxy-2-(4-methoxyphenyl)-N-[5-[[(3R)-1-pyridazin-3-ylpyrrolidin-3-yl]amino]-1,3,4-thiadiazol-2-yl]acetamide
(2R)-2-Ethoxy-2-phenyl-N-[5-[[(3R)-1-pyridazin-3-ylpyrrolidin-3-yl]amino]-1,3,4-thiadiazol-2-yl]acetamide;
(2S)-2-(4-Fluorophenyl)-2-methoxy-N-[5-[[(3R)-1-pyridazin-3-ylpyrrolidin-3-yl]amino]-1,3,4-thiadiazol-2-yl]acetamide;
(2R)-2-(4-Fluorophenyl)-2-methoxy-N-[5-[[(3R)-1-pyridazin-3-ylpyrrolidin-3-yl]amino]-1,3,4-thiadiazol-2-yl]acetamide;
(2S)-2-Ethoxy-2-(4-fluorophenyl)-N-[5-[[(3R)-1-pyridazin-3-ylpyrrolidin-3-yl]amino]-1,3,4-thiadiazol-2-yl]acetamide;
(2R)-2-Ethoxy-2-(4-fluorophenyl)-N-[5-[[(3R)-1-pyridazin-3-ylpyrrolidin-3-yl]amino]-1,3,4-thiadiazol-2-yl]acetamide;
(2S)-2-(4-Fluoro-3-methoxy-phenyl)-2-methoxy-N-[5-[[(3R)-1-pyridazin-3-ylpyrrolidin-3-yl]amino]-1,3,4-thiadiazol-2-yl]acetamide;
(2R)-2-(4-Fluoro-3-methoxy-phenyl)-2-methoxy-N-[5-[[(3R)-1-pyridazin-3-ylpyrrolidin-3-yl]amino]-1,3,4-thiadiazol-2-yl]acetamide;
(2S)-2-[3-(Difluoromethoxy)phenyl]-2-ethoxy-N-[5-[[(3R)-1-pyridazin-3-ylpyrrolidin-3-yl]amino]-1,3,4-thiadiazol-2-yl]acetamide;
(2R)-2-[3-(Difluoromethoxy)phenyl]-2-ethoxy-N-[5-[[(3R)-1-pyridazin-3-ylpyrrolidin-3-yl]amino]-1,3,4-thiadiazol-2-yl]acetamide;
(2S)-2-Ethoxy-N-[5-[[(3R)-1-pyridazin-3-ylpyrrolidin-3-yl]amino]-1,3,4-thiadiazol-2-yl]-2-[3-(trifluoromethoxy)phenyl]acetamide; and
(2R)-2-Ethoxy-N-[5-[[(3R)-1-pyridazin-3-ylpyrrolidin-3-yl]amino]-1,3,4-thiadiazol-2-yl]-2-[3-(trifluoromethoxy)phenyl]acetamide.

In one embodiment there is provided a compound of Formula (I), or a pharmaceutically acceptable salt thereof, where the compound is selected from the group consisting of:

(2R)-2-Methoxy-2-phenyl-N-[5-[[(3R)-1-(1,2,4-triazin-3-yl)pyrrolidin-3-yl]amino]-1,3,4-thiadiazol-2-yl]acetamide;
(2R)-2-Methoxy-2-phenyl-N-[5-[[(3R)-1-pyridazin-3-ylpyrrolidin-3-yl]amino]-1,3,4-thiadiazol-2-yl]acetamide;
(2S)-2-Ethoxy-2-(4-fluorophenyl)-N-[5-[[(3R)-1-pyridazin-3-ylpyrrolidin-3-yl]amino]-1,3,4-thiadiazol-2-yl]acetamide;
(2R)-2-Ethoxy-2-(4-fluorophenyl)-N-[5-[[(3R)-1-pyridazin-3-ylpyrrolidin-3-yl]amino]-1,3,4-thiadiazol-2-yl]acetamide;
(2S)-2-(4-Fluoro-3-methoxy-phenyl)-2-methoxy-N-[5-[[(3R)-1-pyridazin-3-ylpyrrolidin-3-yl]amino]-1,3,4-thiadiazol-2-yl]acetamide;
(2R)-2-(4-Fluoro-3-methoxy-phenyl)-2-methoxy-N-[5-[[(3R)-1-pyridazin-3-ylpyrrolidin-3-yl]amino]-1,3,4-thiadiazol-2-yl]acetamide;
(2S)-2-[3-(Difluoromethoxy)phenyl]-2-ethoxy-N-[5-[[(3R)-1-pyridazin-3-ylpyrrolidin-3-yl]amino]-1,3,4-thiadiazol-2-yl]acetamide;
(2R)-2-[3-(Difluoromethoxy)phenyl]-2-ethoxy-N-[5-[[(3R)-1-pyridazin-3-ylpyrrolidin-3-yl]amino]-1,3,4-thiadiazol-2-yl]acetamide;
(2S)-2-Ethoxy-N-[5-[[(3R)-1-pyridazin-3-ylpyrrolidin-3-yl]amino]-1,3,4-thiadiazol-2-yl]-2-[3-(trifluoromethoxy)phenyl]acetamide; and (2R)-2-Ethoxy-N-[5-[[(3R)-1-pyridazin-3-ylpyrrolidin-3-yl]amino]-1,3,4-thiadiazol-2-yl]-2-[3-(trifluoromethoxy)phenyl]acetamide.

In one embodiment there is provided a compound of Formula (I), or a pharmaceutically acceptable salt thereof, where the compound is selected from the group consisting of:

(2S)-2-(4-Fluorophenyl)-2-methoxy-N-[5-[[(3R)-1-(1,2,4-triazin-3-yl)pyrrolidin-3-yl]amino]-1,3,4-thiadiazol-2-yl]acetamide;
(2R)-2-(4-Fluorophenyl)-2-methoxy-N-[5-[[(3R)-1-(1,2,4-triazin-3-yl)pyrrolidin-3-yl]amino]-1,3,4-thiadiazol-2-yl]acetamide;
(2S)-2-Phenyl-N-[5-[[(3R)-1-pyridazin-3-ylpyrrolidin-3-yl]amino]-1,3,4-thiadiazol-2-yl]-2-(trideuteriomethoxy)acetamide;
(2R)-2-Phenyl-N-[5-[[(3R)-1-pyridazin-3-ylpyrrolidin-3-yl]amino]-1,3,4-thiadiazol-2-yl]-2-(trideuteriomethoxy)acetamide;
(2S)-2-[3-(Difluoromethoxy)phenyl]-2-methoxy-N-[5-[[(3R)-1-(1,2,4-triazin-3-yl)pyrrolidin-3-yl]amino]-1,3,4-thiadiazol-2-yl]acetamide;
(2R)-2-[3-(Difluoromethoxy)phenyl]-2-methoxy-N-[5-[[(3R)-1-(1,2,4-triazin-3-yl)pyrrolidin-3-yl]amino]-1,3,4-thiadiazol-2-yl]acetamide;
(2S)-2-Deuterio-2-phenyl-N-[5-[[(3R)-1-pyridazin-3-ylpyrrolidin-3-yl]amino]-1,3,4-thiadiazol-2-yl]-2-(trideuteriomethoxy)acetamide;
(2R)-2-Deuterio-2-phenyl-N-[5-[[(3R)-1-pyridazin-3-ylpyrrolidin-3-yl]amino]-1,3,4-thiadiazol-2-yl]-2-(trideuteriomethoxy)acetamide;
(2S)-2-Methoxy-2-(3-methoxyphenyl)-N-[5-[[(3R)-1-(1,2,4-triazin-6-yl)pyrrolidin-3-yl]amino]-1,3,4-thiadiazol-2-yl]acetamide;
(2R)-2-Methoxy-2-(3-methoxyphenyl)-N-[5-[[(3R)-1-(1,2,4-triazin-6-yl)pyrrolidin-3-yl]amino]-1,3,4-thiadiazol-2-yl]acetamide;
(2S)-2-Methoxy-N-[5-[[(3R)-1-(1,2,4-triazin-6-yl)pyrrolidin-3-yl]amino]-1,3,4-thiadiazol-2-yl]-2-[3-(trifluoromethoxy)phenyl]acetamide;

(2R)-2-Methoxy-N-[5-[[(3R)-1-(1,2,4-triazin-6-yl)pyrrolidin-3-yl]amino]-1,3,4-thiadiazol-2-yl]-2-[3-(trifluoromethoxy)phenyl]acetamide;

(2S)-2-[3-(Difluoromethoxy)phenyl]-2-methoxy-N-[5-[[(3R)-1-(1,2,4-triazin-6-yl)pyrrolidin-3-yl]amino]-1,3,4-thiadiazol-2-yl]acetamide;

(2R)-2-[3-(Difluoromethoxy)phenyl]-2-methoxy-N-[5-[[(3R)-1-(1,2,4-triazin-6-yl)pyrrolidin-3-yl]amino]-1,3,4-thiadiazol-2-yl]acetamide;

(2S)-2-Methoxy-2-(4-methoxyphenyl)-N-[5-[[(3R)-1-(1,2,4-triazin-3-yl)pyrrolidin-3-yl]amino]-1,3,4-thiadiazol-2-yl]acetamide;

(2S)-2-(3,4-Dimethoxyphenyl)-2-methoxy-N-[5-[[(3R)-1-pyridazin-3-ylpyrrolidin-3-yl]amino]-1,3,4-thiadiazol-2-yl]acetamide;

(2R)-2-(3,4-Dimethoxyphenyl)-2-methoxy-N-[5-[[(3R)-1-pyridazin-3-ylpyrrolidin-3-yl]amino]-1,3,4-thiadiazol-2-yl]acetamide;

(2S)-2-(3,4-Dimethoxyphenyl)-2-methoxy-N-[5-[[(3R)-1-(1,2,4-triazin-3-yl)pyrrolidin-3-yl]amino]-1,3,4-thiadiazol-2-yl]acetamide;

(2R)-2-(3,4-Dimethoxyphenyl)-2-methoxy-N-[5-[[(3R)-1-(1,2,4-triazin-3-yl)pyrrolidin-3-yl]amino]-1,3,4-thiadiazol-2-yl]acetamide;

(2S)-2-Ethoxy-2-(3-methoxyphenyl)-N-[5-[[(3R)-1-(1,2,4-triazin-3-yl)pyrrolidin-3-yl]amino]-1,3,4-thiadiazol-2-yl]acetamide;

(2R)-2-Ethoxy-2-(3-methoxyphenyl)-N-[5-[[(3R)-1-(1,2,4-triazin-3-yl)pyrrolidin-3-yl]amino]-1,3,4-thiadiazol-2-yl]acetamide;

(2S)-2-Ethoxy-2-(4-methoxyphenyl)-N-[5-[[(3R)-1-pyridazin-3-ylpyrrolidin-3-yl]amino]-1,3,4-thiadiazol-2-yl]acetamide;

(2R)-2-Ethoxy-2-(4-methoxyphenyl)-N-[5-[[(3R)-1-pyridazin-3-ylpyrrolidin-3-yl]amino]-1,3,4-thiadiazol-2-yl]acetamide;

(2S)-2-Ethoxy-2-(4-methoxyphenyl)-N-[5-[[(3R)-1-(1,2,4-triazin-3-yl)pyrrolidin-3-yl]amino]-1,3,4-thiadiazol-2-yl]acetamide;

(2R)-2-Ethoxy-2-(4-methoxyphenyl)-N-[5-[[(3R)-1-(1,2,4-triazin-3-yl)pyrrolidin-3-yl]amino]-1,3,4-thiadiazol-2-yl]acetamide;

(2S)-2-Ethoxy-2-(3-methoxyphenyl)-N-[5-[[(3R)-1-pyridazin-3-ylpyrrolidin-3-yl]amino]-1,3,4-thiadiazol-2-yl]acetamide;

(2R)-2-Ethoxy-2-(3-methoxyphenyl)-N-[5-[[(3R)-1-pyridazin-3-ylpyrrolidin-3-yl]amino]-1,3,4-thiadiazol-2-yl]acetamide;

(2S)-2-Ethoxy-2-(4-fluoro-3-methoxy-phenyl)-N-[5-[[(3R)-1-pyridazin-3-ylpyrrolidin-3-yl]amino]-1,3,4-thiadiazol-2-yl]acetamide;

(2R)-2-Ethoxy-2-(4-fluoro-3-methoxy-phenyl)-N-[5-[[(3R)-1-pyridazin-3-ylpyrrolidin-3-yl]amino]-1,3,4-thiadiazol-2-yl]acetamide;

(2S)-2-(4-Fluoro-3-methoxy-phenyl)-2-methoxy-N-[5-[[(3R)-1-(1,2,4-triazin-3-yl)pyrrolidin-3-yl]amino]-1,3,4-thiadiazol-2-yl]acetamide;

(2R)-2-(4-Fluoro-3-methoxy-phenyl)-2-methoxy-N-[5-[[(3R)-1-(1,2,4-triazin-3-yl)pyrrolidin-3-yl]amino]-1,3,4-thiadiazol-2-yl]acetamide;

(2S)-2-Ethoxy-2-(4-fluoro-3-methoxy-phenyl)-N-[5-[[(3R)-1-(1,2,4-triazin-3-yl)pyrrolidin-3-yl]amino]-1,3,4-thiadiazol-2-yl]acetamide;

(2R)-2-Ethoxy-2-(4-fluoro-3-methoxy-phenyl)-N-[5-[[(3R)-1-(1,2,4-triazin-3-yl)pyrrolidin-3-yl]amino]-1,3,4-thiadiazol-2-yl]acetamide;

(2S)-2-Ethoxy-2-phenyl-N-[5-[[(3R)-1-(1,2,4-triazin-3-yl)pyrrolidin-3-yl]amino]-1,3,4-thiadiazol-2-yl]acetamide;

(2R)-2-Ethoxy-2-phenyl-N-[5-[[(3R)-1-(1,2,4-triazin-3-yl)pyrrolidin-3-yl]amino]-1,3,4-thiadiazol-2-yl]acetamide;

(2S)-2-Ethoxy-2-(4-fluorophenyl)-N-[5-[[(3R)-1-(1,2,4-triazin-3-yl)pyrrolidin-3-yl]amino]-1,3,4-thiadiazol-2-yl]acetamide; and (2R)-2-Ethoxy-2-(4-fluorophenyl)-N-[5-[[(3R)-1-(1,2,4-triazin-3-yl)pyrrolidin-3-yl]amino]-1,3,4-thiadiazol-2-yl]acetamide.

In one embodiment there is provided a compound of Formula (IA), or a pharmaceutically acceptable salt thereof, where the compound is selected from the group consisting of:

(2S)-2-Methoxy-2-phenyl-N-[5-[[(3R)-1-(1,2,4-triazin-3-yl)pyrrolidin-3-yl]amino]-1,3,4-thiadiazol-2-yl]acetamide;

(2S)-2-Methoxy-2-phenyl-N-[5-[[(3R)-1-pyridazin-3-ylpyrrolidin-3-yl]amino]-1,3,4-thiadiazol-2-yl]acetamide;

(2S)-2-Methoxy-2-phenyl-N-[5-[[(3R)-1-(1,2,4-triazin-6-yl)pyrrolidin-3-yl]amino]-1,3,4-thiadiazol-2-yl]acetamide;

(2S)-2-Methoxy-2-(3-methoxyphenyl)-N-[5-[[(3R)-1-(1,2,4-triazin-3-yl)pyrrolidin-3-yl]amino]-1,3,4-thiadiazol-2-yl]acetamide;

(2S)-2-Methoxy-2-(3-methoxyphenyl)-N-[5-[[(3R)-1-pyridazin-3-ylpyrrolidin-3-yl]amino]-1,3,4-thiadiazol-2-yl]acetamide;

(2S)-2-[3-(Difluoromethoxy)phenyl]-2-methoxy-N-[5-[[(3R)-1-(1,2,4-triazin-3-yl)pyrrolidin-3-yl]amino]-1,3,4-thiadiazol-2-yl]acetamide;

(2S)-2-[3-(Difluoromethoxy)phenyl]-2-methoxy-N-[5-[[(3R)-1-pyridazin-3-ylpyrrolidin-3-yl]amino]-1,3,4-thiadiazol-2-yl]acetamide;

(2S)-2-Methoxy-N-[5-[[(3R)-1-(1,2,4-triazin-3-yl)pyrrolidin-3-yl]amino]-1,3,4-thiadiazol-2-yl]-2-[3-(trifluoromethoxy)phenyl]acetamide;

(2S)-2-Methoxy-N-[5-[[(3R)-1-pyridazin-3-ylpyrrolidin-3-yl]amino]-1,3,4-thiadiazol-2-yl]-2-[3-(trifluoromethoxy)phenyl]acetamide;

(2S)-2-Ethoxy-2-phenyl-N-[5-[[(3R)-1-pyridazin-3-ylpyrrolidin-3-yl]amino]-1,3,4-thiadiazol-2-yl]acetamide;

(2S)-2-Methoxy-2-(4-methoxyphenyl)-N-[5-[[(3R)-1-pyridazin-3-ylpyrrolidin-3-yl]amino]-1,3,4-thiadiazol-2-yl]acetamide; and (2S)-2-(4-Fluorophenyl)-2-methoxy-N-[5-[[(3R)-1-pyridazin-3-ylpyrrolidin-3-yl]amino]-1,3,4-thiadiazol-2-yl]acetamide.

In one embodiment there is provided (2S)-2-methoxy-2-(3-methoxyphenyl)-N-[5-[[(3R)-1-(1,2,4-triazin-3-yl)pyrrolidin-3-yl]amino]-1,3,4-thiadiazol-2-yl]acetamide, or a pharmaceutically acceptable salt thereof.

In one embodiment there is provided (2S)-2-methoxy-2-(3-methoxyphenyl)-N-[5-[[(3R)-1-(1,2,4-triazin-3-yl)pyrrolidin-3-yl]amino]-1,3,4-thiadiazol-2-yl]acetamide.

In one embodiment there is provided a pharmaceutically acceptable salt of (2S)-2-methoxy-2-(3-methoxyphenyl)-N-[5-[[(3R)-1-(1,2,4-triazin-3-yl)pyrrolidin-3-yl]amino]-1,3,4-thiadiazol-2-yl]acetamide.

In one embodiment there is provided (2S)-2-methoxy-2-phenyl-N-[5-[[(3R)-1-pyridazin-3-ylpyrrolidin-3-yl]amino]-1,3,4-thiadiazol-2-yl]acetamide, or a pharmaceutically acceptable salt thereof.

In one embodiment there is provided (2S)-2-methoxy-2-phenyl-N-[5-[[(3R)-1-pyridazin-3-ylpyrrolidin-3-yl]amino]-1,3,4-thiadiazol-2-yl]acetamide.

In one embodiment there is provided a pharmaceutically acceptable salt of (2S)-2-methoxy-2-phenyl-N-[5-[[(3R)-1-pyridazin-3-ylpyrrolidin-3-yl]amino]-1,3,4-thiadiazol-2-yl]acetamide.

In one embodiment there is provided (2S)-2-methoxy-2-(3-methoxyphenyl)-N-[5-[[(3R)-1-pyridazin-3-ylpyrrolidin-3-yl]amino]-1,3,4-thiadiazol-2-yl]acetamide, or a pharmaceutically acceptable salt thereof.

In one embodiment there is provided (2S)-2-methoxy-2-(3-methoxyphenyl)-N-[5-[[(3R)-1-pyridazin-3-ylpyrrolidin-3-yl]amino]-1,3,4-thiadiazol-2-yl]acetamide.

In one embodiment there is provided a pharmaceutically acceptable salt of provided (2S)-2-methoxy-2-(3-methoxyphenyl)-N-[5-[[(3R)-1-pyridazin-3-ylpyrrolidin-3-yl]amino]-1,3,4-thiadiazol-2-yl]acetamide.

In one embodiment there is provided (2S)-2-[3-(difluoromethoxy)phenyl]-2-methoxy-N-[5-[[(3R)-1-pyridazin-3-ylpyrrolidin-3-yl]amino]-1,3,4-thiadiazol-2-yl]acetamide, or a pharmaceutically acceptable salt thereof.

In one embodiment there is provided (2S)-2-[3-(difluoromethoxy)phenyl]-2-methoxy-N-[5-[[(3R)-1-pyridazin-3-ylpyrrolidin-3-yl]amino]-1,3,4-thiadiazol-2-yl]acetamide.

In one embodiment there is provided a pharmaceutically acceptable salt of (2S)-2-[3-(difluoromethoxy)phenyl]-2-methoxy-N-[5-[[(3R)-1-pyridazin-3-ylpyrrolidin-3-yl]amino]-1,3,4-thiadiazol-2-yl]acetamide.

In one embodiment there is provided (2S)-2-ethoxy-2-phenyl-N-[5-[[(3R)-1-pyridazin-3-ylpyrrolidin-3-yl]amino]-1,3,4-thiadiazol-2-yl]acetamide, or a pharmaceutically acceptable salt thereof.

In one embodiment there is provided (2S)-2-ethoxy-2-phenyl-N-[5-[[(3R)-1-pyridazin-3-ylpyrrolidin-3-yl]amino]-1,3,4-thiadiazol-2-yl]acetamide.

In one embodiment there is provided a pharmaceutically acceptable salt of (2S)-2-ethoxy-2-phenyl-N-[5-[[(3R)-1-pyridazin-3-ylpyrrolidin-3-yl]amino]-1,3,4-thiadiazol-2-yl]acetamide.

In one embodiment there is provided (2S)-2-methoxy-2-(4-methoxyphenyl)-N-[5-[[(3R)-1-pyridazin-3-ylpyrrolidin-3-yl]amino]-1,3,4-thiadiazol-2-yl]acetamide, or a pharmaceutically acceptable salt thereof.

In one embodiment there is provided (2S)-2-methoxy-2-(4-methoxyphenyl)-N-[5-[[(3R)-1-pyridazin-3-ylpyrrolidin-3-yl]amino]-1,3,4-thiadiazol-2-yl]acetamide.

In one embodiment there is provided a pharmaceutically acceptable salt of (2S)-2-methoxy-2-(4-methoxyphenyl)-N-[5-[[(3R)-1-pyridazin-3-ylpyrrolidin-3-yl]amino]-1,3,4-thiadiazol-2-yl]acetamide.

In one embodiment there is provided (2S)-2-(4-fluorophenyl)-2-methoxy-N-[5-[[(3R)-1-pyridazin-3-ylpyrrolidin-3-yl]amino]-1,3,4-thiadiazol-2-yl]acetamide, or a pharmaceutically acceptable salt thereof.

In one embodiment there is provided (2S)-2-(4-fluorophenyl)-2-methoxy-N-[5-[[(3R)-1-pyridazin-3-ylpyrrolidin-3-yl]amino]-1,3,4-thiadiazol-2-yl]acetamide.

In one embodiment there is provided a pharmaceutically acceptable salt of (2S)-2-(4-fluorophenyl)-2-methoxy-N-[5-[[(3R)-1-pyridazin-3-ylpyrrolidin-3-yl]amino]-1,3,4-thiadiazol-2-yl]acetamide.

Compounds and salts described in this specification may exist in solvated forms and unsolvated forms. For example, a solvated form may be a hydrated form, such as a hemi-hydrate, a mono-hydrate, a di-hydrate, a tri-hydrate or an alternative quantity thereof. The present invention encompasses all such solvated and unsolvated forms of compounds of Formula (I), (IA) or (IB) or pharmaceutically acceptable salts of any of these compounds.

Atoms of the compounds and salts described in this specification may exist as their isotopes. The present invention encompasses all compounds of Formula (I), (IA) or (IB) or pharmaceutically acceptable salts of any of these compounds where an atom is replaced by one or more of its isotopes (for example a compound of Formula (I), (IA) or (IB) or a pharmaceutically acceptable salt of any of these compounds where one or more carbon atom is an $^{11}C$ or $^{13}C$ carbon isotope, or where one or more hydrogen atoms is an $^{18}F$ isotope, or where one or more hydrogen atoms is a $^{2}H$ (deuterium) or $^{3}H$ (tritium) isotope).

Compounds and salts described in this specification may exist as a mixture of tautomers. "Tautomers" are structural isomers that exist in equilibrium resulting from the migration of a hydrogen atom. The present invention includes all tautomers of compounds of Formula (I), (IA) or (IB) or pharmaceutically acceptable salts of any of these compounds.

Compounds of Formula (I), (IA) and (IB) and pharmaceutically acceptable salts of any of these compounds exist as diastereomers by virtue of their asymmetric carbon atoms.

In one embodiment there is provided a compound of Formula (I), or a pharmaceutically acceptable salt thereof, which is in a diastereomeric excess (% de) of ≥95%, ≥98% or ≥99%. In one embodiment, the compound of Formula (I) or a pharmaceutically acceptable salt thereof is present in diastereomeric excess (% de) of ≥99%. In one embodiment there is provided a compound of Formula (IA), or a pharmaceutically acceptable salt thereof, which is in a diastereomeric excess (% de) of ≥95%, ≥98% or ≥99%. In one embodiment, the compound of Formula (IA) or a pharmaceutically acceptable salt thereof is present in diastereomeric excess (% de) of ≥99%. In one embodiment there is provided a compound of Formula (IB), or a pharmaceutically acceptable salt thereof, which is in a diastereomeric excess (% de) of ≥95%, ≥98% or ≥99%. In one embodiment, the compound of Formula (IB) or a pharmaceutically acceptable salt thereof is present in diastereomeric excess (% de) of ≥99%.

Compounds and salts described in this specification may be crystalline, and may exhibit one or more crystalline forms. The invention includes any such crystalline form of a compound of Formula (I), (IA) or (IB) or pharmaceutically acceptable salts of any of these compounds. It is generally known that crystalline materials may be characterised using conventional techniques such as X-Ray Powder Diffraction (XRPD), Differential Scanning Calorimetry (DSC), Thermal Gravimetric Analysis (TGA), Diffuse Reflectance Infrared Fourier Transform (DRIFT) spectroscopy, Near Infrared (NIR) spectroscopy, solution and/or solid state nuclear magnetic resonance spectroscopy. The water content of such crystalline materials may be determined by Karl Fischer analysis.

The specific solid forms described herein provide XRPD patterns substantially the same as the XRPD patterns shown in the Figures, and have the various 2-theta values as shown in the Tables included herein. One skilled in the art will understand that an XRPD pattern or diffractogram may be obtained which has one or more measurement errors depending on the recording conditions, such as the equipment or machine used. Similarly, it is generally known that intensities in an XRPD pattern may fluctuate depending on measurement conditions or sample preparation as a result of preferred orientation. Relative intensity of peaks can also be affected by, for example, grains above 30 μm in size and non-unitary aspect ratios. The skilled person understands that the position of reflections can be affected by the precise height at which the sample sits in the diffractometer, and also the zero calibration of the diffractometer. The surface planarity of the sample may also have a small effect.

As a result of these considerations, the diffraction pattern data presented are not to be taken as absolute values (Jenkins, R & Snyder, R. L. '*Introduction to X-Ray Powder Diffractometry*' John Wiley & Sons 1996; Bunn, C. W. (1948), '*Chemical Crystallography*', Clarendon Press, London; Klug, H. P. & Alexander, L. E. (1974), '*X-Ray Diffraction Procedures*'). It should correspondingly be understood that the solid forms of the present invention are not limited to the crystals that provide XRPD patterns that are identical to the XRPD pattern shown in the Figures, and any crystals providing XRPD patterns substantially the same as those shown in the Figures fall within the scope of the present invention. A person skilled in the art of XRPD is able to judge the substantial identity of XRPD patterns. Generally, a measurement error of a diffraction angle in an XRPD is approximately plus or minus 0.2° 2-theta, and such degree of a measurement error should be taken into account when considering the X-ray powder diffraction pattern in the Figures and when reading data contained in the Tables included herein.

The compound of Example 2 exhibits crystalline properties, and one crystalline form has been characterised herein.

Therefore, in one embodiment there is provided Form D of (2S)-2-methoxy-2-phenyl-N-[5-[[(3R)-1-pyridazin-3-ylpyrrolidin-3-yl]amino]-1,3,4-thiadiazol-2-yl]acetamide.

In one embodiment there is provided a crystalline form, Form D of (2S)-2-methoxy-2-phenyl-N-[5-[[(3R)-1-pyridazin-3-ylpyrrolidin-3-yl]amino]-1,3,4-thiadiazol-2-yl] acetamide, which has an X-ray powder diffraction pattern with at least one specific peak at about 2-theta=7.9°.

In one embodiment there is provided a crystalline form, Form D of (2S)-2-methoxy-2-phenyl-N-[5-[[(3R)-1-pyridazin-3-ylpyrrolidin-3-yl]amino]-1,3,4-thiadiazol-2-yl] acetamide, which has an X-ray powder diffraction pattern with at least one specific peak at about 2-theta=19.3°.

In one embodiment there is provided a crystalline form, Form D of (2S)-2-methoxy-2-phenyl-N-[5-[[(3R)-1-pyridazin-3-ylpyrrolidin-3-yl]amino]-1,3,4-thiadiazol-2-yl] acetamide, which has an X-ray powder diffraction pattern with at least two specific peaks at about 2-theta=7.9 and 19.3°.

In one embodiment there is provided a crystalline form, Form D of (2S)-2-methoxy-2-phenyl-N-[5-[[(3R)-1-pyridazin-3-ylpyrrolidin-3-yl]amino]-1,3,4-thiadiazol-2-yl] acetamide, which has an X-ray powder diffraction pattern with specific peaks at about 2-theta=7.9, 8.3, 14.6, 18.4, 18.9, 19.3, 21.2, 24.4, 24.6 and 25.3°.

In one embodiment there is provided a crystalline form, Form D of (2S)-2-methoxy-2-phenyl-N-[5-[[(3R)-1-pyridazin-3-ylpyrrolidin-3-yl]amino]-1,3,4-thiadiazol-2-yl] acetamide which has an X-ray powder diffraction pattern substantially the same as the X-ray powder diffraction pattern shown in FIG. 1.

In one embodiment there is provided a crystalline form, Form D of (2S)-2-methoxy-2-phenyl-N-[5-[[(3R)-1-pyridazin-3-ylpyrrolidin-3-yl]amino]-1,3,4-thiadiazol-2-yl] acetamide, which has an X-ray powder diffraction pattern with at least one specific peak at 2-theta=7.9° plus or minus 0.2° 2-theta.

In one embodiment there is provided a crystalline form, Form D of (2S)-2-methoxy-2-phenyl-N-[5-[[(3R)-1-pyridazin-3-ylpyrrolidin-3-yl]amino]-1,3,4-thiadiazol-2-yl] acetamide, which has an X-ray powder diffraction pattern with at least one specific peak at 2-theta=19.3° plus or minus 0.2° 2-theta.

In one embodiment there is provided a crystalline form, Form D of (2S)-2-methoxy-2-phenyl-N-[5-[[(3R)-1-pyridazin-3-ylpyrrolidin-3-yl]amino]-1,3,4-thiadiazol-2-yl] acetamide, which has an X-ray powder diffraction pattern with at least two specific peaks at 2-theta=7.9 and 19.3° plus or minus 0.2° 2-theta.

In one embodiment there is provided a crystalline form, Form D of (2S)-2-methoxy-2-phenyl-N-[5-[[(3R)-1-pyridazin-3-ylpyrrolidin-3-yl]amino]-1,3,4-thiadiazol-2-yl] acetamide, which has an X-ray powder diffraction pattern with specific peaks at 2-theta=7.9, 8.3, 14.6, 18.4, 18.9, 19.3, 21.2, 24.4, 24.6 and 25.3° plus or minus 0.2° 2-theta.

In one embodiment there is provided a crystalline form, Form D of (2S)-2-methoxy-2-phenyl-N-[5-[[(3R)-1-pyridazin-3-ylpyrrolidin-3-yl]amino]-1,3,4-thiadiazol-2-yl] acetamide, which has an X-ray powder diffraction pattern substantially the same as the X-ray powder diffraction pattern shown in FIG. 1.

It is to be understood that given the errors in 2-theta values it may occur that two close peaks may coalesce to form one peak under certain conditions. For example, in the characterizing X-ray powder diffraction patterns above the peaks at 7.9 and 8.3° 2-theta and the peaks at 18.9 and 19.3° 2-theta may overlap under certain conditions. Therefore, the apparent absence of a peak is not to be automatically construed as a lack of substantial identity.

When it is stated that an embodiment relates to a crystalline form, the degree of crystallinity may be greater than about 60%. In some embodiments the degree of crystallinity is greater than about 80%. In some embodiments the degree of crystallinity is greater than about 90%. In some embodiments the degree of crystallinity is greater than about 95%. In some embodiments the degree of crystallinity is greater than about 98%.

Compounds of Formula (I) may for example be prepared by the reaction of a compound of Formula (II):

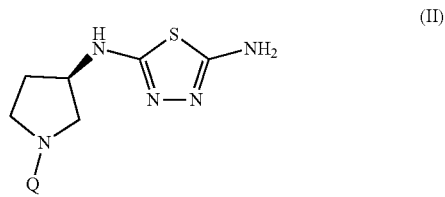

(II)

Where Q is as defined in any of the embodiments herein (for example as defined in any of the Q definitions listed under bullet points (a)-(s) hereinabove), with a compound of formula (III):

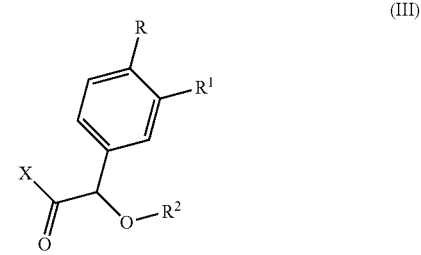

(III)

Where R, $R^1$ and $R^2$ are as defined in any of the embodiments herein (for example as defined in any of the R, $R^1$, and $R^2$ definitions listed under bullet points (a)-(s) hereinabove) and X is a leaving group, such as a halogen atom (for example a chlorine atom) or a hydroxy group. The reaction is conveniently performed in a suitable solvent (for example N,N-dimethylformamide or N,N-dimethylacetamide) and in the presence of a base (for example di-isopropyl ethylamine) at a suitable temperature (for example at room temperature (around 20 to 30° C.) or at elevated temperature, such as between 80 and 120° C., conveniently at around 100° C. Where X is a hydroxy group, a suitable coupling agent (for example HATU) is used to form the amide bond.

Compounds of Formula (III), and salts thereof, are therefore useful as intermediates in the preparation of the compounds of Formula (I) and provide a further embodiment.

In one embodiment there is provided a compound of Formula (III), or a salt thereof, where:
R is hydro;
$R^1$ is difluoromethoxy or trifluoromethoxy;
$R^2$ is methyl or ethyl; and
X is a leaving group. In one embodiment X is hydroxy or chloro. In one embodiment X is hydroxy.

In one embodiment there is provided 2-[3-(difluoromethoxy)phenyl]-2-methoxyacetic acid, or a salt thereof.

In one embodiment there is provided 2-methoxy-2-[3-(trifluoromethoxy)phenyl]acetic acid, or a salt thereof.

In one embodiment there is provided 2-Ethoxy-2-(4-fluorophenyl)acetic acid, or a salt thereof.

In one embodiment there is provided 2-(4-Fluoro-3-methoxy-phenyl)-2-methoxy-acetic acid, or a salt thereof.

In one embodiment there is provided 2-[3-(Difluoromethoxy)phenyl]-2-ethoxy-acetic acid, or a salt thereof.

In one embodiment there is provided 2-Ethoxy-2-[3-(trifluoromethoxy)phenyl]acetic acid, or a salt thereof.

In one embodiment there is provided 2-[3-(difluoromethoxy)phenyl]-2-methoxyacetic acid.

In one embodiment there is provided 2-methoxy-2-[3-(trifluoromethoxy)phenyl]acetic acid.

In one embodiment there is provided 2-Ethoxy-2-(4-fluorophenyl)acetic acid.

In one embodiment there is provided 2-(4-Fluoro-3-methoxy-phenyl)-2-methoxy-acetic acid.

In one embodiment there is provided 2-[3-(Difluoromethoxy)phenyl]-2-ethoxy-acetic acid.

In one embodiment there is provided 2-Ethoxy-2-[3-(trifluoromethoxy)phenyl]acetic acid.

Compounds of formula (II) and formula (III) can be prepared by methods similar to those shown in the Examples section.

A suitable salt of a compound of Formula (III) is a base-addition salt. A base addition salt of a compound of Formula (III) may be formed by bringing the compound into contact with a suitable inorganic or organic base under conditions known to the skilled person. Such conditions need not generate pharmaceutically acceptable salts. A base addition salt may for example be formed using an inorganic base selected from the group consisting of an alkali metal hydroxide (such as sodium, potassium, or lithium hydroxide) or an alkaline earth metal hydroxide (such as calcium hydroxide or magnesium hydroxide). A base addition salt may also be formed using an organic base selected from the group consisting of methylamine, dimethylamine, trimethylamine, piperidine, morpholine and tris-(2-hydroxyethyl) amine.

Therefore, in one embodiment there is provided a compound of Formula (III) or a salt thereof, where the salt is a sodium hydroxide, potassium hydroxide, lithium hydroxide, calcium hydroxide, magnesium hydroxide, methylamine, dimethylamine, trimethylamine, piperidine, morpholine or tris-(2-hydroxyethyl)amine salt.

As a result of their GLS1 inhibitory activity, the compounds of Formula (I), (IA) and (IB) and pharmaceutically acceptable salts of any of these compounds are expected to be useful in therapy, for example in the treatment of diseases or medical conditions mediated at least in part by GLS1, including cancer.

Where "cancer" is mentioned, this includes both non-metastatic cancer and also metastatic cancer, such that treating cancer involves treatment of both primary tumours and also tumour metastases.

In any embodiment where cancer is mentioned in a general sense the following embodiments may apply:

In one embodiment the cancer is breast cancer. In one embodiment the cancer is triple negative breast cancer.

"Triple negative breast cancer" is any breast cancer that does not express the genes for the oestrogen receptor, progesterone receptor and Her2/neu.

In one embodiment the cancer is hepatocellular carcinoma.

In one embodiment the cancer is lung cancer. In one embodiment the lung cancer is small cell lung cancer. In one embodiment the lung cancer is non-small cell lung cancer.

In one embodiment the cancer is pancreatic cancer.

In one embodiment the cancer is bladder cancer.

In one embodiment the cancer is metastatic cancer.

In one embodiment the cancer is non-metastatic cancer.

"GLS1 inhibitory activity" refers to a decrease in the activity of GLS1 as a direct or indirect response to the presence of a compound of Formula (I), (IA) or (IB) or a pharmaceutically acceptable salt of any of these compounds, relative to the activity of GLS1 in the absence of compound of Formula (I), (IA) or (IB) or a pharmaceutically acceptable salt of any of these compounds. Such a decrease in activity may be due to the direct interaction of the compound of Formula (I), (IA) or (IB) or a pharmaceutically acceptable salt of any of these compounds with GLS1, or due to the interaction of the compound of Formula (I), (IA) or (IB) or a pharmaceutically acceptable salt of any of these compounds with one or more other factors that in turn affect GLS1 activity. For example, the compound of Formula (I), (IA) or (IB) or a pharmaceutically acceptable salt of any of these compounds may decrease GLS1 by directly binding to GLS1, by causing (directly or indirectly) another factor to decrease GLS1 activity, or by (directly or indirectly) decreasing the amount of GLS1 present in the cell or organism.

The term "therapy" is intended to have its normal meaning of dealing with a disease in order to entirely or partially relieve one, some or all of its symptoms, or to correct or compensate for the underlying pathology. The term "therapy" also includes "prophylaxis" unless there are specific indications to the contrary. The terms "therapeutic" and "therapeutically" should be interpreted in a corresponding manner.

The term "prophylaxis" is intended to have its normal meaning and includes primary prophylaxis to prevent the development of the disease and secondary prophylaxis whereby the disease has already developed and the patient is temporarily or permanently protected against exacerbation or worsening of the disease or the development of new symptoms associated with the disease.

The term "treatment" is used synonymously with "therapy". Similarly the term "treat" can be regarded as applying therapy where "therapy" is as defined herein.

In one embodiment there is provided a compound of Formula (I), or a pharmaceutically acceptable salt thereof, for use in therapy. In one embodiment there is provided a compound of Formula (IA), or a pharmaceutically acceptable salt thereof, for use in therapy. In one embodiment there is provided a compound of Formula (IB), or a pharmaceutically acceptable salt thereof, for use in therapy.

In one embodiment there is provided the use of the compound of Formula (I), or a pharmaceutically acceptable salt thereof, for the manufacture of a medicament. In one embodiment there is provided the use of the compound of Formula (IA), or a pharmaceutically acceptable salt thereof, for the manufacture of a medicament. In one embodiment there is provided the use of the compound of Formula (IB), or a pharmaceutically acceptable salt thereof, for the manufacture of a medicament.

In one embodiment there is provided a compound of Formula (I), or a pharmaceutically acceptable salt thereof, for use in the treatment of a disease mediated by GLS1. In one embodiment, said disease mediated by GLS1 is cancer. In one embodiment, said cancer is selected from the group consisting of breast cancer (for example triple negative breast cancer), lung cancer (for example non-small cell lung cancer), pancreatic cancer, bladder cancer and hepatocellular carcinoma. In one embodiment there is provided a compound of Formula (IA), or a pharmaceutically acceptable salt thereof, for use in the treatment of a disease mediated by GLS1. In one embodiment, said disease mediated by GLS1 is cancer. In one embodiment, said cancer is selected from the group consisting of breast cancer (for example triple negative breast cancer), lung cancer (for example non-small cell lung cancer), pancreatic cancer, bladder cancer and hepatocellular carcinoma. In one embodiment there is provided a compound of Formula (IB), or a pharmaceutically acceptable salt thereof, for use in the treatment of a disease mediated by GLS1. In one embodiment, said disease mediated by GLS1 is cancer. In one embodiment, said cancer is selected from the group consisting of breast cancer (for example triple negative breast cancer), lung cancer (for example non-small cell lung cancer), pancreatic cancer, bladder cancer and hepatocellular carcinoma.

In one embodiment there is provided a compound of Formula (I), or a pharmaceutically acceptable salt thereof, for use in the treatment of cancer. In one embodiment there is provided a compound of Formula (IA), or a pharmaceutically acceptable salt thereof, for use in the treatment of cancer. In one embodiment there is provided a compound of Formula (IB), or a pharmaceutically acceptable salt thereof, for use in the treatment of cancer.

In one embodiment there is provided the use of the compound of Formula (I), or a pharmaceutically acceptable salt thereof, for the manufacture of a medicament for the treatment of a disease mediated by GLS1. In one embodiment, said disease mediated by GLS1 is cancer. In one embodiment, said cancer is selected from the group consisting of breast cancer (for example triple negative breast cancer), lung cancer (for example non-small cell lung cancer), pancreatic cancer, bladder cancer and hepatocellular carcinoma. In one embodiment there is provided the use of the compound of Formula (IA), or a pharmaceutically acceptable salt thereof, for the manufacture of a medicament for the treatment of a disease mediated by GLS1. In one embodiment, said disease mediated by GLS1 is cancer. In one embodiment, said cancer is selected from the group consisting of breast cancer (for example triple negative breast cancer), lung cancer (for example non-small cell lung cancer), bladder cancer, pancreatic cancer, bladder cancer and hepatocellular carcinoma. In one embodiment there is provided the use of the compound of Formula (IB), or a pharmaceutically acceptable salt thereof, for the manufacture of a medicament for the treatment of a disease mediated by GLS1. In one embodiment, said disease mediated by GLS1 is cancer. In one embodiment, said cancer is selected from the group consisting of breast cancer (for example triple negative breast cancer), lung cancer (for example non-small cell lung cancer), pancreatic cancer, bladder cancer and hepatocellular carcinoma.

In one embodiment there is provided the use of the compound of Formula (I), or a pharmaceutically acceptable salt thereof, for the manufacture of a medicament for the treatment of cancer. In one embodiment there is provided the use of the compound of Formula (IA), or a pharmaceutically acceptable salt thereof, for the manufacture of a medicament for the treatment of cancer. In one embodiment there is provided the use of the compound of Formula (IB), or a pharmaceutically acceptable salt thereof, for the manufacture of a medicament for the treatment of cancer.

In one embodiment there is provided a method for treating a disease in which inhibition of GLS1 is beneficial in a warm-blooded animal in need of such treatment, which comprises administering to said warm-blooded animal a therapeutically effective amount of a compound of Formula (I), or a pharmaceutically acceptable salt thereof. In one embodiment there is provided a method for treating a disease in which inhibition of GLS1 is beneficial in a warm-blooded animal in need of such treatment, which comprises administering to said warm-blooded animal a therapeutically effective amount of a compound of Formula (IA), or a pharmaceutically acceptable salt thereof. In one embodiment there is provided a method for treating a disease in which inhibition of GLS1 is beneficial in a warm-blooded animal in need of such treatment, which comprises administering to said warm-blooded animal a therapeutically effective amount of a compound of Formula (IB), or a pharmaceutically acceptable salt thereof.

The term "therapeutically effective amount" refers to an amount of a compound of Formula (I), (IA) or (IB) or a pharmaceutically acceptable salt of any of these compounds as described in any of the embodiments herein which is effective to provide "therapy" in a subject, or to "treat" a disease or disorder in a subject. In the case of cancer, the therapeutically effective amount may cause any of the changes observable or measurable in a subject as described in the definition of "therapy", "treatment" and "prophylaxis" above. For example, the effective amount can reduce the number of cancer or tumour cells; reduce the overall tumour size; inhibit or stop tumour cell infiltration into peripheral organs including, for example, the soft tissue and bone; inhibit and stop tumour metastasis; inhibit and stop tumour growth; relieve to some extent one or more of the symptoms associated with the cancer; reduce morbidity and mortality; improve quality of life; or a combination of such effects. An effective amount may be an amount sufficient to decrease the symptoms of a disease responsive to inhibition of GLS1 activity. For cancer therapy, efficacy in-vivo can, for example, be measured by assessing the duration of survival, time to disease progression (TTP), the response rates (RR), duration of response, and/or quality of life. As recognized by those skilled in the art, effective amounts may vary depending on route of administration, excipient usage, and co-usage with other agents. For example, where a combination therapy is used, the amount of the compound of formula (I), (IA) or (IB) or pharmaceutically acceptable salt of any of these compounds described in this specification and the amount of the other pharmaceutically active agent(s) are, when combined, jointly effective to treat a targeted disorder in the animal patient. In this context, the combined amounts are in a "therapeutically effective amount" if they are, when combined, sufficient to decrease the symptoms of a disease responsive to inhibition of GLS1 activity as described above. Typically, such amounts may be determined by one skilled in the art by, for example, starting with the dosage range described in this specification for the compound of formula (I), (IA) or (IB) pharmaceutically acceptable salt of any of these compounds and an approved or otherwise published dosage range(s) of the other pharmaceutically active compound(s).

"Warm-blooded animals" include, for example, humans.

In one embodiment there is provided a method for treating cancer in a warm-blooded animal in need of such treatment, which comprises administering to said warm-blooded animal a therapeutically effective amount of a compound of Formula (I), or a pharmaceutically acceptable salt thereof. In one embodiment there is provided a method for treating cancer in a warm-blooded animal in need of such treatment, which comprises administering to said warm-blooded animal a therapeutically effective amount of a compound of Formula (IA), or a pharmaceutically acceptable salt thereof. In one embodiment there is provided a method for treating cancer in a warm-blooded animal in need of such treatment, which comprises administering to said warm-blooded animal a therapeutically effective amount of a compound of Formula (IB), or a pharmaceutically acceptable salt thereof. In one embodiment, said cancer is selected from the group consisting of breast cancer (for example triple negative breast cancer), lung cancer (for example non-small cell lung cancer), pancreatic cancer, bladder cancer and hepatocellular carcinoma.

The anti-cancer treatment described in this specification may be applied as a sole therapy, or may involve, in addition to administration of the compound of Formula (I), (IA) or (IB) or a pharmaceutically acceptable salt of any of these compounds, conventional surgery, radiotherapy or chemotherapy; or a combination of such additional therapies. Such conventional surgery, radiotherapy or chemotherapy may be administered simultaneously, sequentially or separately to treatment with the compound of Formula (I), (IA) or (IB) or a pharmaceutically acceptable salt of any of these compounds.

Therefore, in one embodiment there is provided a compound of Formula (I), or a pharmaceutically acceptable salt thereof, and at least one additional anti-tumour substance, for use in the treatment of cancer. Therefore, in one embodiment there is provided a compound of Formula (IA), or a pharmaceutically acceptable salt thereof, and at least one additional anti-tumour substance, for use in the treatment of cancer. Therefore, in one embodiment there is provided a compound of Formula (IB), or a pharmaceutically acceptable salt thereof, and at least one additional anti-tumour substance, for use in the treatment of cancer.

In one embodiment there is provided a compound of Formula (I), or a pharmaceutically acceptable salt thereof, and at least one additional anti-tumour substance for use in the simultaneous, separate or sequential treatment of cancer. In one embodiment there is provided a compound of Formula (IA), or a pharmaceutically acceptable salt thereof, and at least one additional anti-tumour substance for use in the simultaneous, separate or sequential treatment of cancer. In one embodiment there is provided a compound of Formula (IB), or a pharmaceutically acceptable salt thereof, and at least one additional anti-tumour substance for use in the simultaneous, separate or sequential treatment of cancer.

In one embodiment there is provided a compound of Formula (I), or a pharmaceutically acceptable salt thereof, for use in the treatment of cancer, where the compound of Formula (I) is administered simultaneously, separately or sequentially with at least one additional anti-tumour substance. In one embodiment there is provided a compound of Formula (IA), or a pharmaceutically acceptable salt thereof, for use in the treatment of cancer, where the compound of Formula (IA) is administered simultaneously, separately or sequentially with at least one additional anti-tumour substance. In one embodiment there is provided a compound of Formula (IB), or a pharmaceutically acceptable salt thereof, for use in the treatment of cancer, where the compound of Formula (IB) is administered simultaneously, separately or sequentially with at least one additional anti-tumour substance.

In one embodiment there is provided a method of treating cancer in a warm-blooded animal who is in need of such treatment, which comprises administering to said warm-blooded animal a compound of Formula (I), or a pharmaceutically acceptable salt thereof and at least one additional anti-tumour substance, wherein the amounts of the compound of Formula (I), or a pharmaceutically acceptable salt thereof, and the additional anti-tumour substance are jointly effective in producing an anti-cancer effect. In one embodiment there is provided a method of treating cancer in a warm-blooded animal who is in need of such treatment, which comprises administering to said warm-blooded animal a compound of Formula (IA), or a pharmaceutically acceptable salt thereof and at least one additional anti-tumour substance, wherein the amounts of the compound of Formula (IA), or a pharmaceutically acceptable salt thereof, and the additional anti-tumour substance are jointly effective in producing an anti-cancer effect. In one embodiment there is provided a method of treating cancer in a warm-blooded animal who is in need of such treatment, which comprises administering to said warm-blooded animal a compound of Formula (IB), or a pharmaceutically acceptable salt thereof and at least one additional anti-tumour substance, wherein the amounts of the compound of Formula (IB), or a pharmaceutically acceptable salt thereof, and the additional anti-tumour substance are jointly effective in producing an anti-cancer effect.

In one embodiment there is provided a method of treating cancer in a warm-blooded animal who is in need of such treatment, which comprises administering to said warm-blooded animal a compound of Formula (I), or a pharmaceutically acceptable salt thereof, and simultaneously, separately or sequentially administering at least one additional anti-tumour substance to said warm-blooded animal, wherein the amounts of the compound of Formula (I), or pharmaceutically acceptable salt thereof, and the additional anti-tumour substance are jointly effective in producing an anti-cancer effect. In one embodiment there is provided a method of treating cancer in a warm-blooded animal who is in need of such treatment, which comprises administering to said warm-blooded animal a compound of Formula (IA), or a pharmaceutically acceptable salt thereof, and simultaneously, separately or sequentially administering at least one additional anti-tumour substance to said warm-blooded animal, wherein the amounts of the compound of Formula (IA), or pharmaceutically acceptable salt thereof, and the additional anti-tumour substance are jointly effective in producing an anti-cancer effect. In one embodiment there is provided a method of treating cancer in a warm-blooded animal who is in need of such treatment, which comprises administering to said warm-blooded animal a compound of Formula (IB), or a pharmaceutically acceptable salt thereof, and simultaneously, separately or sequentially administering at least one additional anti-tumour substance to said warm-blooded animal, wherein the amounts of the compound of Formula (IB), or pharmaceutically acceptable salt thereof, and the additional anti-tumour substance are jointly effective in producing an anti-cancer effect.

In any embodiment the additional anti-tumour substance is a taxane. In one embodiment the taxane is paclitaxel. In one embodiment the taxane is docetaxel (for example Taxotere®).

In any embodiment the additional anti-tumour substance is a platinum therapy. In one embodiment the platinum therapy is cisplatin, oxaliplatin, or carboplatin.

In any embodiment the additional anti-tumour substance is permetrexed.

In one embodiment there is provided a compound of Formula (I), or a pharmaceutically acceptable salt thereof, for use in the treatment of cancer, where the compound of Formula (I), or a pharmaceutically acceptable salt thereof is administered in combination with cisplatin, permetrexed or docetaxel. In one embodiment there is provided a compound of Formula (I), or a pharmaceutically acceptable salt thereof, for use in the treatment of cancer, where the compound of Formula (I), or a pharmaceutically acceptable salt thereof is administered in combination with cisplatin. In one embodiment there is provided a compound of Formula (I), or a pharmaceutically acceptable salt thereof, for use in the treatment of cancer, where the compound of Formula (I), or a pharmaceutically acceptable salt thereof is administered in combination with permetrexed. In one embodiment there is provided a compound of Formula (I), or a pharmaceutically acceptable salt thereof, for use in the treatment of cancer, where the compound of Formula (I), or a pharmaceutically acceptable salt thereof is administered in combination with docetaxel.

In one embodiment there is provided a pharmaceutical composition comprising a compound of Formula (I) and at least one additional anti-tumour substance. In one embodiment the pharmaceutical composition also comprises at least one pharmaceutically acceptable diluent or carrier. In one embodiment there is provided a pharmaceutical composition comprising a compound of Formula (IA) and at least one additional anti-tumour substance. In one embodiment the pharmaceutical composition also comprises at least one pharmaceutically acceptable diluent or carrier. In one embodiment there is provided a pharmaceutical composition comprising a compound of Formula (IB) and at least one additional anti-tumour substance. In one embodiment the pharmaceutical composition also comprises at least one pharmaceutically acceptable diluent or carrier.

In one embodiment there is provided a pharmaceutical composition comprising a compound of Formula (I) and at least one additional anti-tumour substance, for use in the treatment of cancer. In one embodiment the pharmaceutical composition also comprises at least one pharmaceutically acceptable diluent or carrier. In one embodiment there is provided a pharmaceutical composition comprising a compound of Formula (IA) and at least one additional anti-tumour substance, for use in the treatment of cancer. In one embodiment the pharmaceutical composition also comprises at least one pharmaceutically acceptable diluent or carrier. In one embodiment there is provided a pharmaceutical composition comprising a compound of Formula (IB) and at least one additional anti-tumour substance, for use in the treatment of cancer. In one embodiment the pharmaceutical composition also comprises at least one pharmaceutically acceptable diluent or carrier.

In any embodiment the additional anti-tumour substance is a taxane. In one embodiment the taxane is paclitaxel. In one embodiment the taxane is docetaxel.

In any embodiment the additional anti-tumour substance is a platinum therapy. In one embodiment the platinum therapy is cisplatin, oxaliplatin, or carboplatin.

According to a further embodiment there is provided a kit comprising:
a) A compound of formula (I), or a pharmaceutically acceptable salt thereof, in a first unit dosage form;
b) A further additional anti-tumour substance in a further unit dosage form;
c) Container means for containing said first and further unit dosage forms; and optionally
d) Instructions for use.

In a further embodiment there is provided a kit comprising:
a) A compound of formula (IA), or a pharmaceutically acceptable salt thereof, in a first unit dosage form;
b) A further additional anti-tumour substance in a further unit dosage form;
c) Container means for containing said first and further unit dosage forms; and optionally
d) Instructions for use.

In a further embodiment there is provided a kit comprising:
a) A compound of formula (IB), or a pharmaceutically acceptable salt thereof, in a first unit dosage form;
b) A further additional anti-tumour substance in a further unit dosage form;
c) Container means for containing said first and further unit dosage forms; and optionally
d) Instructions for use.

In any embodiment the additional anti-tumour substance is a taxane. In one embodiment the taxane is paclitaxel. In one embodiment the taxane is docetaxel.

In any embodiment the additional anti-tumour substance is a platinum therapy. In one embodiment the platinum therapy is cisplatin, oxaliplatin, or carboplatin.

The compounds of Formula (I), (IA) and (IB) and pharmaceutically acceptable salts of any of these compounds may be administered as pharmaceutical compositions, comprising one or more pharmaceutically acceptable diluents or carriers.

Therefore, in one embodiment there is provided a pharmaceutical composition comprising a compound of Formula (I), or a pharmaceutically acceptable salt thereof, and at least one pharmaceutically acceptable diluent or carrier. In one embodiment there is provided a pharmaceutical composition comprising a compound of Formula (IA), or a pharmaceutically acceptable salt thereof, and at least one pharmaceutically acceptable diluent or carrier. In one embodiment there is provided a pharmaceutical composition comprising a compound of Formula (IB), or a pharmaceutically acceptable salt thereof, and at least one pharmaceutically acceptable diluent or carrier.

The compositions may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing), or as a suppository for rectal dosing. The compositions may be obtained by conventional procedures using conventional pharmaceutical excipients, well known in the art. Thus, compositions intended for oral use may contain, for example, one or more colouring, sweetening, flavouring and/or preservative agents.

In one embodiment there is provided a pharmaceutical composition comprising a compound of Formula (I), or a pharmaceutically acceptable salt thereof, and at least one pharmaceutically acceptable diluent or carrier, for use in therapy. In one embodiment there is provided a pharmaceutical composition comprising a compound of Formula (IA), or a pharmaceutically acceptable salt thereof, and at least one pharmaceutically acceptable diluent or carrier, for use in therapy. In one embodiment there is provided a pharmaceutical composition comprising a compound of Formula (IB), or a pharmaceutically acceptable salt thereof, and at least one pharmaceutically acceptable diluent or carrier, for use in therapy.

In one embodiment there is provided a pharmaceutical composition comprising a compound of Formula (I), or a pharmaceutically acceptable salt thereof, and at least one pharmaceutically acceptable diluent or carrier, for use in the treatment of cancer. In one embodiment said cancer is selected from the group consisting of breast cancer (for example triple negative breast cancer), lung cancer (for example non-small cell lung cancer), pancreatic cancer, bladder cancer and hepatocellular carcinoma. In one embodiment there is provided a pharmaceutical composition comprising a compound of Formula (IA), or a pharmaceutically acceptable salt thereof, and at least one pharmaceutically acceptable diluent or carrier, for use in the treatment of cancer. In one embodiment said cancer is selected from the group consisting of breast cancer (for example triple negative breast cancer), lung cancer (for example non-small cell lung cancer), pancreatic cancer, bladder cancer and hepatocellular carcinoma. In one embodiment there is provided a pharmaceutical composition comprising a compound of Formula (IB), or a pharmaceutically acceptable salt thereof, and at least one pharmaceutically acceptable diluent or carrier, for use in the treatment of cancer. In one embodiment said cancer is selected from the group consisting of breast cancer (for example triple negative breast cancer), lung cancer (for example non-small cell lung cancer), pancreatic cancer, bladder cancer and hepatocellular carcinoma.

The compound of Formula (I), (IA) or (IB) or a pharmaceutically acceptable salt of any of these compounds will normally be administered to a warm-blooded animal at a unit dose within the range 5-5000 mg/m$^2$ body area of the animal, or approximately 0.1-100 mg/kg, and this normally provides a therapeutically-effective dose. A unit dose form such as a tablet or capsule will usually contain, for example 1-250 mg of active ingredient. The daily dose will necessarily be varied depending upon the host treated, the particular route of administration, any therapies being co-administered, and the severity of the illness being treated. Accordingly the practitioner who is treating any particular patient may determine the optimum dosage.

EXAMPLES

The various embodiments are illustrated by the following Examples. The invention is not to be interpreted as being limited to the Examples. During the preparation of the Examples, generally:

i. Operations were carried out at room temperature, i.e. in the range of about 17 to 30° C. and under atmospheric conditions unless otherwise stated;

ii. Evaporations were carried out by rotary evaporation or utilising Genevac equipment in vacuo and work-up procedures were carried out after removal of residual solids by filtration;

iii. Flash chromatography purifications were performed on an automated Isco Combiflash Companion using Grace Resolve prepacked silica columns, and (reverse phase flash) Isco Combiflash Rf using Redisep Gold C18 columns;

iv. Yields, where present, are not necessarily the maximum attainable;

v. Structures of end-products of Formula (I) were confirmed by nuclear magnetic resonance (NMR) spectroscopy, with NMR chemical shift values measured on the delta scale. Proton magnetic resonance spectra were determined using a Bruker Avance 700 (700 MHz), Bruker Avance 500 (500 MHz), Bruker 400 (400 MHz) or Bruker 300 (300 MHz) instrument; 19F NMR were determined at 282 MHz or 376 MHz; 13C NMR were determined at 75 MHz or 100 MHz; measurements were taken at around 20-30° C. unless otherwise specified; the following abbreviations have been used: s, singlet; d, doublet; t, triplet; q, quartet; m, multiplet; dd, doublet of doublets; ddd, doublet of doublet of doublet; dt, doublet of triplets; dtd, double triplet of doublets; dddd, double double doublet of doublets; td, triplet of doublets; dq, doublet of quartets; bs, broad signal;

vi. End-products of Formula (I) were also characterised by mass spectroscopy following liquid chromatography (LCMS), using a HPLC system based on a Waters 2790/95 LC system with a 2996 PDA and a 2000 amu ZQ single quadrupole mass spectrometer. The solvents used were A=Water, B=Acetonitrile, C=50:50 acetonitrile:water 0.1% formic acid and D=50:50 acetonitrile:water 0.1% ammonium hydroxide. At a flow rate of 1.1 mL/min 5 µL of sample was injected onto a 50×2.1 5 µm Phenomenex Gemini NX column. The gradient ran from 95% A to 95% B for 4.0 mins with a constant 5% infusion of C (for acid analysis, D is used for base analysis). The flow was held at 95% B for 0.5 mins before returning to start conditions. The Data was acquired from 150 to 850 amu in both positive and negative mode on the Mass Spectrometer and 220-320 nm on the PDA. LCMS was also performed on a UPLC system utilising a Waters Aquity Binary pump with sample manager, Aquity PDA and an SQD Mass spectrometer. The solvents used were A1=0.1% formic acid (aqueous), B1 0.1% formic acid in acetonitrile, A2=0.1% ammonium hydroxide (aqueous) and B2 0.1% ammonium hydroxide in acetonitrile. At a flow rate of 1 mL/min 1 µL of sample was injected onto a 50×2.1 1.7 um Waters BEH column (at 40° C.). The gradient ran from 97% A1 to 97% B1 over 1.30 mins before being held for 0.2 min and returning to start conditions (substitute A1 and B1 for A2 and B2 for base analysis). Data was acquired from 150-1000 amu in positive and negative ion mode on the mass spectrometer and 245-320 amu on the PDA;

vii. Intermediates were not generally fully characterised and purity was assessed by thin layer chromatographic, mass spectral, HPLC and/or NMR analysis;

viii. X-ray powder diffraction spectra were determined using a PANalytical CubiX PRO diffractometer by mounting the sample of the crystalline material on a single silicon crystal wafer mount and spreading the sample out into a thin layer. The sample was spun at 30 revolutions per minute (to improve counting statistics) and irradiated with X-rays generated by a copper long-fine focus tube operated at 45 kV and 40 mA with a wavelength of 1.5418 angstroms;

ix. Single crystal X-ray data was collected on a Rigaku AFC12 goniometer equipped with an enhanced sensitivity (HG) Saturn724+ detector mounted at the window of an FR-E+ SuperBright molybdenum rotating anode generator with HF Varimax optics (100 μm focus). Cell determination, Data collection, Data reduction and cell refinement & Absorption correction was performed using CrystalClear-SM Expert 2.0 r7 (Rigaku, 2011). Structure solution was carried out with SHELXS97 (Sheldrick, G. M., *Acta. Cryst.* 2008, A64, 112-122), with structure refinement performed using SHELXL2012 (G. M. Sheldrick (2012), University of Göttingen, Germany). Graphics were displayed on CrystalMaker: a crystal and molecular structures program for Mac and Window (CrystalMaker Software Ltd, Oxford, England, www.crystalmaker.com). Data was collected at 100K;

x. The following abbreviations have been used: h=hour(s); r.t.=room temperature (~17-30° C.); conc.=concentrated; FCC=flash column chromatography using silica; AIBN=azobisisobutyronitrile; DCM=dichloromethane; DIPEA=di-isopropyl ethylamine; DMA=N,N-dimethylacetamide; DMF=N,N-dimethylformamide; DMSO=dimethylsulfoxide; EDC=1-Ethyl-3-(3-dimethylaminopropyl)carbodiimide; $Et_2O$=diethyl ether; EtOAc=ethyl acetate; EtOH=ethanol; HATU=1-[bis(dimethylamino)methylene]-1H-1,2,3-triazolo[4,5-b]pyridinium 3-oxid hexafluorophosphate; HOBT=hydroxybenzotriazole; $K_2CO_3$=potassium carbonate; MeOH=methanol; MeCN=acetonitrile; $MgSO_4$=anhydrous magnesium sulphate; $Na_2SO_4$=anhydrous sodium sulphate; NBS=N-bromo succinimide; NMP=N-methyl pyrrolidine; TFA=trifluoroacetic acid; THF=tetrahydrofuran; sat.=saturated aqueous solution; and xi. IUPAC names were generated using 'SmiToSd', a proprietary program built around the OpenEye Lexichem toolkit (http://www.eyesopen.com/lexichem-tk).

Example 1(a)

(2S)-2-Methoxy-2-phenyl-N-[5-[[(3R)-1-(1,2,4-triazin-3-yl)pyrrolidin-3-yl]amino]-1,3,4-thiadiazol-2-yl]acetamide 5-Bromo-1,3,4-thiadiazol-2-amine (229 mg, 1.27 mmol), (3R)-1-(1,2,4-triazin-3-yl)pyrrolidin-3-amine (Intermediate 1, 200 mg, 1.21 mmol) and DIPEA (0.253 mL, 1.45 mmol) were dissolved in DMF (5 mL) and sealed into a microwave tube. The reaction was heated to 100° C. for 90 minutes in a microwave reactor to give crude N-[(3R)-1-(1,2,4-triazin-3-yl)pyrrolidin-3-yl]-1,3,4-thiadiazole-2,5-diamine. LCMS indicated complete reaction. This material was taken forward crude in solution, assuming 100% conversion, and used in the next step. HATU (276 mg, 0.73 mmol) was added to (2S)-2-methoxy-2-phenylacetic acid (106 mg, 0.64 mmol), N'-[(3R)-1-(1,2,4-triazin-3-yl)pyrrolidin-3-yl]-1,3,4-thiadiazole-2,5-diamine (prepared as above, 160 mg, 0.61 mmol), and DIPEA (0.316 mL, 1.82 mmol) in DMF (3 mL) at 0° C. The resulting solution was then stirred at r.t. for 2 h. The reaction mixture was partitioned between 2-methyltetrahydrofuran and aqueous brine. The organic layer was dried ($MgSO_4$), filtered and evaporated under reduced pressure. The crude product was purified by preparative HPLC (Waters XBridge Prep C18 OBD column, 5 μm silica, 50 mm diameter, 100 mm length), using decreasingly polar mixtures of water (containing 1% ammonia) and MeCN as eluents. Fractions containing the desired compound were evaporated to dryness to afford (2S)-2-methoxy-2-phenyl-N-[5-[[(3R)-1-(1,2,4-triazin-3-yl)pyrrolidin-3-yl]amino]-1,3,4-thiadiazol-2-yl]acetamide (118 mg, 47%) as a solid. $^1$H NMR (500 MHz, DMSO-d6, 30° C.) δ 2.03-2.14 (1H, m), 2.24-2.34 (1H, m), 3.31 (3H, s), 3.65 (3H, s), 3.81 (1H, s), 4.33-4.41 (1H, m), 4.98 (1H, s), 7.32-7.4 (3H, m), 7.43-7.48 (2H, m), 7.69 (1H, d), 8.31 (1H, d), 8.60 (1H, d); m/z: $ES^+$ $[M+H]^+$ 412.9.

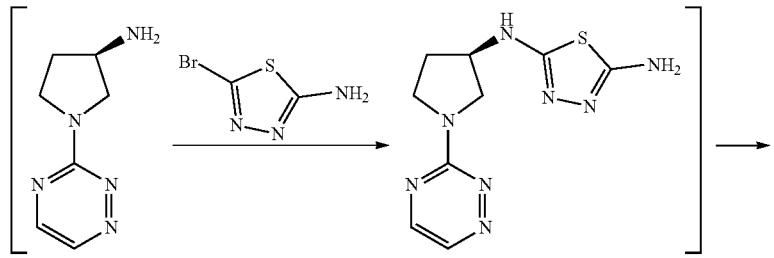

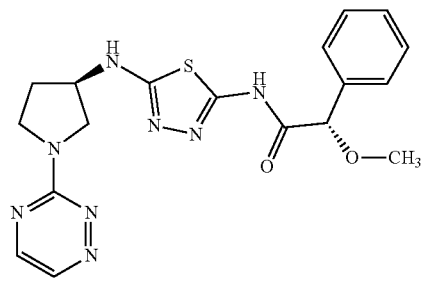

Example 1(b)

(2R)-2-Methoxy-2-phenyl-N-[5-[[(3R)-1-(1,2,4-triazin-3-yl)pyrrolidin-3-yl]amino]-1,3,4-thiadiazol-2-yl]acetamide

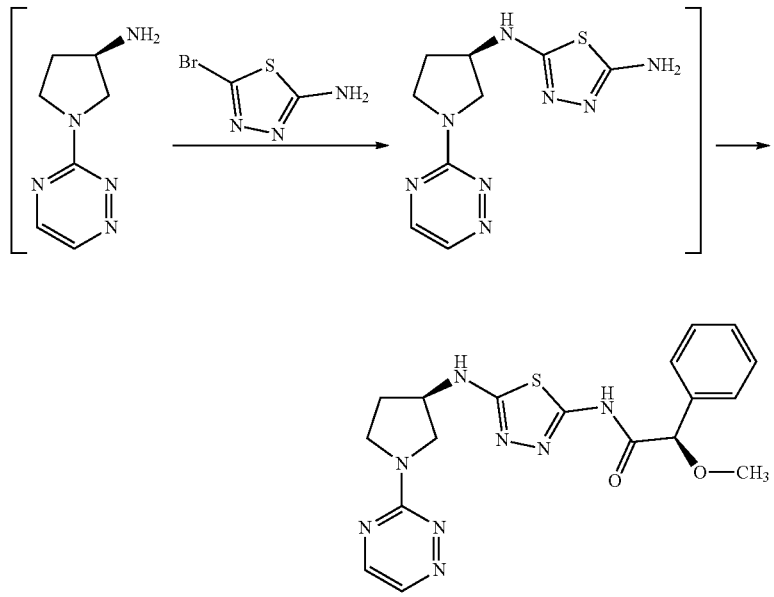

DIPEA (3.17 mL, 18.16 mmol) was added to (3R)-1-(1,2,4-triazin-3-yl)pyrrolidin-3-amine (Intermediate 1, 1.500 g, 9.08 mmol) and 5-bromo-1,3,4-thiadiazol-2-amine (1.635 g, 9.08 mmol) in DMF (10 mL). The resulting solution was stirred at 100° C. for 60 minutes to give crude N'-[(3R)-1-(1,2,4-triazin-3-yl)pyrrolidin-3-yl]-1,3,4-thiadiazole-2,5-diamine. The reaction was then cooled to r.t. and taken forward crude in solution. HATU (4.14 g, 10.90 mmol) was added to (2S)-2-methoxy-2-phenylacetic acid (1.509 g, 9.08 mmol), N'-[(3R)-1-(1,2,4-triazin-3-yl)pyrrolidin-3-yl]-1,3,4-thiadiazole-2,5-diamine (2.4 g, 9.08 mmol) and DIPEA (4.74 ml, 27.24 mmol) in DMF (1.5 ml) at r.t. under nitrogen. The resulting solution was stirred at r.t. for 18 h. The reaction mixture was evaporated to dryness and dissolved in MeOH (20 mL). The solution was purified by ion exchange chromatography using an SCX2 column. The desired product was eluted from the column using 7M ammonia/MeOH and pure fractions were evaporated to dryness to afford crude product as a brown gum (3.68 g). The crude product was purified by FCC, elution gradient 0 to 5% MeOH in EtOAc. Pure fractions were evaporated to dryness then triturated and azeotroped with Et$_2$O/heptane mixtures to afford the product (2.80 g, 75%) as yellow foam. Chiral HPLC analysis showed a 95:5 mixture of diastereoisomers. This was then dissolved in Heptane/EtOH/MeOH 50/25/25 and the crude product was purified by preparative HPLC (Chiralpak IA column, 20 μm silica, 100 mm diameter, 330 mm length, eluent Heptane/EtOH/MeOH 50/25/25 at 400 ml/min) to give (2R)-2-Methoxy-2-phenyl-N-[5-[[(3R)-1-(1,2,4-triazin-3-yl)pyrrolidin-3-yl]amino]-1,3,4-thiadiazol-2-yl]acetamide as the first eluted isomer (yellow solid, 0.100 g, 4%). $^1$H NMR (500 MHz, DMSO, 30° C.) δ 2.09 (1H, dd), 2.30 (1H, dd), 3.32 (3H, s), 3.53-3.89 (4H, m), 4.38 (1H, s), 4.99 (1H, s), 7.38 (3H, dt), 7.47 (2H, d), 7.70 (1H, d), 8.32 (1H, d), 8.61 (1H, d), 12.22 (1H, s); m/z: ES$^+$ [M+H]$^+$ 413. (2S)-2-Methoxy-2-phenyl-N-[5-[[(3R)-1-(1,2,4-triazin-3-yl)pyrrolidin-3-yl]amino]-1,3,4-thiadiazol-2-yl]acetamide (Example 1(a), 1.850 g, 66%) was also isolated from the reaction as the second eluted isomer (analytical data as reported above).

Example 2(a)

(2S)-2-Methoxy-2-phenyl-N-[5-[[(3R)-1-pyridazin-3-ylpyrrolidin-3-yl]amino]-1,3,4-thiadiazol-2-yl]acetamide

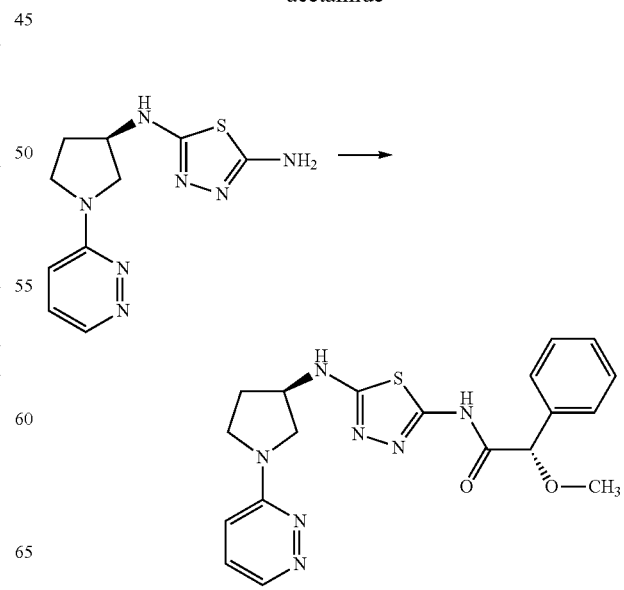

A mixture of N'-[(3R)-1-pyridazin-3-ylpyrrolidin-3-yl]-1,3,4-thiadiazole-2,5-diamine (Intermediate 5, 150 mg, 0.57 mmol), (2S)-2-methoxy-2-phenylacetic acid (174.4 mg, 0.57 mmol), HATU (325 mg, 0.86 mmol) and DIPEA (147 mg, 1.14 mmol) in DMF (3 mL) were stirred for 16 h at r.t. The crude reaction mixture was then purified by Prep-HPLC (column: SunFire Prep C18 OBD Column, 5 m, 19 mm×150 mm; mobile phase: MeOH and water with 0.1% TFA, eluting with 25.0% water with 0.1% TFA up to 50.0% water with 0.1% TFA over an 8 minute period; detector, UV 220, 254 nm). This delivered product (43 mg, 18%) as a white solid. $^1$H NMR (300 MHz, DMSO-d6, 26° C.) δ 2.00-2.10 (1H, m), 2.23-2.49 (1H, m), 3.30 (3H, s), 3.45-3.57 (3H, m), 3.71-3.76 (1H, m), 4.33-4.38 (1H, m), 4.97 (1H, s), 6.87 (1H, d), 7.30-7.47 (6H, m), 7.69 (1H, d), 8.46 (1H, d), 12.22 (1H, br); m/z: ES$^+$ [M+H]$^+$ 412.

Material prepared using the above method was analysed by XRPD and found to be amorphous, with a melting point of 82.1° C. (onset). Slurrying experiments were carried out on the amorphous material by placing 20 mg in a vial with a magnetic stirrer bar, and then adding approximately 2 mL of a given solvent. The vial was then sealed tightly with a cap and the mixture left to stir on a magnetic stirrer plate. After approximately 3 days, the sample was removed from the plate, the cap taken off and the solvent left to evaporate under ambient conditions before analysis of the resultant solid by XRPD.

Three forms (Types A, B and C) were distinguished and determined to be partially crystalline. Form A material was produced by slurrying in isopropyl alcohol as solvent at 25° C. Form B material was produced by slurrying in EtOAc as solvent at 25° C. Form C material was produced by slurrying in MeCN as solvent at 25° C.

Form D material was produced by heating Form B or Form C material to 200° C. before cooling to r.t. This form was determined to be crystalline by XRPD, with the following characteristic diffraction peaks.

TABLE 1

Characteristic X-Ray powder diffraction peaks for Form D of (2S)-2-methoxy-2-phenyl-N-[5-[[(3R)-1-pyridazin-3-ylpyrrolidin-3-yl]amino]-1,3,4-thiadiazol-2-yl]acetamide

| Angle 2-Theta (2θ) | Intensity (%) |
|---|---|
| 19.3 | 100 |
| 7.9 | 69.8 |
| 18.9 | 36.3 |
| 21.2 | 32.1 |
| 8.3 | 24.5 |
| 14.6 | 23.8 |
| 24.4 | 22.2 |
| 18.4 | 21.8 |
| 25.3 | 20.8 |
| 24.6 | 19.3 |

Single crystal X-Ray analysis was performed on the Form D material, confirming the compound to be a single diastereomer of the stereochemistry shown above.

Example 2(a) was also prepared on a large scale using the following alternative procedure. N'-[(3R)-1-pyridazin-3-ylpyrrolidin-3-yl]-1,3,4-thiadiazole-2,5-diamine (Intermediate 5, 32.8 g, 124.56 mmol) and (2S)-2-methoxy-2-phenylacetic acid (21.73 g, 130.79 mmol) were slurried in DMF (135 mL) with DIPEA (43.4 mL, 249.12 mmol). 1-Propanephosphonic acid cyclic anhydride (50% w/w in DMF, 91 mL, 155.70 mmol) was added dropwise keeping the reaction contents temperature <20° C. The solid dissolved and analysis of the solution showed the reaction was complete. Purification via 13×50 g SCX columns results in a MeOH solution which was concentrated by rotary evaporation to give a slurry. The slurry was diluted with 300 ml MTBE and the solid product isolated by vacuum filtration (analytical data consistent with that reported above).

Example 2(b)

(2R)-2-Methoxy-2-phenyl-N-[5-[[(3R)-1-pyridazin-3-ylpyrrolidin-3-yl]amino]-1,3,4-thiadiazol-2-yl]acetamide

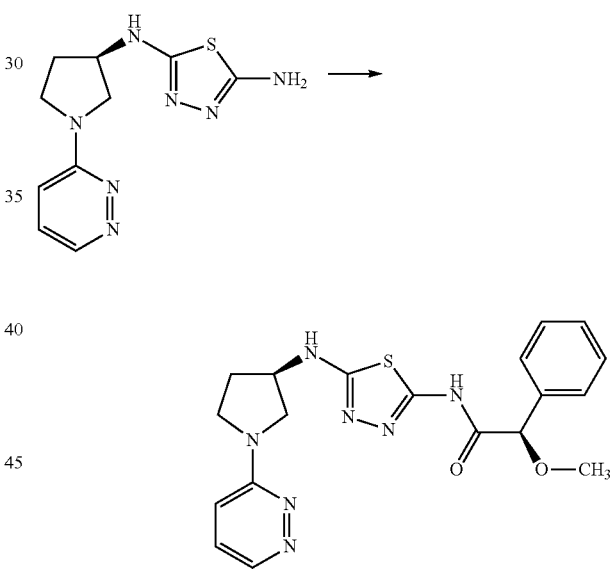

A solution of N'-[(3R)-1-pyridazin-3-ylpyrrolidin-3-yl]-1,3,4-thiadiazole-2,5-diamine (Intermediate 5, 150 mg, 0.57 mmol), (2R)-2-methoxy-2-phenylacetic acid (94 mg, 0.57 mmol), HATU (325 mg, 0.86 mmol) and DIEA (147 mg, 1.14 mmol) in DMF (3 mL) was stirred for 16 h at r.t. The crude product was purified by Prep-HPLC with the following conditions: Column, SunFire Prep C18 OBD Column, 5 m, 19×150 mm; mobile phase=methanol and water containing 0.1% TFA (25.0% water with 0.1% TFA up to 50.0% in 8 min); detector=UV 220,254 nm. These conditions furnished 43 mg (19%) of (2R)-2-Methoxy-2-phenyl-N-[5-[[(3R)-1-pyridazin-3-ylpyrrolidin-3-yl]amino]-1,3,4-thiadiazol-2-yl]acetamide (Example 2(b)) as a white solid; m/z: ES$^+$ [M+H]$^+$ 412.

Example 3

(2S)-2-Methoxy-2-phenyl-N-[5-[[(3R)-1-(1,2,4-triazin-6-yl)pyrrolidin-3-yl]amino]-1,3,4-thiadiazol-2-yl]acetamide

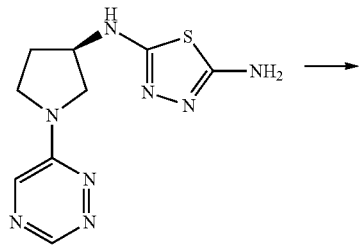

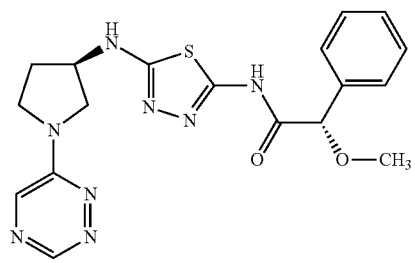

HATU (319 mg, 0.84 mmol) was added to N'-[(3R)-1-(1,2,4-triazin-6-yl)pyrrolidin-3-yl]-1,3,4-thiadiazole-2,5-diamine (Intermediate 9, 185 mg, 0.70 mmol), (2S)-2-methoxy-2-phenylacetic acid (116 mg, 0.70 mmol) and DIPEA (0.122 mL, 0.70 mmol) in DMF (5 mL) at 0° C. The resulting solution was stirred at 0° C. for 1 h. The reaction mixture was diluted with MeOH (5 mL) and purified by ion exchange chromatography, using a 20 g SCX column. The desired product was eluted from the column using 3M ammonia in MeOH, and pure fractions were evaporated to dryness to afford crude product. The crude product was purified by FCC, elution gradient 0 to 8% MeOH in DCM. Pure fractions were evaporated to dryness to afford (2S)-2-methoxy-2-phenyl-N-[5-[[(3R)-1-(1,2,4-triazin-6-yl)pyrrolidin-3-yl]amino]-1,3,4-thiadiazol-2-yl]acetamide (200 mg, 69%) as a white solid. $^1$H NMR (400 MHz, DMSO-d6, 27° C.) δ 2.02-2.13 (1H, m), 2.21-2.34 (1H, m), 3.30 (3H, s), 3.54 (1H, dd), 3.61 (2H, dd), 3.78 (1H, dd), 4.34-4.44 (1H, m), 4.97 (1H, s), 7.30-7.40 (3H, m), 7.45 (2H, dd), 7.68 (1H, d), 8.26 (1H, s), 8.94 (1H, s), 12.21 (1H, s); m/z: ES$^+$ [M+H]$^+$ 413.

Examples 4(a) and 4(b)

(2S)-2-Methoxy-2-(3-methoxyphenyl)-N-[5-[[(3R)-1-(1,2,4-triazin-3-yl)pyrrolidin-3-yl]amino]-1,3,4-thiadiazol-2-yl]acetamide and (2R)-2-Methoxy-2-(3-methoxyphenyl)-N-[5-[[(3R)-1-(1,2,4-triazin-3-yl)pyrrolidin-3-yl]amino]-1,3,4-thiadiazol-2-yl]acetamide

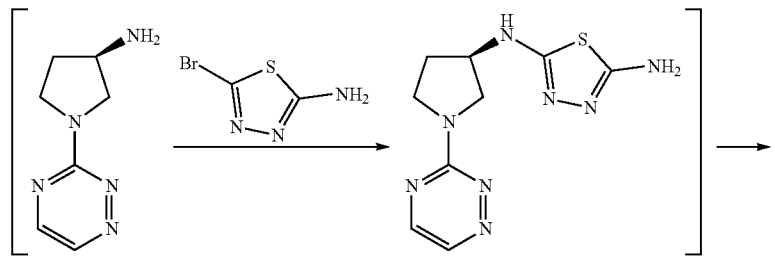

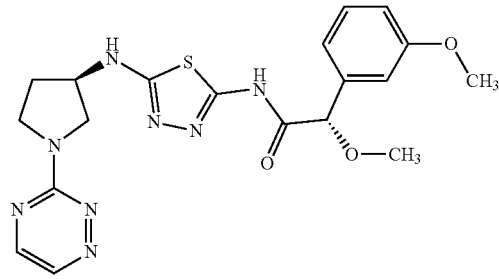

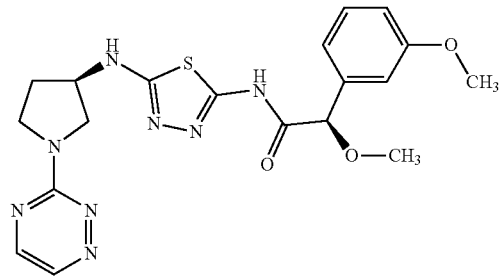

DIPEA (0.917 mL, 5.27 mmol) was added to (3R)-1-(1,2,4-triazin-3-yl)pyrrolidin-3-amine (Intermediate 1, 290 mg, 1.76 mmol) and 5-bromo-1,3,4-thiadiazol-2-amine (316 mg, 1.76 mmol) in DMF (8 mL) at 21° C. under nitrogen. The resulting solution was stirred at 100° C. for 1 h, then allowed to cool to r.t. 2-Methoxy-2-(3-methoxyphenyl)acetic acid (Intermediate 15, 180 mg, 0.92 mmol), followed by HATU (380 mg, 1.00 mmol) was added to the solution above and the reaction was left to stir at r.t. for 1 h. The crude product was purified by ion exchange chromatography, using an SCX column. The desired product was eluted from the column using 1M ammonia/MeOH and fractions adsorbed onto silica. The crude product was purified by FCC, elution gradient 0 to 15% MeOH (with 5% 1M ammonia/MeOH) in EtOAc, and fractions were evaporated to give crude product. Diastereomer separation was achieved on an AD column using 50/50, EtOH/MeOH as eluents. The sample was dissolved in EtOH (5 mL). Fractions containing the desired compounds were evaporated to dryness to afford:

Example 4(a) as the first eluted isomer (62 mg, 8%). $^1$H NMR (400 MHz, DMSO-d6, 30° C.) δ 2.09 (1H, m), 2.24-2.4 (1H, m), 3.32 (3H, s), 3.62 (2H, m), 3.76 (3H, s), 4.38 (1H, m), 4.94 (1H, s), 6.83-6.98 (1H, dd), 7.00-7.10 (2H, m), 7.29 (1H, dd), 7.66 (1H, d), 8.31 (1H, d), 8.61 (1H, d), 12.11 (1H, s); m/z: ES$^+$ [M+H]$^+$ 443.

Example 4(b) as the second eluted isomer (48 mg, 6%). $^1$H NMR (400 MHz, DMSO-d6, 30° C.) δ 2.09 (1H, m), 2.24-2.4 (1H, m), 3.32 (3H, s), 3.62 (2H, m), 3.76 (3H, s), 4.38 (1H, m), 4.94 (1H, s), 6.83-6.98 (1H, dd), 7-7.1 (2H, m), 7.29 (1H, dd), 7.66 (1H, d), 8.31 (1H, d), 8.61 (1H, d), 12.11 (1H, s); m/z: ES$^+$ [M+H]$^+$ 443.

Examples 5(a) and 5(b)

(2S)-2-Methoxy-2-(3-methoxyphenyl)-N-[5-[[(3R)-1-pyridazin-3-ylpyrrolidin-3-yl]amino]-1,3,4-thiadiazol-2-yl]acetamide and (2R)-2-Methoxy-2-(3-methoxyphenyl)-N-[5-[[(3R)-1-pyridazin-3-ylpyrrolidin-3-yl]amino]-1,3,4-thiadiazol-2-yl]acetamide

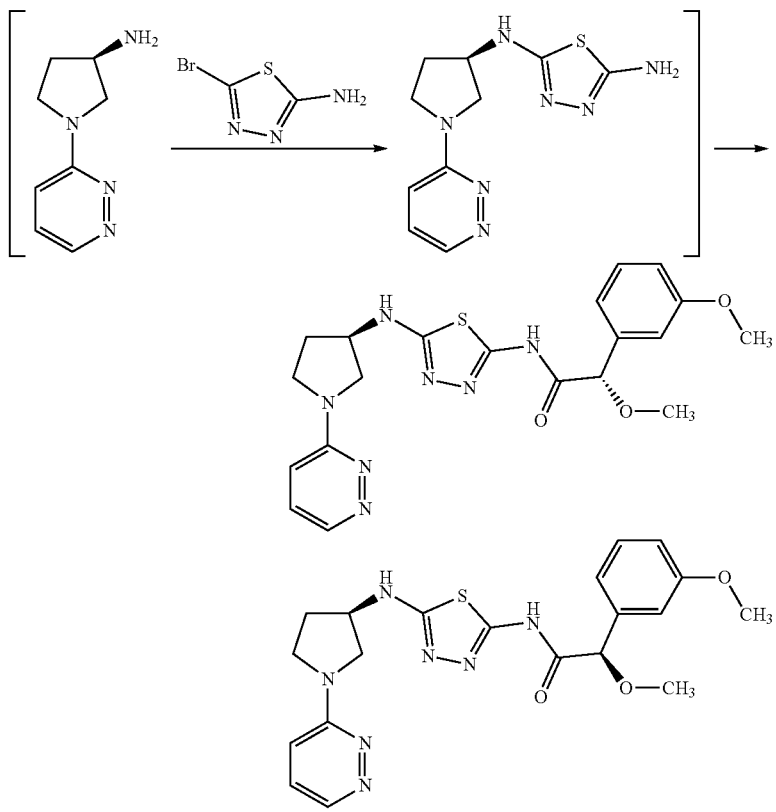

DIPEA (0.994 mL, 5.69 mmol) was added to (3R)-1-pyridazin-3-ylpyrrolidin-3-amine dihydrochloride (Intermediate 6, 300 mg, 1.27 mmol), and 5-bromo-1,3,4-thiadiazol-2-amine (228 mg, 1.27 mmol) in DMF (4 mL). The resulting solution was stirred at 100° C. for 60 minutes to give crude N'-[(3R)-1-pyridazin-3-ylpyrrolidin-3-yl]-1,3,4-thiadiazole-2,5-diamine. To the solution of N'-[(3R)-1-pyridazin-3-ylpyrrolidin-3-yl]-1,3,4-thiadiazole-2,5-diamine (333 mg, 1.26 mmol) in DMF (4 mL), already containing DIPEA (0.994 mL, 5.69 mmol), was added the 2-methoxy-2-(3-methoxyphenyl)acetic acid (Intermediate 15, 248 mg, 1.26 mmol) followed by the HATU (481 mg, 1.26 mmol). The reaction was left to stir at r.t. overnight whereupon it was judged complete by LCMS. The crude reaction mixture was loaded onto an SCX2 cartridge (20 g). The crude product was purified by ion exchange chromatography. The desired product was eluted from the column using 1M ammonia/MeOH and fractions were evaporated to dryness to afford crude product as a brown solid (500 mg). The crude product was purified by preparative HPLC (Waters XBridge Prep C18 OBD column, 5 m silica, 50 mm diameter, 100 mm length), using decreasingly polar mixtures of water (containing 1% ammonia) and MeCN as eluents. Fractions containing the desired compound were evaporated to dryness to afford 2-methoxy-2-(3-methoxyphenyl)-N-[5-[[(3R)-1-pyridazin-3-ylpyrrolidin-3-yl]amino]-1,3,4-thiadiazol-2-yl]acetamide (161 mg). The crude product was purified by preparative chiral HPLC (Phenomenex Lux C2 column, 20 m silica, 50 mm diameter, 250 mm length), eluting with MeOH at 100 mL/min. Fractions containing the desired compounds were evaporated to dryness to afford:

Example 5(a) as the first eluted isomer (57 mg, 0.129 mmol, 10%). $^1$H NMR (400 MHz, DMSO-d6, 30° C.) δ 2.03-2.13 (1H, m), 2.23-2.33 (1H, m), 3.32 (3H, s), 3.46-3.63 (3H, m), 3.76 (4H, s), 4.33-4.45 (1H, m), 4.95 (1H, s), 6.86 (1H, dd), 6.91 (1H, ddd), 7.00-7.08 (2H, m), 7.26-7.37 (2H, m), 7.66 (1H, d), 8.48 (1H, dd), 12.13 (1H, s); m/z: ES$^+$ [M+H]$^+$ 442.55.

Example 5(b) as the second eluted isomer (58 mg, 10%). $^1$H NMR (400 MHz, DMSO-d6, 30° C.) δ 2.02-2.12 (1H, m), 2.23-2.34 (1H, m), 3.31 (3H, s), 3.43-3.62 (3H, m), 3.76 (4H, s), 4.33-4.45 (1H, m), 4.93 (1H, s), 6.86 (1H, dd), 6.91 (1H, ddd), 7.00-7.08 (2H, m), 7.26-7.36 (2H, m), 7.62 (1H, d), 8.48 (1H, dd), 12.14 (1H, s); m/z: ES$^+$ [M+H]$^+$ 442.55.

Examples 6(a) and 6(b)

(2S)-2-[3-(Difluoromethoxy)phenyl]-2-methoxy-N-[5-[[(3R)-1-(1,2,4-triazin-3-yl)pyrrolidin-3-yl]amino]-1,3,4-thiadiazol-2-yl]acetamide and (2R)-2-[3-(Difluoromethoxy)phenyl]-2-methoxy-N-[5-[[(3R)-1-(1,2,4-triazin-3-yl)pyrrolidin-3-yl]amino]-1,3,4-thiadiazol-2-yl]acetamide DIPEA (917 µL, 5.27 mmol) was added to (3R)-1-(1,2,4-triazin-3-yl)pyrrolidin-3-amine (Intermediate 1, 290 mg, 1.76 mmol) and 5-bromo-1,3,4-thiadiazol-2-amine (316 mg, 1.76 mmol) in DMF (8 mL) at 21° C. under nitrogen. The resulting solution was stirred at 100° C. for 1 h, then cooled to r.t. 2-[3-(difluoromethoxy)phenyl]-2-methoxyacetic acid (Intermediate 16, 213 mg, 0.92 mmol), followed by HATU (380 mg, 1.00 mmol) was added to the solution and the reaction was left to stir at r.t. for 1 h. The crude product was purified by ion exchange chromatography, using an SCX column. The desired product was eluted from the column using 1M ammonia/MeOH and fractions evaporated to a gum (200 mg). The crude product was purified by FCC, elution gradient 0 to 15% MeOH (with 5% 1M ammonia/MeOH) in EtOAc. Fractions were then evaporated to give crude product. The crude product was purified by preparative chiral HPLC (C2 column, 3 µm silica, 4.6 mm diameter, 50 mm length) using EtOH as eluent. Fractions containing the desired compounds were evaporated to dryness to afford:

Example 6(b) as the first eluted isomer (65 mg, 16%). $^1$H NMR (500 MHz, DMSO-d6, 30° C.) δ 2.09 (1H, m), 2.30 (1H, m), 3.34 (3H, s), 3.66 (3H, m), 3.81 (1H, m), 4.38 (1H, m), 5.02 (1H, s), 7.05-7.26 (2H, m), 7.28 (1H, s), 7.34 (1H, d), 7.45 (1H, dd), 7.70 (1H, d), 8.32 (1H, d), 8.61 (1H, d), 12.25 (1H, s); m/z: ES$^+$ [M+H]$^+$ 479.

Example 6(a) as the second eluted isomer (69 mg, 17%). $^1$H NMR (500 MHz, DMSO-d6, 30° C.) δ 2.09 (1H, m), 2.30 (1H, m), 3.34 (3H, s), 3.66 (3H, m), 3.81 (1H, m), 4.38 (1H, m), 5.02 (1H, s), 7.05-7.26 (2H, m), 7.28 (1H, s), 7.34 (1H, d), 7.45 (1H, dd), 7.70 (1H, d), 8.32 (1H, d), 8.61 (1H, d), 12.25 (1H, s); m/z: ES$^+$ [M+H]$^+$ 479.

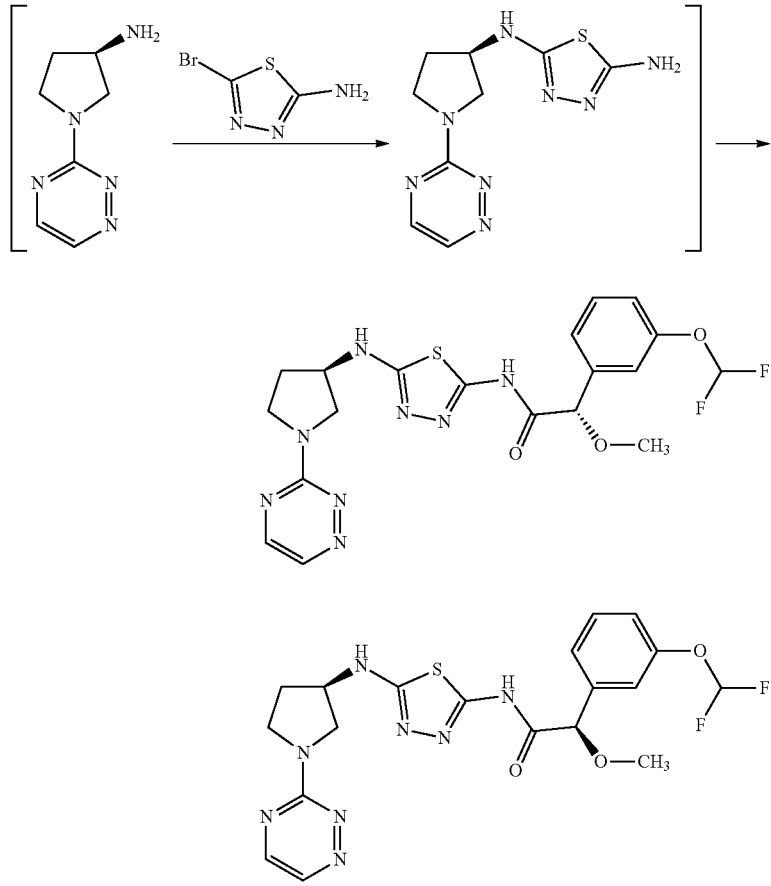

Examples 7(a) and 7(b)

(2S)-2-[3-(Difluoromethoxy)phenyl]-2-methoxy-N-[5-[[(3R)-1-pyridazin-3-ylpyrrolidin-3-yl]amino]-1,3,4-thiadiazol-2-yl]acetamide and (2R)-2-[3-(Difluoromethoxy)phenyl]-2-methoxy-N-[5-[[(3R)-1-pyridazin-3-ylpyrrolidin-3-yl]amino]-1,3,4-thiadiazol-2-yl]acetamide

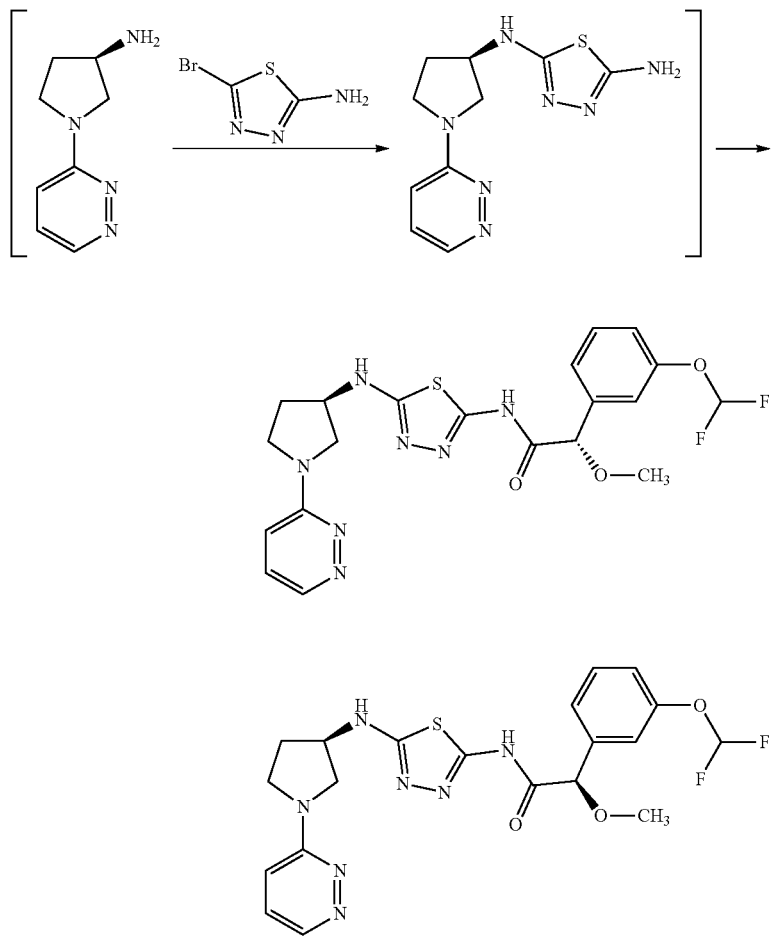

A mixture of (3R)-1-pyridazin-3-ylpyrrolidin-3-amine dihydrochloride (Intermediate 6, 200 mg, 0.84 mmol), 5-bromo-1,3,4-thiadiazol-2-amine (182 mg, 1.01 mmol), DIPEA (1, 5.73 mmol) and DMF (3 mL) was stirred at 100° C. (external block temp). for 30 min and cooled to r.t. 2-[3-(Difluoromethoxy)phenyl]-2-methoxyacetic acid (Intermediate 16, 255 mg, 1.10 mmol) was added followed by HATU (481 mg, 1.27 mmol) and the mixture was stirred for 30 min. The mixture was diluted with EtOAc (100 mL) and washed with sat. sodium hydrogencarbonate solution (20 mL), and brine (20 mL). The organic layer was dried over $Na_2SO_4$, filtered and evaporated to afford a brown oil. The crude product was purified by FCC (elution gradient 0 to 15% MeOH in EtOAc). Pure fractions were evaporated to dryness to afford 2-[3-(difluoromethoxy)phenyl]-2-methoxy-N-[5-[[(3R)-1-pyridazin-3-ylpyrrolidin-3-yl]amino]-1,3,4-thiadiazol-2-yl]acetamide (233 mg, 55%) as a beige solid containing a mixture of diastereoisomers. The mixture was separated by chiral HPLC to afford:

Example 7(a) as the first eluted isomer (solid, 80 mg, 20%). $^1$H NMR (400 MHz, DMSO-d6, 30° C.) δ 2.08 (1H, dt), 2.28 (1H, dd), 3.34 (3H, s), 3.49 (1H, dd), 3.53-3.62 (2H, m), 3.75 (1H, dd), 4.29-4.48 (1H, m), 5.02 (1H, s), 6.86 (1H, dd), 7.16 (1H, dd), 7.28 (1H, s), 7.23 (1H, t), 7.30-7.36 (2H, m), 7.45 (1H, t). 7.67 (1H, d), 8.48 (1H, dd), 12.21 (1H, s); m/z: ES$^+$ [M+H]$^+$ 478.

Example 7(b) as the second eluted isomer (77 mg, 19%). $^1$H NMR (400 MHz, DMSO-d6, 30° C.) δ 2.08 (1H, dt), 2.28 (1H, dt), 3.33 (3H, s), 3.50 (1H, dd), 3.53-3.63 (3H, m), 3.76 (1H, dd), 4.35-4.43 (1H, m), 5.01 (1H, s), 6.86 (1H, dd), 7.16 (1H, dd), 7.28 (1H, s), 7.30-7.36 (2H, m), 7.45 (1H, t), 7.65 (1H, d), 8.48 (1H, dd), 12.22 (1H, s); m/z: ES$^+$ [M+H]$^+$ 478.

Examples 8(a) and 8(b)

(2S)-2-Methoxy-N-[5-[[(3R)-1-(1,2,4-triazin-3-yl)pyrrolidin-3-yl]amino]-1,3,4-thiadiazol-2-yl]-2-[3-(trifluoromethoxy)phenyl]acetamide and (2R)-2-Methoxy-N-[5-[[(3R)-1-(1,2,4-triazin-3-yl)pyrrolidin-3-yl]amino]-1,3,4-thiadiazol-2-yl]-2-[3-(trifluoromethoxy)phenyl]acetamide

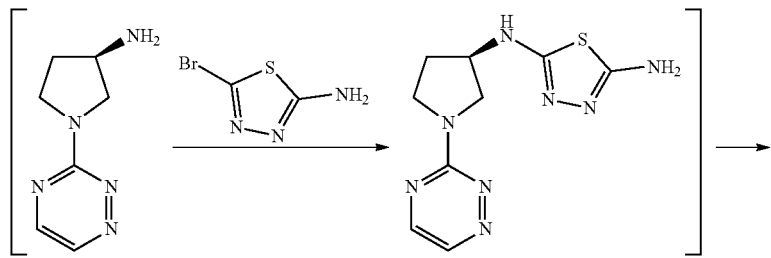

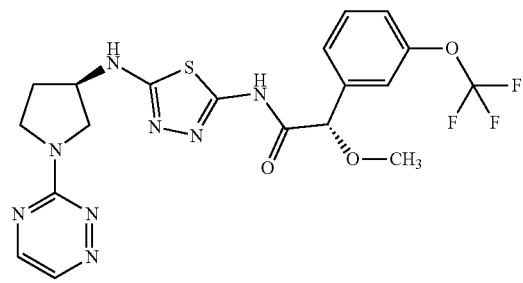

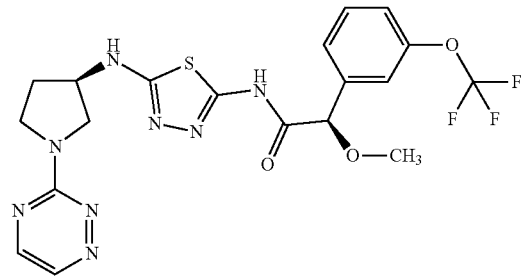

DIPEA (423 μL, 2.42 mmol) was added to (3R)-1-(1,2,4-triazin-3-yl)pyrrolidin-3-amine (Intermediate 1, 200 mg, 1.21 mmol), and 5-bromo-1,3,4-thiadiazol-2-amine (218 mg, 1.21 mmol) in DMF (3 mL). The resulting solution was stirred at 100° C. for 1 h to give crude N'-[(3R)-1-(1,2,4-triazin-3-yl)pyrrolidin-3-yl]-1,3,4-thiadiazole-2,5-diamine. The reaction was cooled to r.t. and half of the solution used as follows.

HATU (0.274 g, 0.72 mmol) was added to 2-methoxy-2-(3-(trifluoromethoxy)phenyl)acetic acid (Intermediate 17, 150 mg, 0.60 mmol), N'-[(3R)-1-(1,2,4-triazin-3-yl)pyrrolidin-3-yl]-1,3,4-thiadiazole-2,5-diamine (159 mg, 0.60 mmol) and DIPEA (314 μL, 1.80 mmol) in DMF (1.5 mL) at r.t. under nitrogen. The resulting solution was stirred at r.t. for 2 h. The reaction mixture was evaporated to dryness and dissolved in MeOH (20 mL). The solution was purified by ion exchange chromatography, using an SCX2 column. The desired product was eluted from the column using 7M ammonia/MeOH and pure fractions were evaporated to dryness to afford crude product as a brown gum (196 mg). The material was then purified by chiral HPLC. Optimisation on the Agilent 1100, IA column (20 μm silica, 4.6 mm diameter, 250 mm length) showed that heptane/IPA, 75/25 gave the best separation. This method was used for preparative work. Fractions containing the desired compounds were evaporated to dryness to afford:

Example 8(b) as the first eluted isomer. The first eluted isomer was repurified by FCC, elution gradient 0 to 5% MeOH in EtOAc. Pure fractions were evaporated to dryness to afford the product as a pale yellow foam (34 mg, 11%). $^1$H NMR (400 MHz, CDCl$_3$, 30° C.) δ 2.17-2.29 (1H, m), 2.40 (1H, dtd), 3.49 (3H, s), 3.80 (3H, s), 3.96 (1H, s), 4.41-4.49 (1H, m), 4.92 (1H, s), 6.06 (1H, s), 7.21 (1H, dddd), 7.35 (1H, s), 7.38-7.46 (2H, m), 8.10 (1H, d), 8.49 (1H, d), 10.33 (1H, s); m/z: ES$^+$ [M+H]$^+$ 497.41.

Example 8(a) as the second eluted isomer (78 mg, 26%). $^1$H NMR (400 MHz, CDCl$_3$, 30° C.) δ 2.22 (1H, dq), 2.43 (1H, td), 3.49 (3H, s), 3.65-3.92 (3H, m), 3.99 (1H, s), 4.49 (1H, s), 4.87 (1H, s), 5.27 (1H, s), 7.22 (1H, d), 7.31 (1H, s), 7.41 (2H, dt), 8.12 (1H, d), 8.52 (1H, d), 9.88 (1H, s); m/z: ES$^+$ [M+H]$^+$ 497.55.

Examples 9(a) and 9(b)

(2S)-2-Methoxy-N-[5-[[(3R)-1-pyridazin-3-ylpyrrolidin-3-yl]amino]-1,3,4-thiadiazol-2-yl]-2-[3-(trifluoromethoxy)phenyl]acetamide and (2R)-2-Methoxy-N-[5-[[(3R)-1-pyridazin-3-ylpyrrolidin-3-yl]amino]-1,3,4-thiadiazol-2-yl]-2-[3-(trifluoromethoxy)phenyl]acetamide

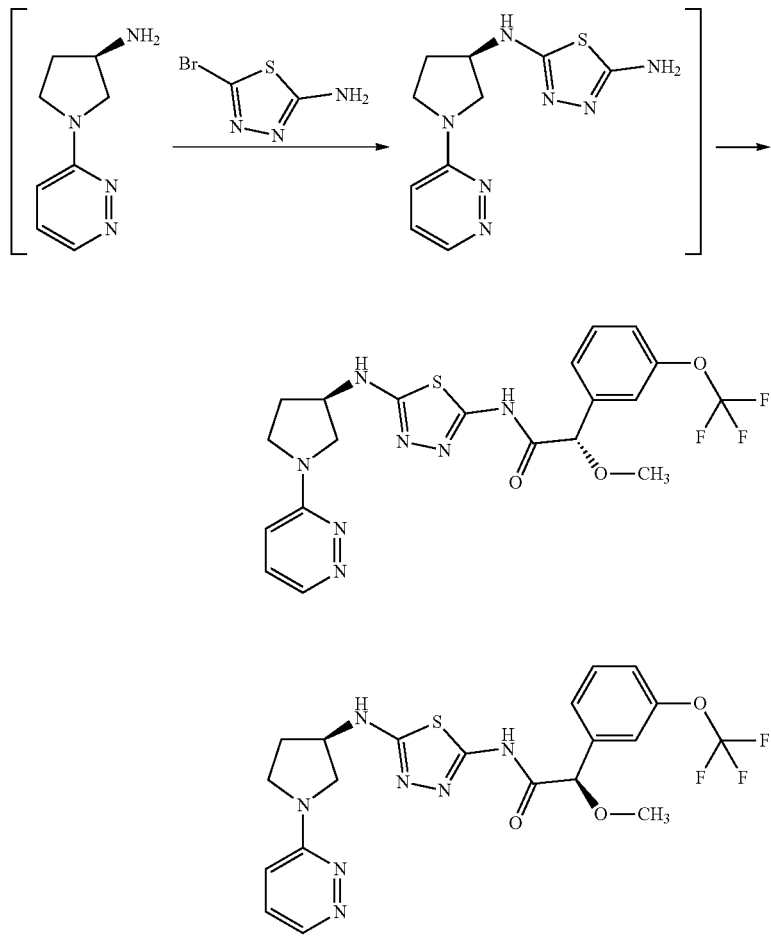

To a mixture of 5-bromo-1,3,4-thiadiazol-2-amine (330 mg, 1.83 mmol) and (3R)-1-pyridazin-3-ylpyrrolidin-3-amine dihydrochloride (Intermediate 6, 435 mg, 1.83 mmol) in DMF (4 mL) was added DIPEA (1.181 mL, 6.78 mmol) and the stirred suspension heated to 100° C. for 1 h. A solution of 2-methoxy-2-(3-(trifluoromethoxy)phenyl)acetic acid (Intermediate 17, 504 mg, 2.02 mmol) in DMF (1 mL) was then added followed by HATU (767 mg, 2.02 mmol) and the reaction was stirred overnight at r.t. The crude reaction mixture was then directly loaded onto an SCX column and the desired product was eluted from the column using 1M ammonia/MeOH and pure fractions were evaporated to dryness to afford product as a brown gum. The crude product was purified by preparative HPLC (Waters XBridge Prep C18 OBD column, 5 μm silica, 19 mm diameter, 100 mm length), using decreasingly polar mixtures of water (containing 1% ammonia) and MeCN as eluents. Fractions containing the desired compound were evaporated to dryness to afford the product as a mixture of diastereoisomers, (222 mg) that was further purified by chiral prep-HPLC as follows. The polar organic alcohols screen showed possible separation on the C2 column (3 μm silica, 4.6 mm diameter, 50 mm length) using a mixture of EtOH and MeOH as eluents (50/50). This method was used for preparative work on OD column (20 μm silica, 50 mm diameter, 250 mm length). Fractions containing the desired compounds were evaporated to dryness to afford:

Example 9(a) as the first eluted isomer (90 mg, 10%). $^1$H NMR (400 MHz, DMSO-d6, 30° C.) δ 2.02-2.13 (1H, m), 2.24-2.36 (1H, m), 3.35 (3H, s), 3.45-3.64 (3H, m), 3.76 (1H, dd), 4.33-4.45 (1H, m), 5.07 (1H, s), 6.86 (1H, dd), 7.28-7.40 (2H, m), 7.43-7.59 (3H, m), 7.69 (1H, d), 8.48 (1H, dd), 12.26 (1H, s); m/z: ES$^+$ [M+H]$^+$ 496.5.

Example 9(b) as the second eluted isomer (84 mg, 9%). $^1$H NMR (400 MHz, DMSO-d6, 30° C.) δ 1.99-2.13 (1H, m), 2.23-2.38 (1H, m), 3.35 (3H, s), 3.45-3.64 (3H, m), 3.76 (1H, dd), 4.33-4.46 (1H, m), 5.07 (1H, s), 6.86 (1H, dd), 7.29-7.39 (2H, m), 7.42-7.59 (3H, m), 7.69 (1H, d), 8.48 (1H, dd), 12.27 (1H, s); m/z: ES$^+$ [M+H]$^+$ 496.5.

Examples 10(a) and 10(b)

(2S)-2-Ethoxy-2-phenyl-N-[5-[[(3R)-1-pyridazin-3-ylpyrrolidin-3-yl]amino]-1,3,4-thiadiazol-2-yl]acetamide and (2R)-2-Ethoxy-2-phenyl-N-[5-[[(3R)-1-pyridazin-3-ylpyrrolidin-3-yl]amino]-1,3,4-thiadiazol-2-yl]acetamide

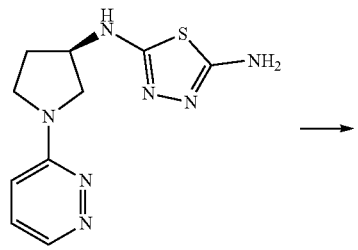

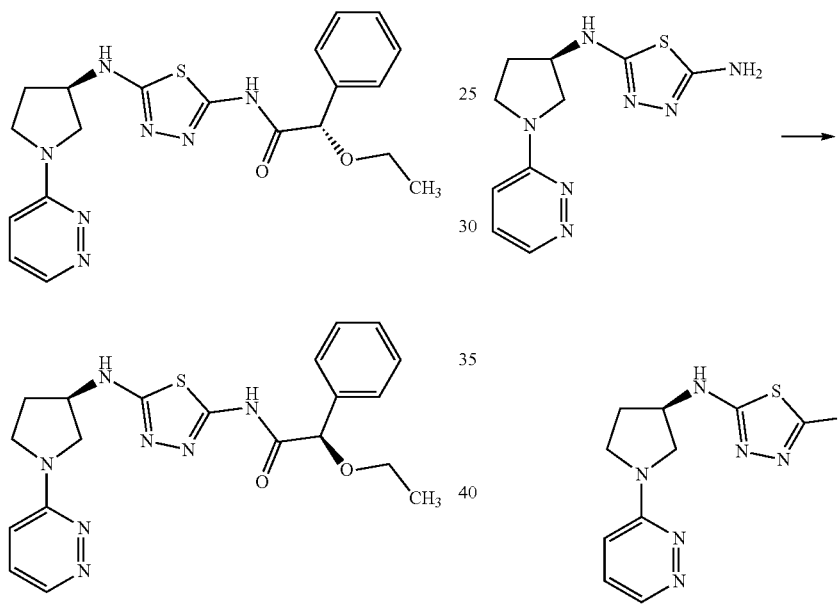

HATU (6.24 g, 16.41 mmol) was added to N'-[(3R)-1-pyridazin-3-ylpyrrolidin-3-yl]-1,3,4-thiadiazole-2,5-diamine (Intermediate 5, 3.6 g, 13.67 mmol), 2-ethoxy-2-phenylacetic acid (Intermediate 18, 2.464 g, 13.67 mmol) and DIPEA (2.381 mL, 13.67 mmol) in DMF (40 mL) at 21° C. under nitrogen. The resulting solution was stirred at 21° C. for 1.5 h. The crude product was purified by ion exchange chromatography, using an SCX column. The desired product was eluted from the column using 1M ammonia/MeOH and pure fractions were adsorbed onto silica. The crude product was purified by FCC, elution gradient 0 to 8% MeOH in DCM. Pure fractions were evaporated to dryness to afford the product as a mixture of diastereomers. Diastereomer separation was achieved on an AD column using 75/25, isopropanol/MeOH as eluents. The sample was dissolved in 30 mL of IPA/MeOH. Fractions containing the desired compounds were evaporated to dryness to afford:

Example 10(b) as the first eluted isomer (1.4 g, 24%). $^1$H NMR (400 MHz, DMSO-d6, 30° C.) δ 1.17 (3H, t), 2.06 (1H, m), 2.22-2.35 (1H, m), 3.38-3.60 (5H, m), 3.73 (1H, m), 4.31-4.50 (1H, m), 5.07 (1H, s), 6.85 (1H, dd), 7.25-7.41 (4H, m), 7.46 (2H, m), 7.67 (1H, d), 8.46 (1H, dd), 12.16 (1H, s); m/z: ES$^+$ [M+H]$^+$ 426.

Example 10(a) as the second eluted isomer (1.6 g, 27%). $^1$H NMR (400 MHz, DMSO-d6, 30° C.) δ 1.17 (3H, t), 2.06 (1H, m), 2.22-2.35 (1H, m), 3.38-3.60 (5H, m), 3.73 (1H, m), 4.31-4.50 (1H, m), 5.07 (1H, s), 6.85 (1H, dd), 7.25-7.41 (4H, m), 7.46 (2H, m), 7.67 (1H, d), 8.46 (1H, dd), 12.16 (1H, s); m/z: ES$^+$ [M+H]$^+$ 426.

Example 11

(2S)-2-Methoxy-2-(4-methoxyphenyl)-N-[5-[[(3R)-1-pyridazin-3-ylpyrrolidin-3-yl]amino]-1,3,4-thiadiazol-2-yl]acetamide (2S)-2-methoxy-2-(4-methoxyphenyl)acetic acid (Intermediate 19, 0.224 g, 1.14 mmol) was added to N'-[(3R)-1-pyridazin-3-ylpyrrolidin-3-yl]-1,3,4-thiadiazole-2,5-diamine (Intermediate 5, 0.3 g, 1.14 mmol), EDC (0.328 g, 1.71 mmol) and HOBT (0.174 g, 1.14 mmol) in DMF (5 mL). The resulting mixture was stirred at 25° C. for 16 h. The crude product was purified by preparative HPLC (Phenomenex Gemini-NX axia Prep C18 OBD column, 5 μm silica, 19 mm diameter, 100 mm length), using decreasingly polar mixtures of water (containing 1% NH$_4$HCO$_3$) and MeCN as eluents. Fractions containing the desired compound were evaporated to dryness to afford (2S)-2-methoxy-2-(4-methoxyphenyl)-N-[5-[[(3R)-1-pyridazin-3-ylpyrrolidin-3-yl]amino]-1,3,4-thiadiazol-2-yl]acetamide (50 mg, 10%) as a white solid. $^1$H NMR (300 MHz, DMSO-d6, 26° C.) δ 2.06 (1H, td), 2.19-2.37 (1H, m), 3.26 (3H, s), 3.41-3.61 (3H, m), 3.73 (4H, s), 4.37 (1H, q), 4.88 (1H, s), 6.80-6.98 (3H, m), 7.26-7.42 (3H, m), 7.64 (1H, d), 8.47 (1H, dd), 12.15 (1H, s); m/z: ES$^+$ [M+H]$^+$ 442.

Examples 12(a) and 12(b)

(2S)-2-(4-Fluorophenyl)-2-methoxy-N-[5-[[(3R)-1-pyridazin-3-ylpyrrolidin-3-yl]amino]-1,3,4-thiadiazol-2-yl]acetamide and (2R)-2-(4-Fluorophenyl)-2-methoxy-N-[5-[[(3R)-1-pyridazin-3-ylpyrrolidin-3-yl]amino]-1,3,4-thiadiazol-2-yl]acetamide

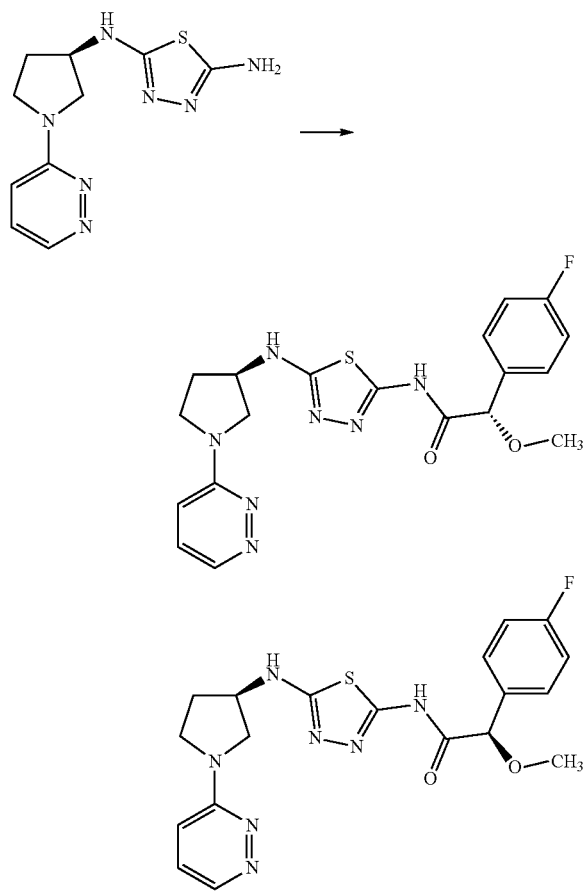

2-(4-Fluorophenyl)-2-methoxy-acetic acid (Intermediate 23, 0.11 g, 0.57 mmol) was suspended in DMF (5 mL) and cooled in an ice bath under nitrogen. DIPEA (0.3 mL, 1.71 mmol) was added, followed by HATU (0.22 g, 0.57 mmol). The mixture was stirred for 10 minutes (with ice bath cooling) before addition of N'-[(3R)-1-pyridazin-3-ylpyrrolidin-3-yl]-1,3,4-thiadiazole-2,5-diamine (Intermediate 5, 0.15 g, 0.57 mmol). The reaction was allowed to warm to r.t. and stirred for 5 h. It was then evaporated to dryness. The crude product was purified by ion exchange chromatography, using an SCX column. The desired product was eluted from the column using 2N ammonia/MeOH. The crude product was purified by FCC, eluent 7% MeOH in DCM. Pure fractions were evaporated to dryness to afford the product as a mixture of diastereoisomers. The mixture of diastereoisomers was separated by preparative chiral HPLC (Chiralpak IA column, 20 µm silica, 50 mm diameter, 250 mm length), Heptane/EtOH-MeOH 60/40 to give:

Example 12(b) as the first eluted isomer (47 mg, 35%). $^1$H NMR (500 MHz, DMSO-d6, 26° C.) δ 2.08 (1H, dt), 2.29 (1H, dtd), 3.47-3.63 (3H, m), 3.76 (1H, dd), 4.33-4.49 (1H, m), 5.00 (1H, s), 6.87 (1H, dd), 7.23 (2H, t), 7.33 (1H, dd), 7.46-7.55 (2H, m), 7.69 (1H, d), 8.48 (1H, dd), 12.22 (1H, s); m/z: ES$^+$ [M+H]$^+$ 430.

Example 12(a) as the second eluted isomer (49 mg, 36%). $^1$H NMR (500 MHz, DMSO-d6, 26° C.) δ 2.08 (1H, dd), 2.30 (1H, dd), 3.18 (2H, d), 3.45-3.62 (3H, m), 3.75 (1H, dd), 4.08 (1H, q), 4.33-4.44 (1H, m), 5.00 (1H, s), 6.86 (1H, dd), 7.22 (2H, t), 7.33 (1H, dd), 7.50 (2H, dd), 7.69 (1H, d), 8.48 (1H, dd), 12.21 (1H, s); m/z: ES$^+$ [M+H]$^+$ 430.

Examples 13(a) and 13(b)

(2S)-2-Ethoxy-2-(4-fluorophenyl)-N-[5-[[(3R)-1-pyridazin-3-ylpyrrolidin-3-yl]amino]-1,3,4-thiadiazol-2-yl]acetamide and (2R)-2-Ethoxy-2-(4-fluorophenyl)-N-[5-[[(3R)-1-pyridazin-3-ylpyrrolidin-3-yl]amino]-1,3,4-thiadiazol-2-yl]acetamide

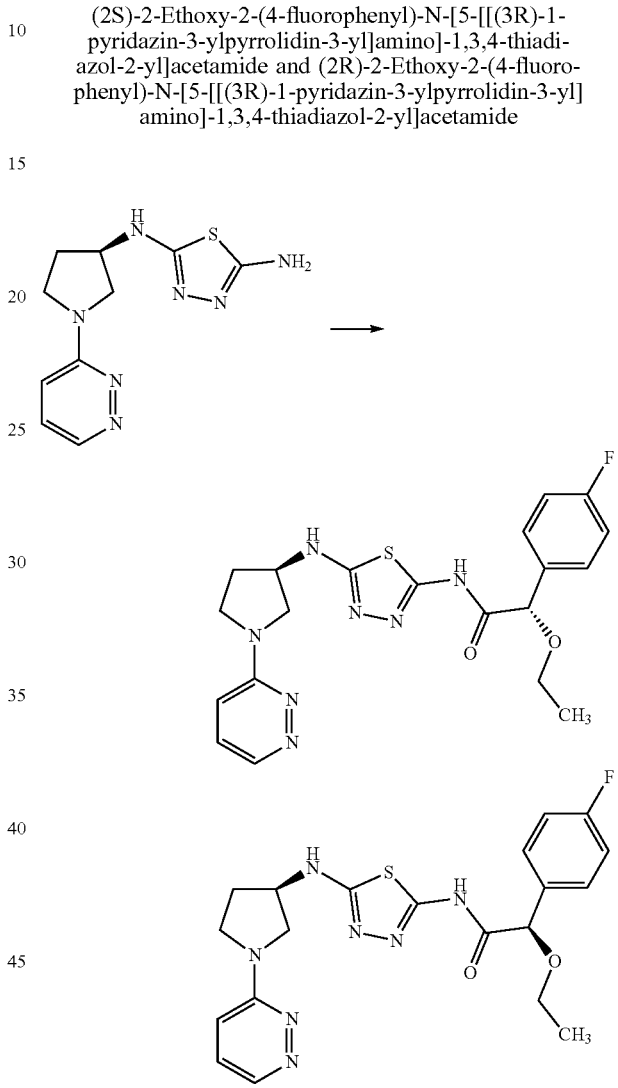

HATU (0.29 g, 0.76 mmol) was added to N'-[(3R)-1-pyridazin-3-ylpyrrolidin-3-yl]-1,3,4-thiadiazole-2,5-diamine (Intermediate 5, 0.2 g, 0.76 mmol), 2-ethoxy-2-(4-fluorophenyl)acetic acid (Intermediate 25, 0.15 g, 0.76 mmol) and DIPEA (0.4 mL, 2.279 mmol) in DMF (2 mL) at r.t. under nitrogen. The resulting solution was stirred at r.t. for 48 h. The reaction mixture was diluted with MeOH (1 mL) and passed through a 5 g SCX cartridge, washed with MeOH and then basic products eluted with 2N ammonia in MeOH. The basic fraction was evaporated and purified further by preparative HPLC (SunFire C18 column, 5 µm pore size, column of dimensions 50×19 mm, flow rate 25 mL/min and mobile phases of water and MeCN containing 0.1% formic acid. The elution was started at 95% water:5% MeCN and held at this for 0.3 minutes before increasing to 5% water:95% MeCN up to 5.8 mins before returning to the starting conditions over 0.1 minutes). Pure fractions were evaporated and passed through a 5 g SCX cartridge, washed with MeOH and then eluted with 2N ammonia in MeOH. The basic fraction was evaporated and dried overnight in vacuo to give the crude product as a mixture of diastereoisomers. The diastereoisomers were separated by preparative HPLC (Phenomenex Lux C2 column, 20 μm silica, 50 mm diameter, 250 mm length, EtOH 100%, 120 ml/min) to give:

Example 13(a) as the first eluted isomer (30 mg, 34%). $^1$H NMR (400 MHz, DMSO, 30° C.) δ 1.17 (3H, t), 2.01-2.11 (1H, m), 2.23-2.32 (1H, m), 3.37-3.59 (5H, m), 3.74 (1H, dd), 4.34-4.41 (1H, m), 5.08 (1H, s), 6.85 (1H, dd), 7.16-7.24 (2H, m), 7.31 (1H, dd), 7.46-7.53 (2H, m), 7.66 (1H, d), 8.46 (1H, dd), 12.16 (1H, s); m/z: ES$^+$ [M+H]$^+$ 444.

Example 13(b) as the second eluted isomer (34 mg, 37%). $^1$H NMR (400 MHz, DMSO, 27° C.) δ 1.17 (3H, t), 2-2.1 (1H, m), 2.22-2.31 (1H, m), 3.38-3.58 (5H, m), 3.74 (1H, dd), 4.33-4.41 (1H, m), 5.08 (1H, s), 6.85 (1H, dd), 7.16-7.24 (2H, m), 7.31 (1H, dd), 7.46-7.53 (2H, m), 7.65 (1H, d), 8.47 (1H, dd), 12.19 (1H, s); m/z: ES$^+$ [M+H]$^+$ 444.

Examples 14(a) and 14(b)

(2S)-2-(4-Fluoro-3-methoxy-phenyl)-2-methoxy-N-[5-[[(3R)-1-pyridazin-3-ylpyrrolidin-3-yl]amino]-1,3,4-thiadiazol-2-yl]acetamide and (2R)-2-(4-Fluoro-3-methoxy-phenyl)-2-methoxy-N-[5-[[(3R)-1-pyridazin-3-ylpyrrolidin-3-yl]amino]-1,3,4-thiadiazol-2-yl]acetamide

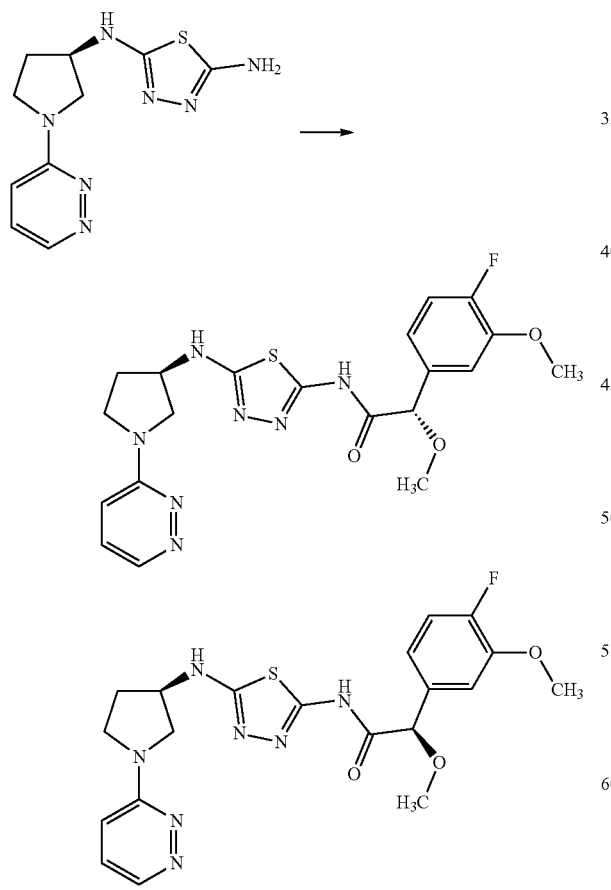

HATU (0.71 g, 1.868 mmol) was added to N'-[(3R)-1-pyridazin-3-ylpyrrolidin-3-yl]-1,3,4-thiadiazole-2,5-diamine (Intermediate 5, 0.25 g, 0.934 mmol) 2-(4-fluoro-3-methoxy-phenyl)-2-methoxy-acetic acid (Intermediate 26, 0.2 g, 0.934 mmol) and DIPEA (0.49 mL, 2.801 mmol) in DMF (5 mL) cooled in an ice bath under nitrogen. The resulting solution was stirred at r.t. overnight. Solvent was removed in vacuo and the residue taken up in MeOH and passed through a 5 g SCX cartridge washed with MeOH then eluted with 2N ammonia in MeOH. The basic fraction was evaporated and purified by FCC (0-8% MeOH in DCM) followed by preparative HPLC (SunFire C18 column, 5 μm pore size, dimensions 50×19 mm, flow rate 25 mL/min and mobile phases of water and MeCN containing 0.1% formic acid. The elution was started at 95% water:5% MeCN and held at this for 0.3 minutes before increasing to 5% water: 95% MeCN up to 5.8 mins before returning to the starting conditions over 0.1 minutes). Pure fractions were evaporated and passed through a 5 g SCX cartridge washed with MeOH then eluted with 2N ammonia in MeOH. The basic fraction was evaporated and dried overnight in vacuo to give the crude product as a mixture of diastereoisomers. The diastereoisomers were separated by preparative HPLC (C2 prep column, 50×250 mm, 20 m silica, eluting with a 50/50 mixture of EtOH/MeOH at 110 ml/min) to give:

Example 14(a) as the first eluted isomer (42 mg, 33%). $^1$H NMR (400 MHz, DMSO, 30° C.) δ 2.02-2.11 (1H, m), 2.23-2.32 (1H, m), 3.31 (3H, s), 3.48 (1H, dd), 3.52-3.59 (2H, m), 3.74 (1H, dd), 3.83 (3H, s), 4.33-4.42 (1H, m), 4.95 (1H, s), 6.85 (1H, dd), 7.01 (1H, ddd), 7.20 (1H, dd), 7.25 (1H, dd), 7.31 (1H, dd), 7.67 (1H, d), 8.47 (1H, dd), 12.15 (1H, s); m/z: ES$^+$ [M+H]$^+$ 460.

Example 14(b) as the second eluted isomer (46 mg, 36%). $^1$H NMR (400 MHz, DMSO, 30° C.) δ 2.01-2.11 (1H, m), 2.22-2.31 (1H, m), 3.31 (3H, s), 3.46-3.59 (3H, m), 3.74 (1H, dd), 3.83 (3H, s), 4.32-4.42 (1H, m), 4.94 (1H, s), 6.85 (1H, dd), 7.01 (1H, ddd), 7.20 (1H, dd), 7.25 (1H, dd), 7.32 (1H, dd), 7.65 (1H, d), 8.47 (1H, dd), 12.17 (1H, s); m/z: ES$^+$ [M+H]$^+$ 460.

Examples 15(a) and 15(b)

(2S)-2-[3-(Difluoromethoxy)phenyl]-2-ethoxy-N-[5-[[(3R)-1-pyridazin-3-ylpyrrolidin-3-yl]amino]-1,3,4-thiadiazol-2-yl]acetamide and (2R)-2-[3-(Difluoromethoxy)phenyl]-2-ethoxy-N-[5-[[(3R)-1-pyridazin-3-ylpyrrolidin-3-yl]amino]-1,3,4-thiadiazol-2-yl]acetamide

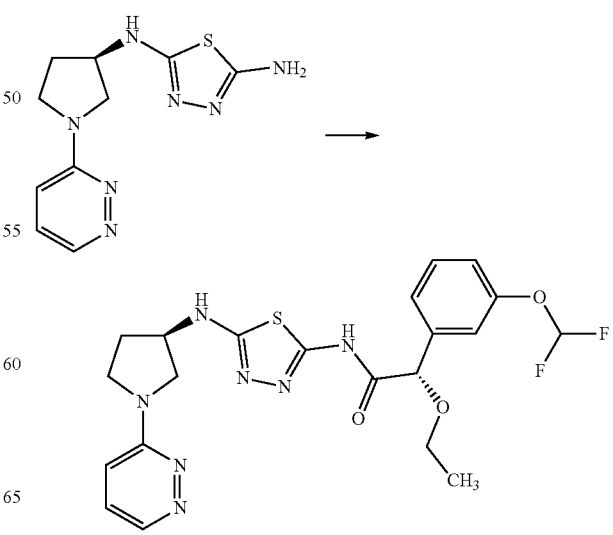

-continued

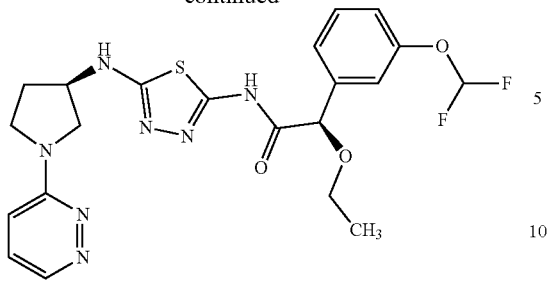

2-[3-(Difluoromethoxy)phenyl]-2-ethoxy-acetic acid (Intermediate 27, 0.14 g, 0.57 mmol) and N'-[(3R)-1-pyridazin-3-ylpyrrolidin-3-yl]-1,3,4-thiadiazole-2,5-diamine (Intermediate 5, 0.15 g, 0.57 mmol) were weighed into a round bottomed flask. DMF (3 mL) and DIPEA (0.18 g, 1.424 mmol) were added followed by HATU (0.22 g, 0.57 mmol) and the resultant solution was allowed to stir at r.t. under nitrogen for 3 h. The solvent was removed under reduced pressure and the residual gum was dissolved in DCM, adsorbed onto silica and purified by FCC (elution gradient 1-8% MeOH in DCM). Evaporation of the pure fractions under reduced pressure yielded a gum. The diastereoisomers were separated from this gum by preparative HPLC (Amy-C column, 5 μm pore size, 20 mm diameter, 250 mm length, eluting with MeOH/CO$_2$ 40% containing ammonia modifier) to give:

Example 15(a) as the first eluted isomer (25 mg, 8%). $^1$H NMR (400 MHz, DMSO-d6, 21° C.) δ 1.19 (3H, t), 2.01-2.14 (1H, m), 2.22-2.36 (1H, m), 3.62-3.38 (5H, m), 3.74 (1H, dd), 4.33-4.44 (1H, m), 5.12 (1H, s), 6.86 (1H, dd), 7.16 (1H, dd), 7.24 (1H, t), 7.26-7.30 (1H, m), 7.30-7.48 (3H, m), 7.72 (1H, d), 8.48 (1H, dd), 12.27 (1H, s). m/z: ES$^+$ [M+H]$^+$ 492.

Example 15(b) as the second eluted isomer (23 mg, 8%). $^1$H NMR (400 MHz, DMSO-d6, 21° C.) δ 1.19 (3H, t), 2.01-2.14 (1H, m), 2.22-2.36 (1H, m), 3.62-3.38 (5H, m), 3.74 (1H, dd), 4.33-4.44 (1H, m), 5.12 (1H, s), 6.87 (1H, dd), 7.16 (1H, dd), 7.25 (1H, t), 7.26-7.30 (1H, m), 7.30-7.48 (3H, m), 7.72 (1H, d), 8.48 (1H, dd), 12.27 (1H, s). m/z: ES$^+$ [M+H]$^+$ 492.

Examples 16(a) and 16(b)

(2S)-2-Ethoxy-N-[5-[[(3R)-1-pyridazin-3-ylpyrrolidin-3-yl]amino]-1,3,4-thiadiazol-2-yl]-2-[3-(trifluoromethoxy)phenyl]acetamide and (2R)-2-Ethoxy-N-[5-[[(3R)-1-pyridazin-3-ylpyrrolidin-3-yl]amino]-1,3,4-thiadiazol-2-yl]-2-[3-(trifluoromethoxy)phenyl]acetamide

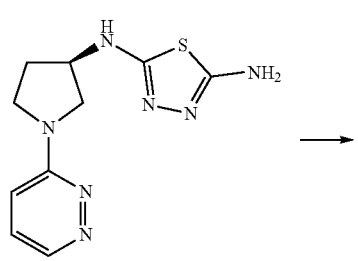

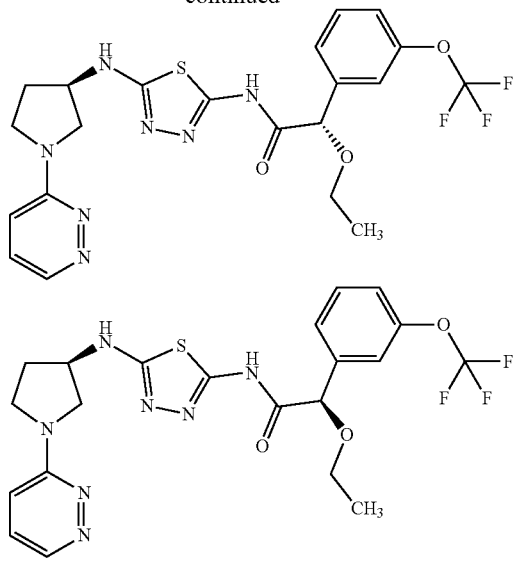

DIPEA (0.15 mL, 0.85 mmol), HATU (260 mg, 0.68 mmol) and 2-ethoxy-2-[3-(trifluoromethoxy)phenyl]acetic acid (Intermediate 28, 180 mg, 0.68 mmol) were added to a solution of N'-[(3R)-1-pyridazin-3-ylpyrrolidin-3-yl]-1,3,4-thiadiazole-2,5-diamine (Intermediate 5, 150 mg, 0.57 mmol) in DMF (4 mL). The mixture was stirred at r.t. for 18 h. This was then diluted with water (5 mL) and then extracted into DCM (10 mL), evaporated and purified by preparative HPLC (XBridge C18 column, 5 μm pore size, 50 mm length×19 mm diameter, flow rate 25 mL/min, mobile phase water containing 0.1% ammonium hydroxide and MeCN. The elution was started at 95% water:5% MeCN and held at this for 1.5 minutes ramping up to 5% water:95% MeCN over 8 minutes. The eluent was held at 95% MeCN until 12 minutes). Pure fractions were evaporated and passed through an SCX cartridge washing with MeOH and then eluting with 2M ammonia in MeOH. The basic fraction was evaporated and dried in vacuo to give the product as a mixture of diastereoisomers. The diastereoisomers were then separated by HPLC (Lux C4 column, 5 μm (20 mm diameter, 250 mm length, MeOH containing ammonia modifier, 21 mL/min) to give:

Example 16(a) as the first eluted isomer (46 mg, 16%). $^1$H NMR (400 MHz, DMSO-d6, 21° C.) δ 1.19 (3H, t), 1.97-2.15 (1H, m), 2.18-2.36 (1H, m), 3.40-3.65 (5H, m), 3.65-3.81 (1H, m), 4.32-4.46 (1H, m), 5.17 (1H, s), 6.87 (1H, dd), 7.28-7.40 (2H, m), 7.40-7.59 (3H, m), 7.74 (1H, d), 8.48 (1H, dd), 12.32 (1H, s); m/z: ES$^+$ [M+H]$^+$ 510.

Example 16(b) as the second eluted isomer (39 mg, 14%). $^1$H NMR (400 MHz, DMSO-d6, 21° C.) δ 1.19 (3H, t), 2.06 (1H, m), 2.20-2.35 (1H, m), 3.39-3.63 (5H, m), 3.74 (1H, m), 4.34-4.44 (1H, m), 5.17 (1H, s), 6.88 (1H, dd), 7.28-7.41 (2H, m), 7.42-7.58 (3H, m), 7.73 (1H, d), 8.48 (1H, d), 12.32 (1H, s); m/z: ES$^+$ [M+H]$^+$ 510.

The following Examples were prepared in an analogous fashion to Examples 1-16 using methods and reagents known to the skilled person with a common general knowledge of organic chemistry:

| Example No. | Structure | Name | Mass Spec Data m/z: ES+ [M + H]+ |
|---|---|---|---|
| 17(a) & 17(b) | 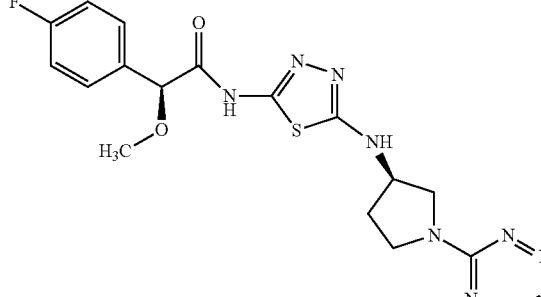 | (2S)-2-(4-fluorophenyl)-2-methoxy-N-[5-[[(3R)-1-(1,2,4-triazin-3-yl)pyrrolidin-3-yl]amino]-1,3,4-thiadiazol-2-yl]acetamide (2R)-2-(4-fluorophenyl)-2-methoxy-N-[5-[[(3R)-1-(1,2,4-triazin-3-yl)pyrrolidin-3-yl]amino]-1,3,4-thiadiazol-2-yl]acetamide | 431/431 |
| 18(a) & 18(b) | 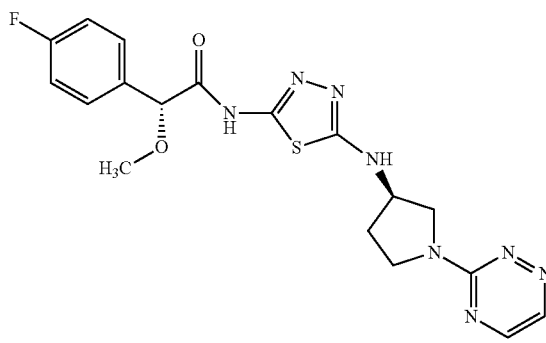 | (2S)-2-phenyl-N-[5-[[(3R)-1-pyridazin-3-ylpyrrolidin-3-yl]amino]-1,3,4-thiadiazol-2-yl]-2-(trideuteriomethoxy)acetamide; (2R)-2-phenyl-N-[5-[[(3R)-1-pyridazin-3-ylpyrrolidin-3-yl]amino]-1,3,4-thiadiazol-2-yl]-2-(trideuteriomethoxy)acetamide | 415/415 |

| Example No. | Structure | Name | Mass Spec Data m/z: ES+ [M + H]+ |
|---|---|---|---|
| 19(a) & 19(b) | 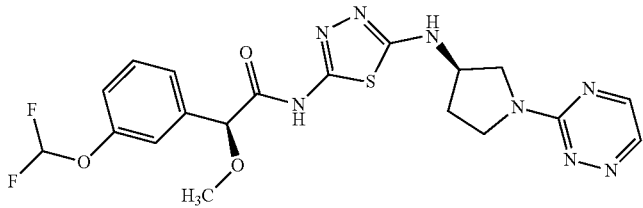 [SMILES: CO[C@H](C(=O)Nc1nnc(N[C@@H]2CCN(c3nccnn3)C2)s1)c1cccc(OC(F)F)c1] | (2S)-2-[3-(difluoromethoxy)phenyl]-2-methoxy-N-[5-[[(3R)-1-(1,2,4-triazin-3-yl)pyrrolidin-3-yl]amino]-1,3,4-thiadiazol-2-yl]acetamide (2R)-2-[3-(difluoromethoxy)phenyl]-2-methoxy-N-[5-[[(3R)-1-(1,2,4-triazin-3-yl)pyrrolidin-3-yl]amino]-1,3,4-thiadiazol-2-yl]acetamide | 479/479 |
| 20(a) & 20(b) | 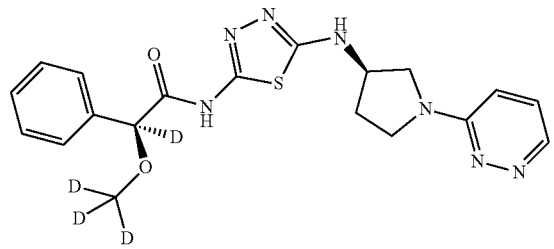 [SMILES: [2H]C([2H])([2H])O[C@]([2H])(C(=O)Nc1nnc(N[C@@H]2CCN(c3cccnn3)C2)s1)c1ccccc1] | (2S)-2-deuterio-2-phenyl-N-[5-[[(3R)-1-pyridazin-3-ylpyrrolidin-3-yl]amino]-1,3,4-thiadiazol-2-yl]-2-(trideuteriomethoxy)acetamide (2R)-2-deuterio-2-phenyl-N-[5-[[(3R)-1-pyridazin-3-ylpyrrolidin-3-yl]amino]-1,3,4-thiadiazol-2-yl]-2-(trideuteriomethoxy)acetamide | 416/416 |
| 21(a) & 21(b) | 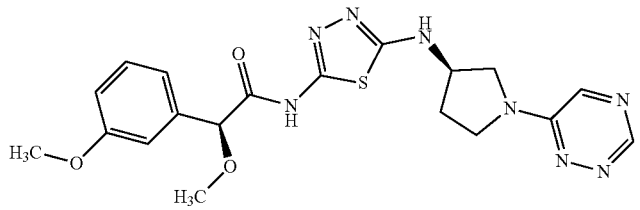 [SMILES: COc1cccc([C@H](OC)C(=O)Nc2nnc(N[C@@H]3CCN(c4cncnn4)C3)s2)c1] 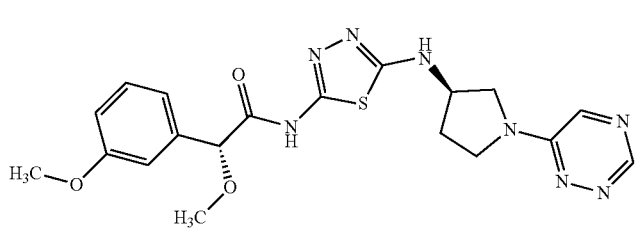 [SMILES: COc1cccc([C@@H](OC)C(=O)Nc2nnc(N[C@@H]3CCN(c4cncnn4)C3)s2)c1] | (2S)-2-methoxy-2-(3-methoxyphenyl)-N-[5-[[(3R)-1-(1,2,4-triazin-6-yl)pyrrolidin-3-yl]amino]-1,3,4-thiadiazol-2-yl]acetamide (2R)-2-methoxy-2-(3-methoxyphenyl)-N-[5-[[(3R)-1-(1,2,4-triazin-6-yl)pyrrolidin-3-yl]amino]-1,3,4-thiadiazol-2-yl]acetamide | 443/443 |

| Example No. | Structure | Name | Mass Spec Data m/z: ES+ [M + H]+ |
|---|---|---|---|
| 22(a) & 22(b) | 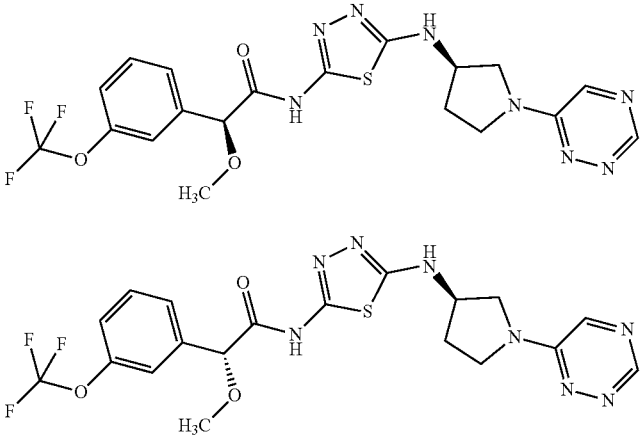 | (2S)-2-methoxy-N-[5-[[(3R)-1-(1,2,4-triazin-6-yl)pyrrolidin-3-yl]amino]-1,3,4-thiadiazol-2-yl]-2-[3-(trifluoromethoxy)phenyl]acetamide (2R)-2-methoxy-N-[5-[[(3R)-1-(1,2,4-triazin-6-yl)pyrrolidin-3-yl]amino]-1,3,4-thiadiazol-2-yl]-2-[3-(trifluoromethoxy)phenyl]acetamide | 497/497 |
| 23(a) & 23(b) | 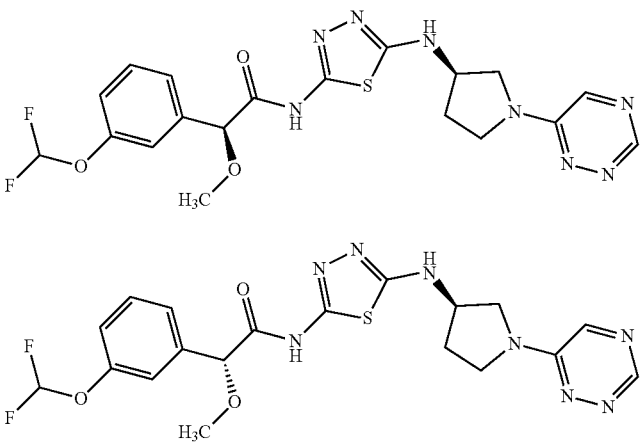 | (2S)-2-[3-(difluoromethoxy)phenyl]-2-methoxy-N-[5-[[(3R)-1-(1,2,4-triazin-6-yl)pyrrolidin-3-yl]amino]-1,3,4-thiadiazol-2-yl]acetamide (2R)-2-[3-(difluoromethoxy)phenyl]-2-methoxy-N-[5-[[(3R)-1-(1,2,4-triazin-6-yl)pyrrolidin-3-yl]amino]-1,3,4-thiadiazol-2-yl]acetamide | 479/479 |
| 24 | 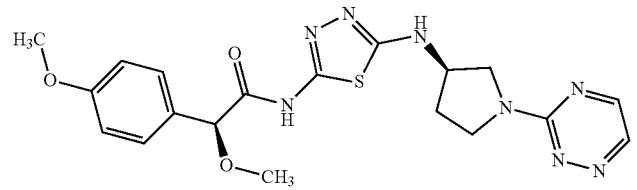 [SMILES: COc1ccc([C@H](OC)C(=O)Nc2nnc(N[C@@H]3CCN(c4nccnn4)C3)s2)cc1] | (2S)-2-methoxy-2-(4-methoxyphenyl)-N-[5-[[(3R)-1-(1,2,4-triazin-3-yl)pyrrolidin-3-yl]amino]-1,3,4-thiadiazol-2-yl]acetamide | |
| 25(a) & 25(b) | 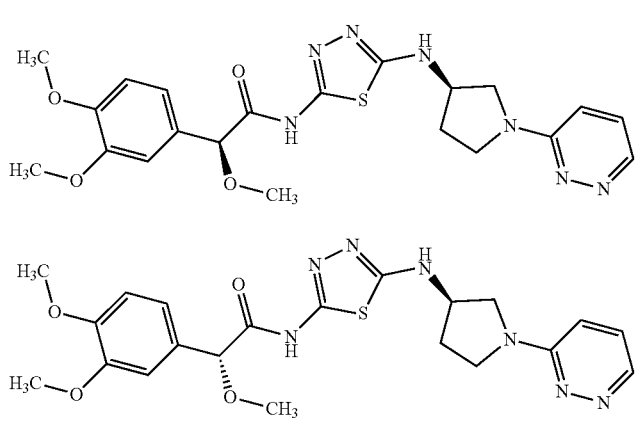 | (2S)-2-(3,4-dimethoxyphenyl)-2-methoxy-N-[5-[[(3R)-1-pyridazin-3-ylpyrrolidin-3-yl]amino]-1,3,4-thiadiazol-2-yl]acetamide (2R)-2-(3,4-dimethoxyphenyl)-2-methoxy-N-[5-[[(3R)-1-pyridazin-3-ylpyrrolidin-3-yl]amino]-1,3,4-thiadiazol-2-yl]acetamide | 472/472 |

-continued

| Example No. | Structure | Name | Mass Spec Data m/z: ES+ [M + H]+ |
|---|---|---|---|
| 26(a) & 26(b) | | (2S)-2-(3,4-dimethoxyphenyl)-2-methoxy-N-[5-[[(3R)-1-(1,2,4-triazin-3-yl)pyrrolidin-3-yl]amino]-1,3,4-thiadiazol-2-yl]acetamide (2R)-2-(3,4-dimethoxyphenyl)-2-methoxy-N-[5-[[(3R)-1-(1,2,4-triazin-3-yl)pyrrolidin-3-yl]amino]-1,3,4-thiadiazol-2-yl]acetamide | 473/473 |
| 27(a) & 27(b) | | (2S)-2-ethoxy-2-(3-methoxyphenyl)-N-[5-[[(3R)-1-(1,2,4-triazin-3-yl)pyrrolidin-3-yl]amino]-1,3,4-thiadiazol-2-yl]acetamide (2R)-2-ethoxy-2-(3-methoxyphenyl)-N-[5-[[(3R)-1-(1,2,4-triazin-3-yl)pyrrolidin-3-yl]amino]-1,3,4-thiadiazol-2-yl]acetamide | 457/457 |
| 28(a) & 28(b) | | (2S)-2-ethoxy-2-(4-methoxyphenyl)-N-[5-[[(3R)-1-pyridazin-3-ylpyrrolidin-3-yl]amino]-1,3,4-thiadiazol-2-yl]acetamide (2R)-2-ethoxy-2-(4-methoxyphenyl)-N-[5-[[(3R)-1-pyridazin-3-ylpyrrolidin-3-yl]amino]-1,3,4-thiadiazol-2-yl]acetamide | 456/456 |

| Example No. | Structure | Name | Mass Spec Data m/z: ES+ [M + H]+ |
|---|---|---|---|
| 29(a) & 29(b) | | (2S)-2-ethoxy-2-(4-methoxyphenyl)-N-[5-[[(3R)-1-(1,2,4-triazin-3-yl)pyrrolidin-3-yl]amino]-1,3,4-thiadiazol-2-yl]acetamide (2R)-2-ethoxy-2-(4-methoxyphenyl)-N-[5-[[(3R)-1-(1,2,4-triazin-3-yl)pyrrolidin-3-yl]amino]-1,3,4-thiadiazol-2-yl]acetamide | 457/457 |
| 30(a) & 30(b) | | (2S)-2-ethoxy-2-(3-methoxyphenyl)-N-[5-[[(3R)-1-pyridazin-3-ylpyrrolidin-3-yl]amino]-1,3,4-thiadiazol-2-yl]acetamide (2R)-2-ethoxy-2-(3-methoxyphenyl)-N-[5-[[(3R)-1-pyridazin-3-ylpyrrolidin-3-yl]amino]-1,3,4-thiadiazol-2-yl]acetamide | 456/456 |
| 31(a) & 31(b) | | (2S)-2-ethoxy-2-(4-fluoro-3-methoxy-phenyl)-N-[5-[[(3R)-1-pyridazin-3-ylpyrrolidin-3-yl]amino]-1,3,4-thiadiazol-2-yl]acetamide (2R)-2-ethoxy-2-(4-fluoro-3-methoxy-phenyl)-N-[5-[[(3R)-1-pyridazin-3-ylpyrrolidin-3-yl]amino]-1,3,4-thiadiazol-2-yl]acetamide | 474/474 |

| Example No. | Structure | Name | Mass Spec Data m/z: ES+ [M + H]+ |
|---|---|---|---|
| 32(a) & 32(b) | 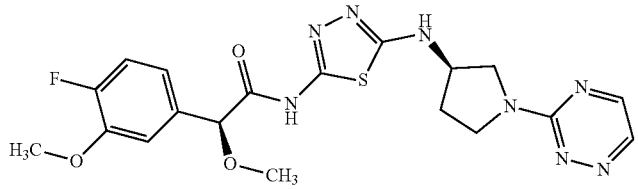 [SMILES: COc1cc([C@H](OC)C(=O)Nc2nnc(N[C@@H]3CCN(c4nccnn4)C3)s2)ccc1F]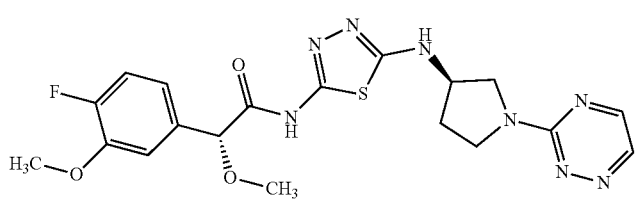 [SMILES: COc1cc([C@@H](OC)C(=O)Nc2nnc(N[C@@H]3CCN(c4nccnn4)C3)s2)ccc1F] | (2S)-2-(4-fluoro-3-methoxy-phenyl)-2-methoxy-N-[5-[[(3R)-1-(1,2,4-triazin-3-yl)pyrrolidin-3-yl]amino]-1,3,4-thiadiazol-2-yl]acetamide (2R)-2-(4-fluoro-3-methoxy-phenyl)-2-methoxy-N-[5-[[(3R)-1-(1,2,4-triazin-3-yl)pyrrolidin-3-yl]amino]-1,3,4-thiadiazol-2-yl]acetamide | 461/461 |
| 33(a) & 33(b) | 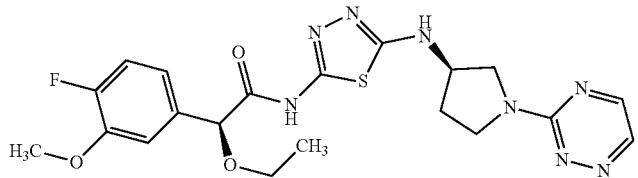 [SMILES: CCO[C@H](C(=O)Nc1nnc(N[C@@H]2CCN(c3nccnn3)C2)s1)c1ccc(F)c(OC)c1]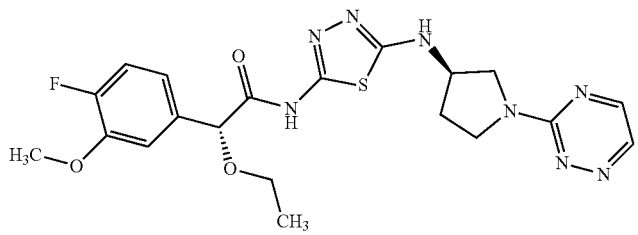 [SMILES: CCO[C@@H](C(=O)Nc1nnc(N[C@@H]2CCN(c3nccnn3)C2)s1)c1ccc(F)c(OC)c1] | (2S)-2-ethoxy-2-(4-fluoro-3-methoxy-phenyl)-N-[5-[[(3R)-1-(1,2,4-triazin-3-yl)pyrrolidin-3-yl]amino]-1,3,4-thiadiazol-2-yl]acetamide (2R)-2-ethoxy-2-(4-fluoro-3-methoxy-phenyl)-N-[5-[[(3R)-1-(1,2,4-triazin-3-yl)pyrrolidin-3-yl]amino]-1,3,4-thiadiazol-2-yl]acetamide | 475/475 |
| 34(a) & 34(b) | 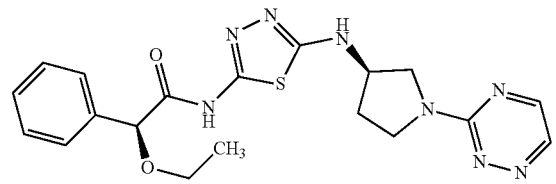 [SMILES: CCO[C@H](C(=O)Nc1nnc(N[C@@H]2CCN(c3nccnn3)C2)s1)c1ccccc1]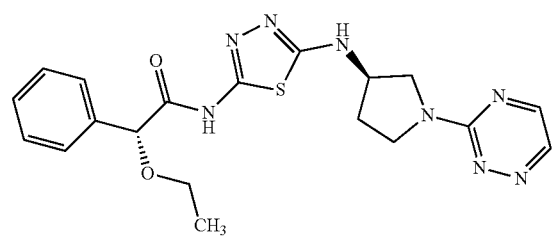 [SMILES: CCO[C@@H](C(=O)Nc1nnc(N[C@@H]2CCN(c3nccnn3)C2)s1)c1ccccc1] | (2S)-2-ethoxy-2-phenyl-N-[5-[[(3R)-1-(1,2,4-triazin-3-yl)pyrrolidin-3-yl]amino]-1,3,4-thiadiazol-2-yl]acetamide (2R)-2-ethoxy-2-phenyl-N-[5-[[(3R)-1-(1,2,4-triazin-3-yl)pyrrolidin-3-yl]amino]-1,3,4-thiadiazol-2-yl]acetamide | 427/427 |

| Example No. | Structure | Name | Mass Spec Data m/z: ES+ [M + H]+ |
|---|---|---|---|
| 35(a) & 34 (b) | 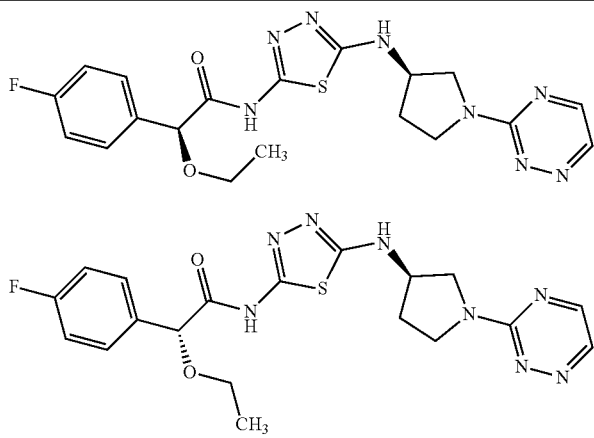 | (2S)-2-ethoxy-2-(4-fluorophenyl)-N-[5-[[(3R)-1-(1,2,4-triazin-3-yl)pyrrolidin-3-yl]amino]-1,3,4-thiadiazol-2-yl]acetamide (2R)-2-ethoxy-2-(4-fluorophenyl)-N-[5-[[(3R)-1-(1,2,4-triazin-3-yl)pyrrolidin-3-yl]amino]-1,3,4-thiadiazol-2-yl]acetamide | 445/445 |

Intermediate 1

(3R)-1-(1,2,4-Triazin-3-yl)pyrrolidin-3-amine

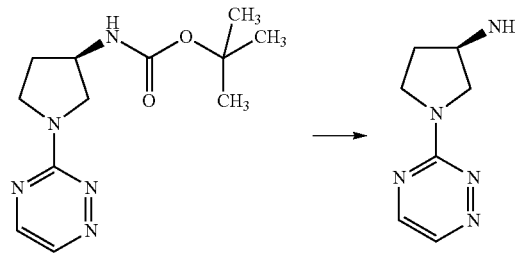

tert-Butyl N-[(3R)-1-(1,2,4-triazin-3-yl)pyrrolidin-3-yl] carbamate (Intermediate 2, 2.39 g, 9.01 mmol) was dissolved in a mixture of DCM (20 mL) and trifluoroacetic acid (5 mL) and the solution allowed to stand for 1 h at r.t. before being evaporated under reduced pressure. The residue was dissolved in MeOH and passed through a 20 g SCX cartridge flushing with MeOH followed by 3N ammonia in MeOH to bring off the product. The solvent was evaporated under reduced pressure to yield (3R)-1-(1,2,4-triazin-3-yl)pyrrolidin-3-amine (1.460 g, 98%) as a yellow solid. $^1$H NMR (400 MHz, CDCl$_3$, 27° C.) δ 1.8-1.92 (1H, m), 2.18-2.29 (1H, m), 3.45 (1H, s), 3.6-4.01 (4H, m), 8.13 (1H, d), 8.50 (1H, d); m/z: ES$^+$ [M+H]$^+$ 166.

Intermediate 2 tert-Butyl N-[(3R)-1-(1,2,4-Triazin-3-yl)pyrrolidin-3-yl]carbamate

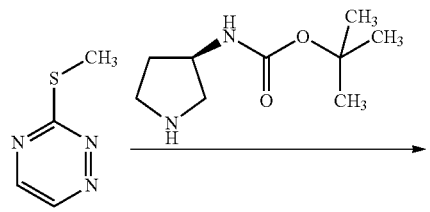

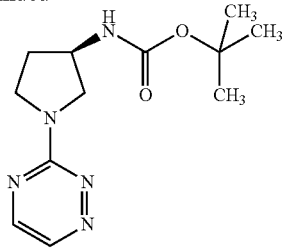

3-Methylsulfanyl-1,2,4-triazine (Intermediate 3, 1.5 g, 11.80 mmol), and tert-butyl N-[(3R)-pyrrolidin-3-yl]carbamate (2.64 g, 14.15 mmol) were dissolved in EtOH (12 mL) and sealed into a microwave tube. The reaction was heated to 100° C. for 24 h in the microwave reactor and cooled to r.t. LC/MS showed 61% product and 34% unreacted triazine. Further tert-butyl N-[(3R)-pyrrolidin-3-yl] carbamate (0.52 g) was added and heating at 100° C. in the microwave continued for 15 h. LC/MS showed 76% product and 18% unreacted triazine. The solvent was removed under reduced pressure and the residue partitioned between EtOAc and aqueous sodium bicarbonate. The aqueous layer was re-extracted with fresh EtOAc and the combined organics were dried (MgSO$_4$), filtered and evaporated under reduced pressure. The crude product was purified by FCC, elution gradient 0 to 80% EtOAc in heptane. Relevant fractions were evaporated to give tert-butyl N-[(3R)-1-(1,2,4-triazin-3-yl)pyrrolidin-3-yl]carbamate (2.390 g, 76%) as a yellow solid. $^1$H NMR (400 MHz, CDCl$_3$, 27° C.) δ 1.46 (9H, s), 1.96-2.07 (1H, m), 2.26-2.37 (1H, m), 3.55 (1H, s), 3.75 (2H, s), 3.90 (1H, s), 4.39 (1H, s), 4.69 (1H, s), 8.14 (1H, d), 8.53 (1H, d); m/z: ES$^-$ [M−H]$^-$ 264.

Intermediate 3

3-Methylsulfanyl-1,2,4-triazine

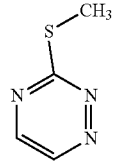

A solution of methyl hydrazinecarbimidothioate hydroiodide (Intermediate 4, 7.5 g, 32.18 mmol) in ice/water (400 mL) was added to a stirred solution of 40% oxalaldehyde (14.70 mL, 128.71 mmol), and sodium bicarbonate (6.76 g, 80.45 mmol) in ice/water (400 mL) cooled to 0° C. The resulting solution was stirred at 0° C. for 5 h, then extracted with DCM (2×150 mL). The extracts were combined washed with 1M citric acid (50 mL), dried over MgSO₄ and reduced to give 3-methylsulfanyl-1,2,4-triazine (3.60 g, 88%) as a yellow solid. ¹H NMR (400 MHz, CDCl₃, 27° C.) δ 2.68 (3H, s), 8.38 (1H, d), 8.94 (1H, d).

Intermediate 4

Methyl Hydrazinecarbimidothioate Hydroiodide

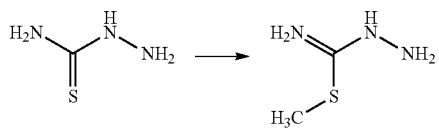

Iodomethane (0.623 mL, 10.00 mmol) was added to hydrazinecarbothioamide (0.911 g, 10 mmol), in EtOH (10 mL). The resulting mixture was stirred at 70° C. for 30 minutes. The reaction was allowed to cool to r.t. The reaction mixture was then filtered through a Nylon filtercup. The resultant solid was then washed with Et₂O and dried under vacuum overnight to give methyl hydrazinecarbimidothioate hydroiodide (1.810 g, 78%) as a white solid that was used without further purification.

Intermediate 5

N'-[(3R)-1-Pyridazin-3-ylpyrrolidin-3-yl]-1,3,4-thiadiazole-2,5-diamine

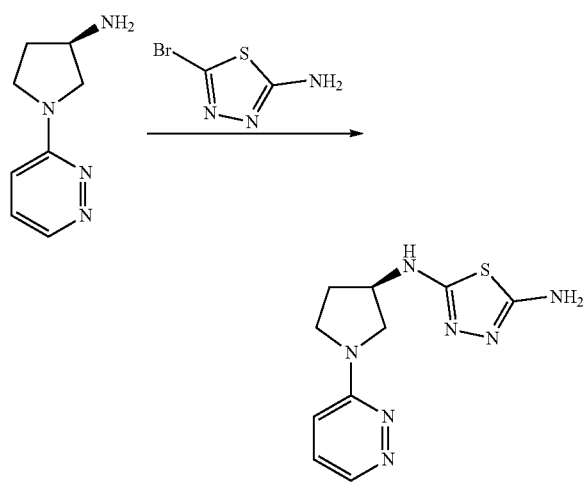

Into a 1000 mL round-bottom flask was placed a solution of (3R)-1-pyridazin-3-ylpyrrolidin-3-amine dihydrochloride (Intermediate 6, 10.5 g, 44.29 mmol) in DMF (400 mL), 5-bromo-1,3,4-thiadiazol-2-amine (7.94 g, 44.10 mmol) and DIPEA (17.07 g, 132.08 mmol). The resulting solution was stirred for 4 h at 80° C. The resulting mixture was concentrated under vacuum. The crude product was purified by re-crystallization from EtOH/EtOAc. This resulted in N'-[(3R)-1-pyridazin-3-ylpyrrolidin-3-yl]-1,3,4-thiadiazole-2,5-diamine as a light yellow solid (11 g, 94%). 1H NMR (500 MHz, DMSO-d6, 30° C.) δ 2.04 (1H, td), 2.22-2.31 (1H, m), 3.43-3.62 (3H, m), 3.72 (1H, dd), 4.28 (1H, dq), 6.27 (2H, s), 6.86 (1H, dd), 7.07 (1H, d), 7.33 (1H, dd), 8.48 (1H, dd); m/z: ES⁺ [M+H]⁺ 264.28.

Intermediate 5 was also prepared on a large scale according to the following alternative procedure.

(R)-1-(Pyridazin-3-yl)pyrrolidin-3-amine (Intermediate 6, free base form, 25.5 g, 150.63 mmol) and 5-bromo-1,3,4-thiadiazol-2-amine (29.8 g, 165.70 mmol) with DIPEA (39.4 mL, 225.95 mmol) was agitated as a slurry in MeOH (200 mL) at 45° C. The slurry was cooled to 20° C. and the solid isolated by vacuum filtration. 50 ml MeOH was used as a displacement wash of the filter cake and it was then dried overnight in the vacuum oven at 40° C. Intermediate 5 (32.9 g, 83%) was obtained as a free flowing beige powder.

Intermediate 6

(3R)-1-Pyridazin-3-ylpyrrolidin-3-amine dihydrochloride

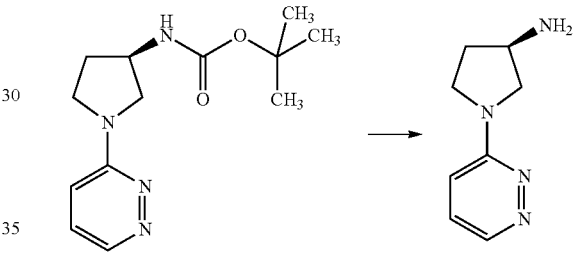

Into a 1000 mL round-bottom flask was placed a solution of tert-butyl N-[(3R)-1-pyridazin-3-ylpyrrolidin-3-yl]carbamate (Intermediate 7, 20 g, 75.66 mmol) in dioxane (200 mL) and conc. HCl (100 mL). The resulting solution was stirred for 30 mins at r.t. The resulting mixture was concentrated under vacuum. The crude product was re-crystallized from MeOH/EtOAc in the ratio of 1:2. This resulted in (3R)-1-pyridazin-3-ylpyrrolidin-3-amine dihydrochloride as an off-white solid (13.4 g, 75%). ¹H NMR (300 MHz, DMSO-d6, 26° C.) δ 2.25-2.43 (2H, m), 3.66-3.74 (1H, m), 3.78-3.90 (3H, m), 4.02-4.10 (1H, m), 7.75 (1H, d), 7.94 (1H, dd), 8.66 (1H, d), 8.77-8.98 (3H, br); m/z: ES⁺ [M+H]⁺ 165.

Intermediate 6 (free base form) was also prepared according to the following procedure.

tert-butyl N-[(3R)-1-(6-Chloropyridazin-3-yl)pyrrolidin-3-yl]carbamate (Intermediate 8, 20 g, 107.38 mmol) in pyridine (400 mL) was mixed with palladium hydroxide on carbon (Pearlman's Catalyst, 27.5 g, 25.84 mmol) and 1-Methyl-1,4-cyclohexadiene (31.0 ml, 276.13 mmol) in MeOH (1375 mL). The reaction mixture was then heated to 65° C. for 90 minutes. With complete conversion observed, the reaction was cooled back to r.t. and the catalyst removed by filtration. 3M Hydrochloric acid in MeOH (184 ml, 552.27 mmol) was then charged to the reaction mixture, and the solution heated to 65° C. for 1 h. With complete conversion observed, the reaction solution was cooled back to ambient and passed through 10×50 g SCX column which had been pre-eluted with MeOH. The compound was released from the SCX column via 1M ammonia in MeOH.

The resulting solution was diluted with toluene (1000 mL) and concentrated to dryness via rotary evaporation to give a free flowing solid. (3R)-1-Pyridazin-3-ylpyrrolidin-3-amine was isolated at a strength of 97% w/w as the free base.

Intermediate 7 tert-Butyl N-[(3R)-1-pyridazin-3-ylpyrrolidin-3-yl]carbamate

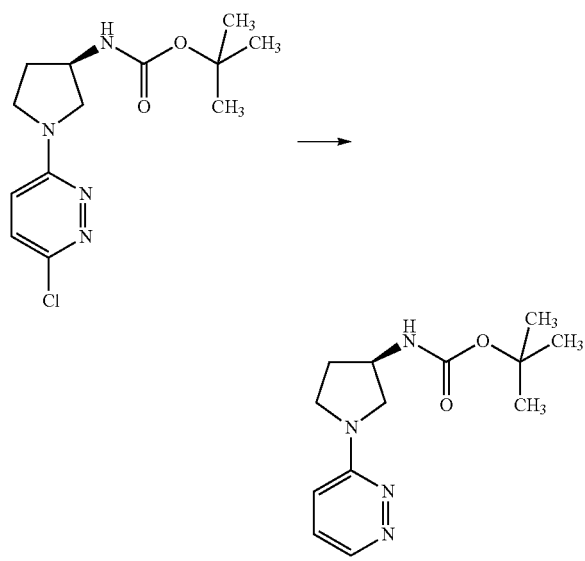

Into a 2000-mL round-bottom flask was placed a solution of tert-butyl N-[(3R)-1-(6-chloropyridazin-3-yl)pyrrolidin-3-yl]carbamate (Intermediate 8, 23 g, 76.98 mmol) in MeOH (800 mL) and palladium on carbon (2 g). The system was purged and maintained with hydrogen gas. The resulting solution was stirred for 4 h at r.t. The solids were filtered out. The resulting mixture was concentrated under vacuum. This resulted in tert-butyl N-[(3R)-1-pyridazin-3-ylpyrrolidin-3-yl]carbamate (20 g, 84%) as a yellow solid. $^1$H NMR (300 MHz, CDCl$_3$, 24° C.): δ 1.44 (9H, s), 2.25-2.35 (2H, m), 3.48-3.56 (1H, m), 3.70-4.10 (3H, m), 4.35-4.42 (1H, m), 7.26-7.32 (1H, m), 7.70-7.75 (1H, m), 8.53-8.55 (1H, m); m/z: ES$^+$ [M+H]$^+$ 265.

Intermediate 8 tert-Butyl N-[(3R)-1-(6-chloropyridazin-3-yl)pyrrolidin-3-yl]carbamate

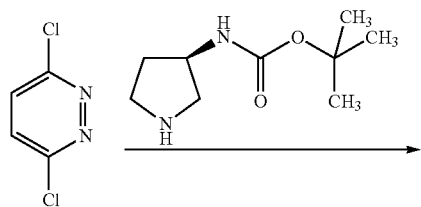

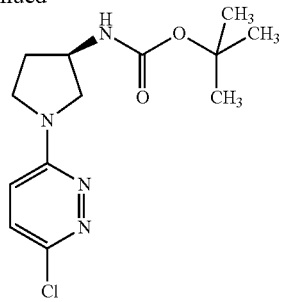

Into a 1000 mL round-bottom flask was placed a solution tert-butyl N-[(3R)-pyrrolidin-3-yl]carbamate (20 g, 107.38 mmol) in pyridine (400 mL) and 3,6-dichloropyridazine (16 g, 107.40 mmol). The resulting solution was heated to reflux for overnight. The resulting mixture was concentrated under vacuum. The crude product was purified by re-crystallization from EtOH/Et$_2$O in the ratio of 1:3. This resulted in tert-butyl N-[(3R)-1-(6-chloropyridazin-3-yl)pyrrolidin-3-yl]carbamate (23 g, 72%) as a yellow solid. $^1$H NMR (400 MHz, CDCl$_3$, 30° C.) δ 1.45 (9H, s), 2.02 (1H, dq), 2.31 (1H, td), 3.41 (1H, dd), 3.54-3.70 (2H, m), 3.78 (1H, dd), 4.37 (1H, s), 4.76 (1H, s), 6.61 (1H, d), 7.17 (1H, d); m/z: ES$^+$ [M+H]$^+$ 299.

Intermediate 9

N'-[(3R)-1-(1,2,4-Triazin-6-yl)pyrrolidin-3-yl]-1,3,4-thiadiazole-2,5-diamine

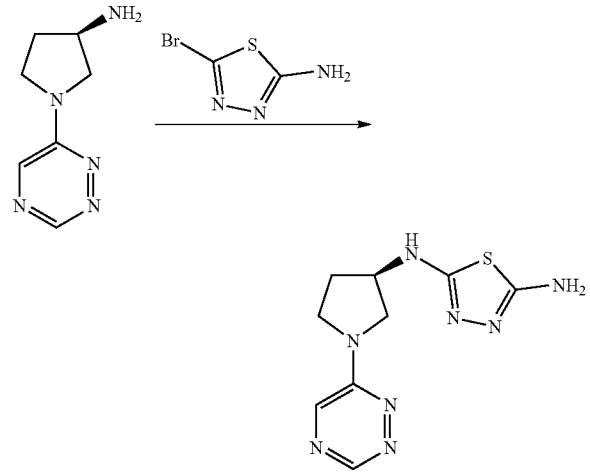

5-Bromo-1,3,4-thiadiazol-2-amine (177 mg, 0.99 mmol), (3R)-1-(1,2,4-triazin-6-yl)pyrrolidin-3-amine (Intermediate 10, 155 mg, 0.94 mmol) and DIPEA (0.196 mL, 1.13 mmol) were dissolved in DMF (4 mL) and sealed into a microwave tube. The reaction was heated to 100° C. for 90 minutes in the microwave reactor. The mixture was cooled to r.t. and diluted with MeOH (4 mL) before being passed through a 10 g SCX cartridge, flushing with MeOH followed by 3N methanolic ammonia to bring off the product. The solvent was evaporated under reduced pressure and the residue triturated with MeCN (10 mL) to yield N'-[(3R)-1-(1,2,4-triazin-6-yl)pyrrolidin-3-yl]-1,3,4-thiadiazole-2,5-diamine (198 mg, 80%) as a solid. $^1$H NMR (400 MHz, DMSO-d6, 27° C.) δ 1.99-2.10 (1H, m), 2.19-2.3 (1H, m), 3.51 (1H, dd), 3.59 (2H, t), 3.74 (1H, dd), 4.24-4.33 (1H, m), 6.28 (2H, s), 7.07 (1H, d), 8.26 (1H, s), 8.94 (1H, s); m/z: ES⁺ [M+H]⁺ 265.

Intermediate 10

(3R)-1-(1,2,4-Triazin-6-yl)pyrrolidin-3-amine

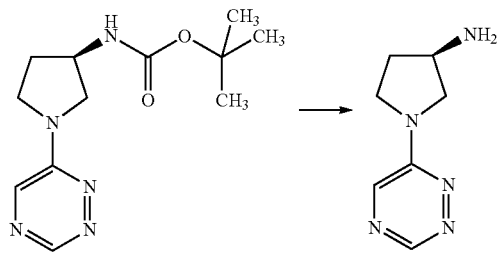 [SMILES: CC(C)(C)OC(=O)N[C@@H]1CCN(c2cncnn2)C1 ; N[C@@H]1CCN(c2cncnn2)C1]

tert-Butyl N-[(3R)-1-(1,2,4-triazin-6-yl)pyrrolidin-3-yl]carbamate (Intermediate 11, 280 mg, 1.06 mmol) was dissolved in a mixture of DCM (4 mL) and TFA (1 mL) and the solution allowed to stir for 1 h at r.t. before being evaporated under reduced pressure. The residue was dissolved in MeOH and passed through a 10 g SCX cartridge flushing with MeOH followed by 3N ammonia in MeOH to bring off the product. The solvent was evaporated under reduced pressure to yield (3R)-1-(1,2,4-triazin-6-yl)pyrrolidin-3-amine (155 mg, 89%) as a yellow solid. ¹H NMR (400 MHz, DMSO-d6, 27° C.) δ 1.69-1.79 (1H, m), 1.88 (2H, s), 2.00-2.10 (1H, m), 3.13-3.21 (1H, m), 3.44-3.53 (1H, m), 3.54-3.65 (3H, m), 8.20 (1H, s), 8.90 (1H, s); m/z: ES⁺ [M+H]⁺ 166.

Intermediate 11 tert-Butyl N-[(3R)-1-(1,2,4-triazin-6-yl)pyrrolidin-3-yl]carbamate

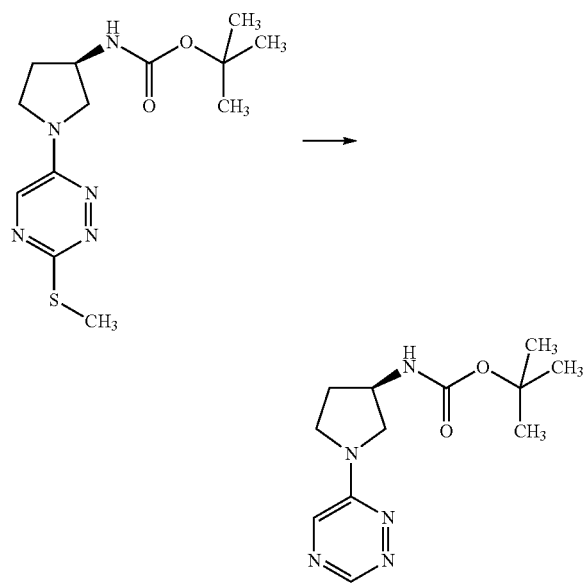

A mixture of tert-butyl N-[(3R)-1-(3-methylsulfanyl-1,2,4-triazin-6-yl)pyrrolidin-3-yl]carbamate (Intermediate 12, 1.7 g, 5.46 mmol) and Raney nickel (approx 50% aqueous mixture with aluminium) (0.935 g, 5.46 mmol) in EtOH (50 mL) was heated at reflux under nitrogen for 3 h. The catalyst was filtered off and the solvent removed under reduced pressure. The crude product was purified by FCC, elution gradient 0 to 5% MeOH in DCM. Pure fractions were evaporated to dryness to afford tert-butyl N-[(3R)-1-(1,2,4-triazin-6-yl)pyrrolidin-3-yl]carbamate (0.180 g, 12%) as a solid along with unreacted starting material (0.98 g). ¹H NMR (400 MHz, DMSO-d6, 27° C.) δ 1.39 (9H, s), 1.92 (1H, td), 2.14 (1H, dq), 3.32-3.37 (1H, m), 3.46-3.62 (2H, m), 3.67 (1H, dd), 4.09-4.21 (1H, m), 7.22 (1H, d), 8.23 (1H, s), 8.93 (1H, s); m/z: ES⁺ [M+H]⁺ 266.

Intermediate 12 tert-Butyl N-[(3R)-1-(3-methylsulfanyl-1,2,4-triazin-6-yl)pyrrolidin-3-yl]carbamate

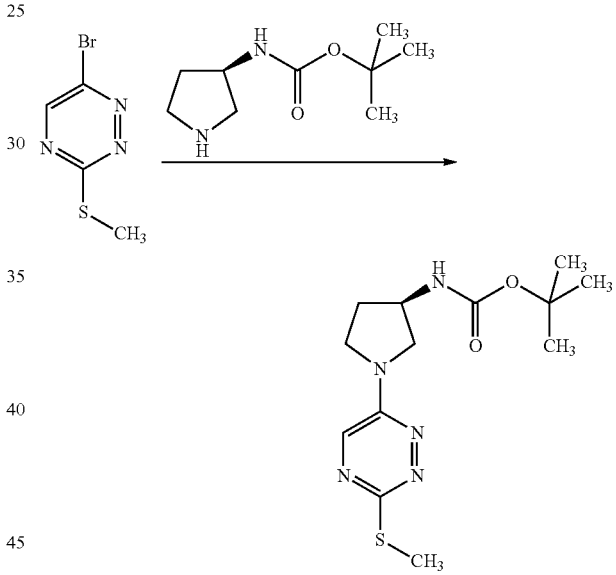

A mixture of tert-butyl N-[(3R)-pyrrolidin-3-yl]carbamate (1.452 g, 7.79 mmol) and 6-bromo-3-methylsulfanyl-1,2,4-triazine (Intermediate 13, 1.46 g, 7.09 mmol) and DIPEA (3.71 mL, 21.26 mmol) in butan-1-ol (15 mL) was heated at 80° C. under nitrogen for 3 h. The mixture was cooled to r.t. and the solvent evaporated under reduced pressure. The residue was partitioned between EtOAc and brine, the aqueous layer was re-extracted with fresh EtOAc and the combined organics were dried (MgSO₄), filtered and evaporated under reduced pressure. The crude solid was triturated with Et₂O (15 mL) to yield tert-butyl N-[(3R)-1-(3-methylsulfanyl-1,2,4-triazin-6-yl)pyrrolidin-3-yl]carbamate (1.750 g, 79%) as a yellow solid. ¹H NMR (400 MHz, CDCl₃, 27° C.) 1.46 (9H, s), δ 1.97-2.08 (1H, m), 2.27-2.40 (1H, m), 2.63 (3H, s), 3.43 (1H, dd), 3.58-3.72 (2H, m), 3.80 (1H, dd), 4.39 (1H, s), 4.66 (1H, s), 7.91 (1H, s); m/z: ES⁺ [M+H]⁺ 312.

Intermediate 13

6-Bromo-3-methylsulfanyl-1,2,4-triazine

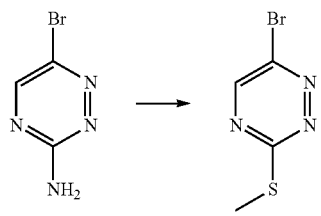

tert-Butyl nitrite (7.59 mL, 63.78 mmol) was added dropwise to a mixture of 6-bromo-1,2,4-triazin-3-amine (Intermediate 14, 1.86 g, 10.63 mmol) and 1,2-dimethyldisulfane (9.45 mL, 106.29 mmol) in dry MeCN (30 mL) and the reaction mixture then stirred at r.t. for 1 h. MeOH (3 mL) was added and the mixture evaporated under reduced pressure. The crude product was purified by FCC, elution gradient 0-20% EtOAc in heptane. Fractions containing product were evaporated under reduced pressure to yield 6-bromo-3-methylsulfanyl-1,2,4-triazine (1.520 g, 69%) as a yellow gum which crystallised on standing. $^1$H NMR (400 MHz, CDCl$_3$, 27° C.) δ 2.66 (3H, s), 8.43 (1H, s); m/z: ES$^+$ [M+H]$^+$ 205.9.

Intermediate 14

6-Bromo-1,2,4-triazin-3-amine

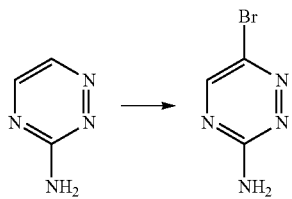 [SMILES: Nc1nccnn1 ; Nc1ncc(Br)nn1]

1-Bromopyrrolidine-2,5-dione (8.13 g, 45.68 mmol) was added portionwise to 1,2,4-triazin-3-amine (4.18 g, 43.50 mmol) in MeCN (48 mL) and water (72 mL) cooled to 0° C. The resulting solution was stirred at 0° C. for 10 minutes, then allowed to warm to r.t. and stirred for 90 minutes. The reaction was then cooled to 0° C. and EtOAc (150 mL) and sodium carbonate (3.23 g, 30.45 mmol) added, and the mixture was stirred for 5 minutes at 0° C. and then for 10 minutes at r.t. The organic layer was separated and the aqueous re-extracted with fresh EtOAc, the combined organics were washed with aqueous sodium bicarbonate, dried (MgSO$_4$), filtered and evaporated under reduced pressure. The crude solid was triturated with MeCN (20 mL) followed by EtOH (5 mL) to yield 6-bromo-1,2,4-triazin-3-amine (2.97 g, 39%) as a solid. $^1$H NMR (400 MHz, DMSO-d6, 27° C.) δ 7.45 (2H, s), 8.39 (1H, s); m/z: ES$^-$ [M-H]$^-$ 173

Intermediate 15

2-Methoxy-2-(3-methoxyphenyl)acetic acid

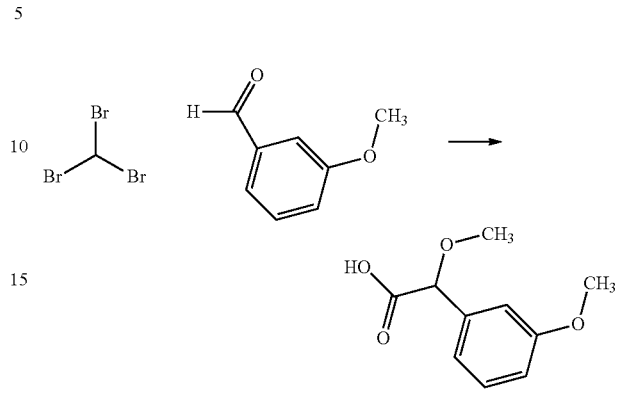

A solution of potassium hydroxide (2.267 g, 40.40 mmol) in MeOH (10 mL) was added over 2 h in small portions to a stirred mixture of 3-methoxybenzaldehyde (1 g, 7.34 mmol) and bromoform (0.771 mL, 8.81 mmol) in MeOH (5.00 mL) at 0° C. The mixture was then allowed to warm to r.t. and left to stir overnight. The solids were filtered under reduced pressure, rinsing the solids with MeOH (15 mL). The filtrate was evaporated to a thick white paste then re-dissolved in water (50 mL). This was then washed with Et$_2$O (50 mL) and then the aqueous portion was acidified to pH 2 (~5 mL 2M HCl solution). The aqueous phase was then extracted with EtOAc (3×50 mL). The combined organics were dried over MgSO$_4$ and filtered then solvents were evaporated under reduced pressure to give 2-methoxy-2-(3-methoxyphenyl)acetic acid as a yellow oil (1.4 g, 97%) that was used without further purification. $^1$H NMR (400 MHz, DMSO-d6, 30° C.) δ 3.18 (3H, s), 3.75 (3H, s), 4.74 (1H, s), 6.82-7.05 (3H, m), 7.29 (1H, m), 12.78 (1H, s).

Intermediate 16

2-[3-(Difluoromethoxy)phenyl]-2-methoxyacetic acid

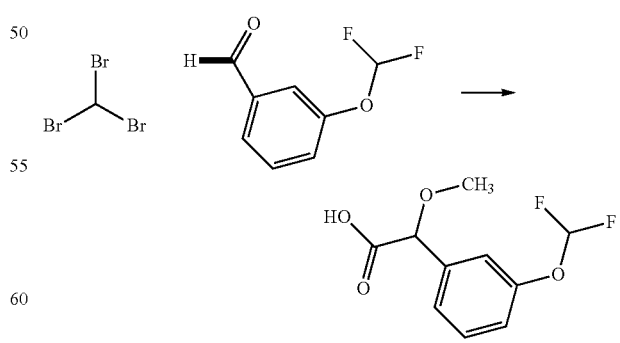

Solid potassium hydroxide (5.38 g, 95.86 mmol) was added portionwise over 1 h to a stirred solution of 3-(difluoromethoxy)benzaldehyde (3 g, 17.43 mmol), bromoform (1.829 mL, 20.91 mmol) and anhydrous MeOH (25 mL) at 0° C. The cooling bath was removed and the reaction was stirred at r.t. (a strong exothermic reaction started). The reaction was left stirring overnight. The inorganic solid was filtered off and washed with MeOH. The filtrate was concentrated in vacuo to small volume, diluted with water (100 mL) and washed twice with Et$_2$O (2×50 mL) and acidified to pH=2 by slow addition of 37% HCl. The mixture was extracted with EtOAc (3×50 mL). The organic layer was dried over Na$_2$SO$_4$, filtered and evaporated to afford crude product. The crude product was purified by FCC, elution gradient 0 to 60% EtOAc in heptane with 0.5% of formic acid. Pure factions were evaporated to dryness to afford 2-[3-(difluoromethoxy)phenyl]-2-methoxyacetic acid (1.710 g, 42%) as a gum. $^1$H NMR (400 MHz, DMSO-d6, 30° C.) 3.33 (3H, s), 4.82 (1H, s), 7.16 (2H, dd), 7.28 (1H, d), 7.23 (1H, t), 7.42-7.47 (1H, m), 12.93 (1H, s); m/z: ES$^-$ [M−H]$^-$ 231.25.

Intermediate 17

2-Methoxy-2-[3-(trifluoromethoxy)phenyl]acetic acid

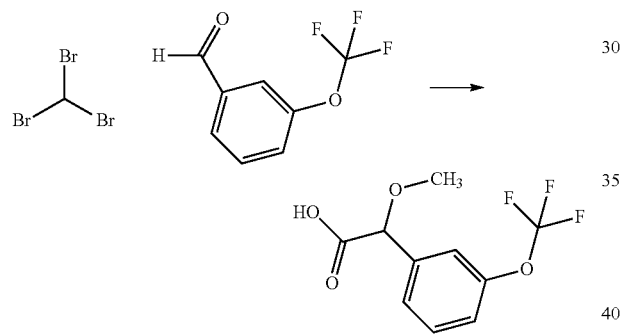

A solution of potassium hydroxide (1.851 g, 33.00 mmol) in MeOH (10 mL) was added over 2 h in small portions to a stirred mixture of 3-(trifluoromethoxy)benzaldehyde (1.141 g, 6 mmol) and bromoform (0.630 mL, 7.20 mmol) in MeOH (5.00 mL) at 0° C. The mixture was then allowed to warm to r.t. and left to stir overnight. A white precipitate had formed in the reaction mixture. Solids were filtered under reduced pressure, rinsing the solids with MeOH (15 mL). The filtrate solution was evaporated to a thick white paste then re-dissolved in water (50 mL). This was then washed with Et$_2$O (50 mL) and then the aqueous phase was acidified to pH 2 (~5 mL 2M HCl solution) giving a cloudy aqueous layer. The aqueous phase was extracted into EtOAc (3×50 mL). The combined organics were dried over MgSO$_4$ and filtered then solvents were evaporated under reduced pressure to give a clear oil. The crude product was purified by FCC, elution gradient 10 to 50% EtOAc in heptane. Pure fractions were evaporated to dryness to afford 2-methoxy-2-[3-(trifluoromethoxy)phenyl]acetic acid (0.832 g, 55%) as a colourless oil. $^1$H NMR (400 MHz, CDCl$_3$, 30° C.) δ 3.47 (3H, s), 4.81 (1H, s), 7.20-7.24 (1H, m), 7.33 (1H, s), 7.37-7.46 (2H, m); m/z: ES$^-$ [M−H]$^-$ 249.4.

Intermediate 18

2-Ethoxy-2-phenylacetic acid

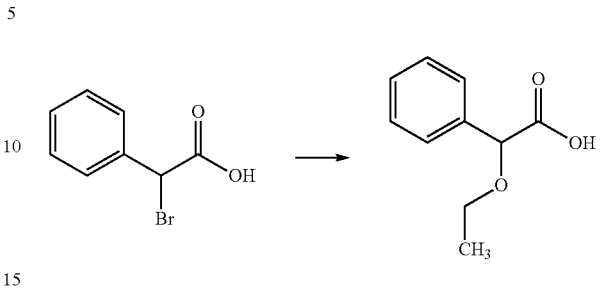

To a suspension of sodium hydride 60% (3.25 g, 81.38 mmol) in dry THF (70 mL) at 10° C. was added dropwise over 20 minutes a solution of EtOH (1.425 mL, 24.41 mmol) in dry THF (70 mL). The mixture was then treated dropwise with a solution of 2-bromo-2-phenylacetic acid (3.5 g, 16.28 mmol) in dry THF (20 mL) over 20 minutes. The reaction mixture was allowed to slowly return to r.t. and stirred for 5 h. The mixture was carefully diluted with brine/2M HCl and extracted with EtOAc and the organic layer washed with sat. brine before being dried (MgSO$_4$), filtered and evaporated under reduced pressure to give the product as a brown oil (3.90 g, 133%). $^1$H NMR (400 MHz, DMSO-d6, 30° C.) δ 1.08 (3H, t), 3.33 (1H, m), 3.47 (1H, m), 4.76 (1H, s), 7.13-7.44 (5H, m), 12.56 (1H, s).

Intermediate 19

(2S)-2-Methoxy-2-(4-methoxyphenyl)acetic acid

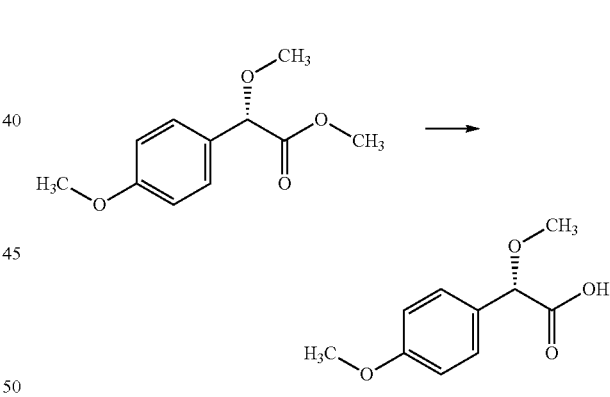

Into a 1000-mL 3-necked round-bottom flask purged and maintained with an inert atmosphere of nitrogen, was placed lithium hydroxide (17.3 g, 722.4 mmol), water (120 mL), MeOH (500 mL, 12.35 mol) and methyl (2S)-2-methoxy-2-(4-methoxyphenyl)acetate (Intermediate 20, 29 g, 137.95 mmol). The resulting solution was stirred for 2 h at 25° C. in an oil bath. The resulting mixture was concentrated under vacuum. The resulting residue was extracted with DCM (3×100 mL) and the organic layers combined. 2 Molar HCl was employed to adjust the mixture to pH=2. The resulting solution was extracted with DCM (5×100 mL) and the organic layers combined. After drying (MgSO$_4$) evaporation delivered (2S)-2-methoxy-2-(4-methoxyphenyl)acetic acid as a yellow solid (23 g, 85%). $^1$H NMR (300 MHz, CDCl$_3$, 26° C.) δ 3.39 (3H, s), 3.80 (3H, s), 4.73 (1H, s), 6.89-6.91 (2H, d), 7.32-7.35 (2H, d); m/z: ES$^-$ [M−H]$^-$ 195.

Intermediate 20

Methyl (2S)-2-methoxy-2-(4-methoxyphenyl)acetate

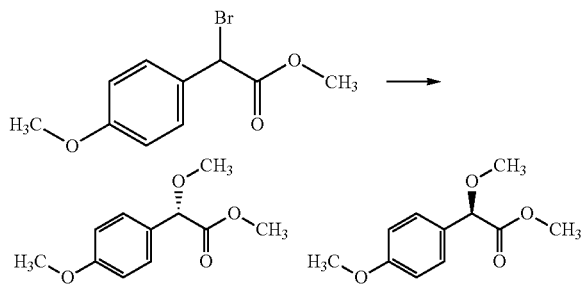

Into a 500-mL 3-necked round-bottom flask purged and maintained with an inert atmosphere of nitrogen, was placed MeOH (300 mL) and sodium metal (9.2 g, 400.18 mmol) portionwise. The solution was then refluxed for 30 minutes before being cooled to r.t. Methyl 2-bromo-2-(4-methoxyphenyl)acetate (Intermediate 21, 80 g, 308.76 mmol) was then added. The resulting solution was stirred for 1 h at 65° C. in an oil bath. The resulting mixture was concentrated under vacuum. The residue was purified by FCC eluting with EtOAc/petroleum ether (1:1). The racemic mixture was then separated by chiral HPLC with the following conditions: Column, CHIRALPAK IC; mobile phase, HEX:IPA (90:10), Detector, 254 nm. Flow rate 90 g/min. This resulted in methyl (2R)-2-methoxy-2-(4-methoxyphenyl)acetate as yellow oil (27 g, 83%), and methyl (2S)-2-methoxy-2-(4-methoxyphenyl)acetate as a yellow solid (23 g, 71%). $^1$H NMR (300 MHz, CDCl$_3$, 26° C.) δ 3.37-3.39 (3H, s), 3.71-3.73 (3H, s), 3.80 (3H, s), 4.72 (1H, s), 6.89 (2H, d), 7.35 (2H, d).

Intermediate 21

Methyl 2-bromo-2-(4-methoxyphenyl)acetate

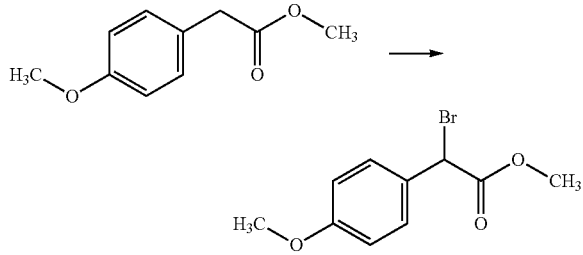

Into a 2-L 3-necked round-bottom flask purged and maintained with an inert atmosphere of nitrogen, was placed methyl 2-(4-methoxyphenyl)acetate (Intermediate 22, 210 g, 1.17 mol), AIBN (3 g, 18.27 mmol), NBS (208 g, 1.17 mol) and CCl$_4$ (1500 mL). The resulting solution was stirred for 6 h at 80° C. in an oil bath. The reaction mixture was cooled with a water/ice bath. The solids were filtered out. The resulting solution was extracted with DCM (4×150 mL) and the organic layers combined and concentrated under vacuum. This resulted in methyl 2-bromo-2-(4-methoxyphenyl)acetate as yellow oil (80 g, 26%). $^1$H NMR (300 MHz, CDCl$_3$, 26° C.) δ 3.79-3.82 (6H, s), 5.35 (1H, s), 6.84-6.90 (2H, d), 7.45-7.50 (2H, d).

Intermediate 22

Methyl 2-(4-methoxyphenyl)acetate

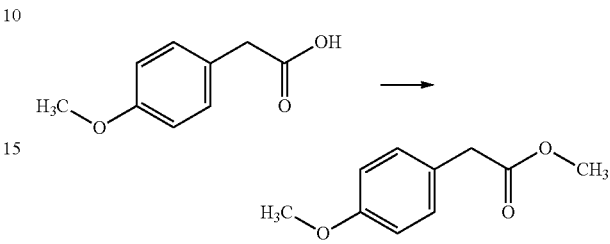

Into a 500-mL round-bottom flask, was placed 2-(4-methoxyphenyl)acetic acid (200 g, 1.20 mol), sulfuric acid (2 mL, 37.52 mmol) and MeOH (200 mL, 4.68 mol). The resulting solution was stirred for 2 h at 70° C. in an oil bath. The resulting mixture was concentrated under vacuum. The resulting solution was diluted with H$_2$O (200 mL). The pH value of the solution was adjusted to 7 with sodium bicarbonate (5 mol/L). The resulting solution was extracted with DCM (3×300 mL) and the organic layers combined, dried (MgSO$_4$) and evaporated under reduced pressure. This resulted in methyl 2-(4-methoxyphenyl)acetate as brown oil (210 g, 97%). $^1$H NMR (300 MHz, CDCl$_3$, 26° C.) δ 3.78-3.89 (6H, s), 5.35 (1H, s), 6.85-6.90 (2H, d), 7.45-7.50 (2H, s).

Intermediate 23

2-(4-Fluorophenyl)-2-methoxyacetic acid

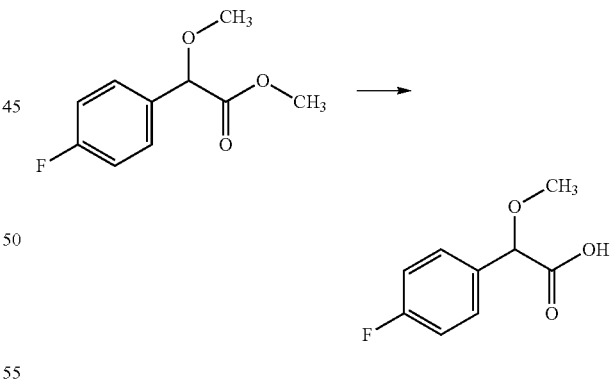

Methyl 2-(4-fluorophenyl)-2-methoxyacetate (Intermediate 24, 1.32 g, 6.66 mmol) was dissolved in MeOH (24 mL) and stirred at r.t. A solution of potassium hydroxide (0.45 g, 7.992 mmol) in MeOH (12 mL) was added, and the mixture stirred for 5 h. The mixture was evaporated under reduced pressure. The residue was partitioned between water and EtOAc (70 mL each). The aqueous was washed with EtOAc (70 mL) then acidified (to pH=2) with 2N hydrochloric acid. It was then extracted with EtOAc (2×100 mL). The combined acidic extracts were dried (MgSO$_4$) and evaporated under reduced pressure to afford 2-(4-fluorophenyl)-2-methoxy-acetic acid (1.16 g, 94%) as a colourless gum. $^1$H NMR (400 MHz, CDCl₃, 20° C.) δ 3.42 (3H, s), 4.77 (1H, s), 7.10-7.04 (2H, m), 7.44-7.40 (2H, m).

Intermediate 24

Methyl 2-(4-fluorophenyl)-2-methoxyacetate

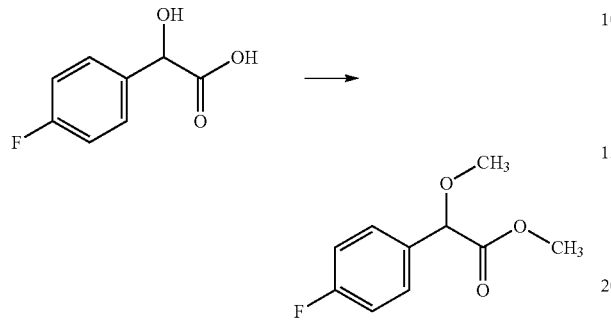

Cesium carbonate (7.64 g, 23.45 mmol) was dissolved in DMF (20 mL) at r.t. Iodomethane (2.4 mL, 38.55 mmol) was added, followed by 2-(4-fluorophenyl)-2-hydroxyacetic acid (2.0 g, 11.75 mmol), and the mixture stirred for 48 h at r.t. The DMF was evaporated under reduced pressure. The residue was partitioned between EtOAc and water (75 mL each). The organics were washed with water (75 mL), dried (MgSO₄), evaporated under reduced pressure and purified by FCC, eluent 3:1 cyclohexane:EtOAc. Pure fractions were evaporated to dryness to afford methyl 2-(4-fluorophenyl)-2-methoxyacetate (1.68 g, 72%) as a colourless oil. ¹H NMR (400 MHz, CDCl₃, 20° C.) δ 3.40 (3H, s), 3.72 (3H, s), 4.76 (1H, s), 7.09-7.03 (2H, m), 7.44-7.40 (2H, m).

Intermediate 25

2-Ethoxy-2-(4-fluorophenyl)acetic acid

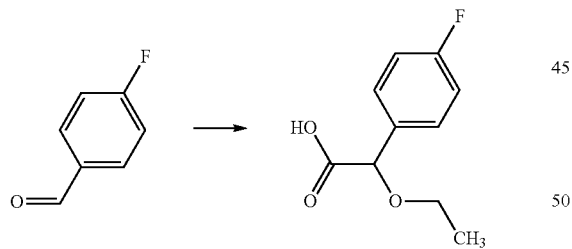

To a stirred mixture of 4-fluorobenzaldehyde (2.82 mL, 26.299 mmol) and bromoform (2.76 mL, 31.559 mmol) in EtOH (30 mL) at 0° C. was added, dropwise over 30 mins, a solution of potassium hydroxide (8.12 g, 144.645 mmol) in EtOH (60 mL). The mixture was stirred and warmed to r.t. overnight. The resulting precipitate was removed by filtration. The filtrate was evaporated to give a paste which was taken up in water (100 mL) and extracted with EtOAc (2×100 mL) to remove unreacted aldehyde. The aqueous phase was then acidified to pH=2 with 2N hydrochloric acid and extracted with EtOAc (2×100 mL). The combined organics were dried (MgSO₄), filtered and evaporated under reduced pressure to afford crude product. The crude product was further purified by FCC (3% MeOH in DCM) to give 2-ethoxy-2-(4-fluorophenyl)acetic acid (3.76 g, 72%) as a clear gum. ¹H NMR (400 MHz, DMSO, 30° C.) δ 1.14 (3H, t), 3.43-3.36 (2H, m, partly obscured by water peak), 4.87 (1H, s), 7.21-7.17 (2H, m), 7.45-7.41 (2H, m); m/z: ES⁻ [M−H]⁻ 197.

Intermediate 26

2-(4-Fluoro-3-methoxy-phenyl)-2-methoxy-acetic acid

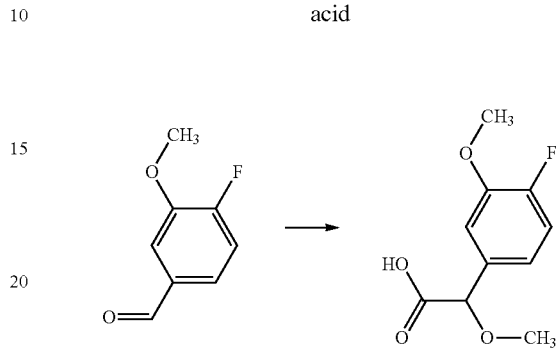

To a stirred mixture of 4-fluoro-3-methoxy-benzaldehyde (1.0 g, 6.488 mmol) and bromoform (0.68 mL, 7.785 mmol) in MeOH (10 mL) at 0° C. was added, dropwise over 1 h, a solution of potassium hydroxide (2.0 g, 35.682 mmol) in MeOH (20 mL). After addition the mixture was stirred and warmed to r.t. overnight. The resulting precipitate was removed by filtration. The filtrate was evaporated to give a paste which was taken up in water (100 mL) and extracted with EtOAc (2×100 mL). The aqueous phase was then acidified to pH=2 with 2N hydrochloric acid. It was extracted with EtOAc (2×100 mL). The combined organics were dried (MgSO₄), filtered and evaporated under reduced pressure to afford crude product. The crude product was further purified by FCC (elution gradient 0-5% MeOH in DCM) to give 2-(4-fluoro-3-methoxy-phenyl)-2-methoxy-acetic acid (0.66 g, 47%) as a colourless oil. ¹H NMR (400 mHz, CDCl₃, 30° C.) δ 3.43 (3H, s), 3.90 (3H, s), 4.75 (1H, s), 6.95-7.00 (1H, m), 7.10-7.04 (2H, m); m/z: ES⁻ [M−H]⁻ 213.

Intermediate 27

2-[3-(Difluoromethoxy)phenyl]-2-ethoxy-acetic acid

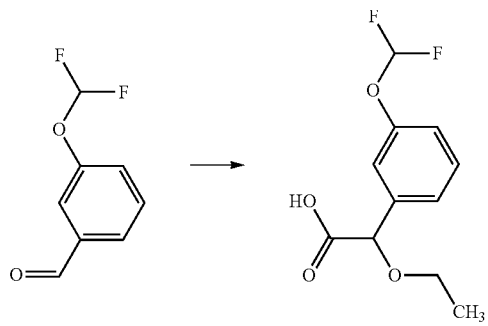 [SMILES: O=Cc1cccc(OC(F)F)c1 ; CCOC(C(=O)O)c1cccc(OC(F)F)c1]

To a stirred mixture of 3-(difluoromethoxy)benzaldehyde (2.0 g, 11.61 mmol) and bromoform (1.22 mL, 13.94 mmol) in EtOH (40 mL) at 0° C. was added, dropwise over a 1 h period, a solution of potassium hydroxide (3.59 g, 63.90 mmol) in EtOH (20 mL). After addition the mixture was left to stir and warmed to r.t. overnight. The precipitate that had formed was removed by filtration. The filtrate was evaporated to give a paste which was taken up in water (100 mL) and extracted with EtOAc (2×75 mL). The aqueous phase was then acidified to pH 1 with 2M HCl and extracted with EtOAc (2×75 mL). The combined organics were dried ($MgSO_4$), filtered, and evaporated to give a pale brown oil. This was purified by FCC (gradient elution 5% EtOAc+ 0.1% formic acid in cyclohexane to 20% EtOAc+0.1% formic acid in cyclohexane). Pure fractions were evaporated under reduced pressure to give 2-[3-(difluoromethoxy)phenyl]-2-ethoxy-acetic acid as a colourless oil (1.8 g, 62%). $^1$H NMR (400 MHz, $CDCl_3$, 21° C.) δ 1.29 (3H, t), 3.49-3.70 (2H, m), 4.89 (1H, s), 6.52 (1H, t), 7.07-7.15 (1H, m), 7.21-7.26 (1H, m), 7.28-7.35 (1H, m), 7.34-7.41 (1H, m). m/z: $ES^-$ $[M-H]^-$ 245.

Intermediate 28

2-Ethoxy-2-[3-(trifluoromethoxy)phenyl]acetic acid

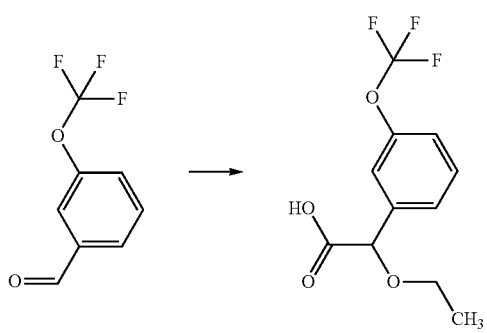 [SMILES: O=Cc1cccc(OC(F)(F)F)c1 ; CCOC(C(=O)O)c1cccc(OC(F)(F)F)c1]

To a stirred mixture of potassium hydroxide (1.62 g, 28.93 mmol) and bromoform (0.55 mL, 6.31 mmol) in EtOH (15 mL) at 0° C. was added, slowly over a 10 min period, a solution of 3-(trifluoromethoxy)benzaldehyde (0.75 mL, 5.26 mmol) in EtOH (30 mL). After addition the mixture was left to stir as it warmed to r.t. overnight. The precipitate was removed by filtration. The filtrate was evaporated to give a paste which was taken up in water (200 mL) and extracted with DCM (100 mL). This formed an emulsion, the aqueous phase was then acidified with 2M HCl (10 mL) and separated. It was then further extracted with EtOAc (100 mL). The combined organics were evaporated under reduced pressure and purified by FCC (elution gradient 0-50% EtOAc in cyclohexane). Pure fractions were combined and evaporated under reduced pressure to give 2-ethoxy-2-[3-(trifluoromethoxy)phenyl]acetic acid (690 mg, 49%). $^1$H NMR (400 MHz, DMSO-d6, 21° C.) δ 1.16 (3H, t), 3.38-3.50 (1H, m), 3.53-3.66 (1H, m), 4.99 (1H, s), 7.28-7.39 (2H, m), 7.45 (1H, d), 7.53 (1H, t), 13.04 (1H, s); m/z: $ES^+$ $[M+H]^+$ 265.

Biological Assays

The following assays were used to measure the effects of the compounds of the present invention: a) GLS Enzyme Potency Assay; b) GLS Cell Potency Assay; c) GLS Cell Proliferation Assay; and d) Mouse Xenograft Model. During the description of the assays, generally:
  i. The following abbreviations have been used: $CO_2$=Carbon dioxide; DMEM=Dulbecco's Modified Eagle Medium; DMSO=Dimethyl sulphoxide; EDTA=Ethylenediaminetetraacetic acid; EGTA=Ethylene glycol tetraacetic acid; FCS=Foetal calf serum; h=Hour(s); NBS=Non-binding surface; SDS=Sodium dodecyl sulphate; r.t.=room temperature; TRIS=Tris(Hydroxymethyl)aminomethane.
  ii. $IC_{50}$ values were calculated using a smart fitting model in Genedata. The $IC_{50}$ value was the concentration of test compound that inhibited 50% of biological activity. Where multiple repeat tests were carried out on a given Example, the result reported is the geometric mean.

Assay a): GLS Enzyme Potency Assay

A Glutamate Oxidase/AmplexRed coupled assay was used to measure the ability of compounds to bind to and inhibit the activity of GLS1 in vitro. 6His tagged GLS protein (amino acids 63-669) expressed in *E. Coli* was purified and stored at −80° C. in aliquots. GLS1 was diluted to 2× working concentration and incubated at r.t. to allow the tetrameric/dimeric forms to reach steady state. Assay measurements were performed in buffer comprising 50 mM TRIS pH 7.8, 100 mM $NaPO_4$, pH 7.8, 0.001% v/v Tween20. Purified recombinant GLS1 protein was diluted in assay buffer to 12 nM and pre-incubated at r.t. for 30 minutes. Test compounds were prepared by dilution in 100% DMSO to give the correct dose range for 12 point concentration response and an appropriate volume (2.5-60 nl) dispensed into 384 well micro assay plates (Greiner product code 784900) using a Labcyte Echo 555 acoustic dispenser. DMSO concentration was maintained at 2% by back filling with DMSO solution. 3 μL of diluted GLS1 protein (12 nM) was then dispensed into each well using a BioRaptr automated dispenser (Beckman-Coulter) and incubated for 15 minutes at r.t. 3 μL of 100 mM glutamine diluted in assay buffer was then added and the reaction incubated at r.t. for 60 minutes. The reaction was then stopped by addition of 45 μM 6-(2-bromoethynyl)-2,3-dimethyl-quinazolin-4-one, 75 μM Amplex Red, 0.375 units/mL Horseradish Peroxidase, 0.12 units/mL Glutamate Oxidase in 100 mM TRIS pH7.5. After 30 minutes at room temp in the dark, plates were read on a Perkin Elmer EnVision using 535/590 nm optic filters and raw data analysed using Genedata to generate $IC_{50}$ values. An artefact version of the assay where the 6His tagged GLS protein and glutamine were replaced with assay buffer was also used to rule out non specific effects on the assay components.

Assay b): GLS Cell Potency Assay

Compounds were assessed for their potential to inhibit cellular GLS activity by use of a PC3 coupled assay measuring cellular glutamate depletion. Test compounds were prepared by dilution in 100% DMSO to give the correct dose range for 12 point concentration response and an appropriate volume (5-120 nl) dispensed into 384 well micro assay plates (Corning product code 3712) using a Labcyte Echo 555 acoustic dispenser. DMSO concentration was maintained at 0.3% by back filling with DMSO solution. PC3 cells were grown in phenol free DMEM, 10% dialyzed FCS, 2 mM glutamine and following dispersal by trypsinisation were plated at 5.6×10$^3$ cells per well in 40 μl of growth medium directly into the 384 well assay plates containing dispensed compound. After incubation for 6 h at 37° C., 5% $CO_2$ growth media was aspirated and cells lysed in 15 μl of buffer containing 10 mM TRIS pH7.4, 100 mM NaCl, 1 mM EDTA, 1 mM EGTA, 1 mM NaF, 20 mM $Na_4P_2O_7$, 2 mM $Na_3VO_4$, 1% Triton X-100, 10% glycerol, 0.1% SDS and 0.5% deoxycholate. 4 μl Of cell lysate was then transferred to a 384 well NBS plate (Corning product code 3575) and 35 μl of 27.5 μM Amplex Red, 0.1375 U/mL Horseradish Peroxidase, 0.044 U/mL glutamate oxidase, 100 mM TRIS pH7.5 was added. After 30 minutes at room temp in the dark, plates were read on a Perkin Elmer EnVision using 535/590 nm optic filters and raw data analysed using proprietary software to generate $IC_{50}$ values.

Assay c): GLS Cell Proliferation Assay

The ability of compounds to inhibit cell growth was measured using a 384 well plate NCI-H1703 cell proliferation assay. NCI-H1703 cells were grown in phenol red free RPMI1640, 10% FCS and 2 mM glutamine and seeded at a density of 750 cells per well in 40 µl of growth medium into clear-bottom 384 well assay plates (Corning product code 3712) and incubated for 24 h at 37° C., 5% $CO_2$. Test compounds were prepared by dilution in 100% DMSO to give the correct dose range for 12 point concentration response and an appropriate volume (5-120 nl) dispensed directly into the assay plates containing plated cells. DMSO concentration was maintained at 0.3% by back filling with DMSO solution. Plates were incubated for 5 days at 37° C., 5% $CO_2$, Sytox Green and Saponin added to final concentration of 2 µM and 0.25% respectively and incubated for 6 h prior to analysis. Plates were read on an Acumen eX3 (TTP Labtech) using 488 nm excitation and FITC filter set (500-530 nm) for emission. $IC_{50}$ values were calculated by curve fitting to max inhibition of day zero growth using GeneData software analysis.

The potency of the Examples in assays a)-c) are shown in Table 2.

TABLE 2

Potency Data for the Examples in Assays a)-c)

| Example | Assay a) GLS Enzyme Potency Assay $IC_{50}$ (µM) | Assay b) GLS Cell Potency Assay $IC_{50}$ (µM) | Assay c) GLS Cell Proliferation Assay (µM) |
|---|---|---|---|
| 1(a) | 0.0628 | 0.0039 | 0.05351 |
| 1(b) | 1.6984 | 0.07 | 2.237 |
| 2(a) | 0.0213 | 0.00035 | 0.004851 |
| 2(b) | 0.1468 | 0.012 | 0.179 |
| 3 | 0.0290 | 0.00039 | 0.003237 |
| 4(a) | 0.0355 | 0.00151 | 0.005006 |
| 4(b) | 0.908 | 0.076 | 0.2622 |
| 5(a) | 0.0215 | 0.00019 | 0.003382 |
| 5(b) | 0.0879 | 0.0053 | 0.0535 |
| 6(a) | 0.0851 | 0.00257 | 0.01662 |
| 6(b) | 0.5187 | 0.037 | 0.08171 |
| 7(a) | 0.0148 | 0.00055 | 0.002235 |
| 7(b) | 0.0271 | 0.0038 | 0.006943 |
| 8(a) | 0.0306 | 0.0013 | 0.005038 |
| 8(b) | 0.2209 | 0.029 | 0.03675 |
| 9(a) | 0.0186 | 0.00014 | 0.000725 |
| 9(b) | 0.0329 | 0.0023 | 0.004396 |
| 10(a) | 0.0276 | 0.00091 | 0.01095 |
| 10(b) | 0.1102 | 0.013 | 0.2338 |
| 11 | 0.0310 | 0.0004006 | 0.01075 |
| 12(a) | 0.0220 | 0.0003474 | 0.01353 |
| 12(b) | 0.1023 | 0.02 | 0.4289 |
| 13(a) | 0.027 | 0.00096 | 0.01834 |
| 13(b) | 0.1697 | 0.014 | 0.5598 |
| 14(a) | 0.0255 | 0.00078 | 0.01507 |
| 14(b) | 0.1679 | 0.065 | 0.5185 |
| 15(a) | — | — | 0.0009208 |
| 15(b) | — | — | 0.002471 |
| 16(a) | — | — | 0.001324 |
| 16(b) | — | — | 0.006375 |
| 17(a) | 2.187 | 0.1751 | 3.566 |
| 17(b) | 0.09262 | 0.005954 | 0.1205 |
| 18(a) | 0.01531 | 0.000526 | 0.001875 |
| 18(b) | 0.1069 | 0.01116 | 0.07295 |
| 19(a) | 0.08513 | 0.00254 | 0.01662 |
| 19(b) | 0.5187 | 0.03736 | 0.08171 |
| 20(a) | 0.01619 | 0.000302 | 0.00194 |
| 20(b) | 0.1188 | 0.01041 | 0.1661 |
| 21(a) | 0.1621 | 0.01569 | 0.1684 |

TABLE 2-continued

Potency Data for the Examples in Assays a)-c)

| Example | Assay a) GLS Enzyme Potency Assay $IC_{50}$ (µM) | Assay b) GLS Cell Potency Assay $IC_{50}$ (µM) | Assay c) GLS Cell Proliferation Assay (µM) |
|---|---|---|---|
| 21(b) | 0.04691 | 0.00035 | 0.001776 |
| 22(a) | 0.07292 | 0.001504 | 0.01068 |
| 22(b) | 0.04336 | 0.000206 | 0.000729 |
| 23(a) | 0.02755 | 0.00032 | 0.004626 |
| 23(b) | 0.162 | 0.009014 | 0.03539 |
| 24 | 0.07468 | 0.004584 | 0.1183 |
| 25(a) | 0.03543 | 0.001807 | 0.06848 |
| 25(b) | 0.1354 | 0.05612 | 0.6298 |
| 26(a) | 2.268 | 0.221 | 2.048 |
| 26(b) | 0.08774 | 0.003374 | 0.1007 |
| 27(a) | 0.05082 | 0.002226 | 0.01168 |
| 27(b) | 0.844 | 0.01953 | 0.3369 |
| 28(a) | 0.03412 | 0.000711 | 0.009281 |
| 28(b) | 0.08477 | 0.01515 | 0.1506 |
| 29(a) | 0.1084 | 0.005425 | 0.1252 |
| 29(b) | 1.367 | 0.1345 | 1.962 |
| 30(a) | 0.09279 | 0.006738 | 0.0716 |
| 30(b) | 0.02096 | 0.000419 | 0.002009 |
| 31(a) | 0.05016 | 0.000559 | 0.01646 |
| 31(b) | 0.08615 | 0.03334 | 0.6241 |
| 32(a) | 2.461 | 0.3003 | 2.956 |
| 32(b) | 0.07069 | 0.00499 | 0.1069 |
| 33(a) | 0.05018 | 0.007128 | 0.1684 |
| 33(b) | 1.973 | 0.6899 | 5.538 |
| 34(a) | 0.08811 | 0.01204 | 0.09311 |
| 34(b) | 1.481 | 0.1685 | 2.898 |
| 35(a) | 1.946 | 0.3372 | 7.133 |
| 35(b) | 0.155 | 0.01873 | 0.4041 |

Assay d): Mouse Xenograft Model

Monotherapy

Female Harlan Nude mice were transplanted s.c. with human NSCLC NCI-H3122 cells to determine the in-vivo anti-tumour activity of GLS inhibitors. $5 \times 10^6$ cells in 50% matrigel (BD Bioscience) were injected s.c. on the left flank of the animals. Animals were randomised into groups of 10-15 when tumours reached a volume of ~200-300 mm³ and treatment commenced. Animals were dosed for 17 days 50 mg/kg once daily by peroral route with Example 2(a) as monotherapy. Tumours were measured twice weekly by calliper and volume of tumours calculated using elliptical formula (π/6×width×width×length). Statistical significance was evaluated using a one tailed, t-test. Example 2 was formulated in a 1% Polysorbate 80 and pH adjusted with 1M HCL to a final pH concentration of pH3.5. The results of testing Example 2(a) in the NCI-H3122 mouse xenograft model are shown in FIG. 2. Data is presented as mean tumour volume with calculated mean standard error bars. Treatment of NCI-H3122 xenograft with Example 2(a) monotherapy results in inhibition of growth in-vivo.

Combination Therapy

Male Scid mice were transplanted s.c. with human NSCLC NCI-H1703 cells (ATCC-CRL-5889) to determine the in-vivo anti-tumour activity of GLS inhibitors. $1 \times 10^7$ cells in 50% matrigel (BD Bioscience) were injected s.c. on the left flank of the animals.

Animals were randomised into groups of 10-12 when tumours reached a volume of ~200-300 mm³ and treatment commenced. Animals were dosed for 16 days 100 mg/kg once daily by peroral route with Example 2(a) as monotherapy or in combination with Taxotere®. In the Taxotere® dosed group animals were dosed once weekly by intravenous route where the Taxotere® was administered 1 hour post the peroral dose of Example 2(a). Tumours were measured twice weekly by calliper and volume of tumours calculated using elliptical formula (π/6×width×width×length). Statistical significance was evaluated using a one tailed, t-test. Taxotere® (Sanofi) was formulated in a physiological saline. Example 2 was formulated in a 1% Polysorbate 80 and pH adjusted with 1M HCL to a final pH concentration of pH3.5. The results of testing Example 2(a) in the NCI-H1703 mouse xenograft model are shown in FIG. 3. Data is presented as mean tumour volume with calculated mean standard error bars. Treatment of NCI-H1703 xenograft with Example 2(a) monotherapy results in inhibition of growth in-vivo. Treatment of NCI-H1703 xenograft with Example 2(a) dosed in combination with a once weekly schedule of Taxotere® results in slight regression compared to Taxotere® monotherapy treatment.

The invention claimed is:

1. A method for treating cancer mediated by GLS1 in a warm-blooded animal having said cancer, which comprises administering to said warm-blooded animal a therapeutically effective amount of a compound of Formula (I):

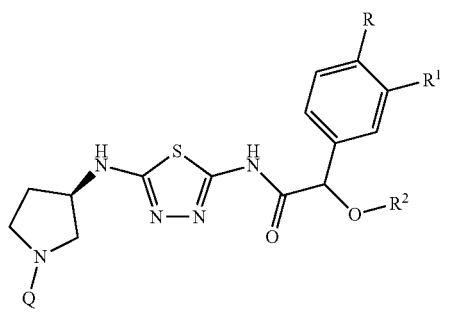

(I)

or a pharmaceutically acceptable salt thereof, where:
Q is pyridazin-3-yl, 1,2,4-triazin-3-yl or 1,2,4-triazin-6-yl;
R is hydro, fluoro or methoxy;
$R^1$ is hydro, methoxy, difluoromethoxy or trifluoromethoxy; and
$R^2$ is methyl or ethyl.

2. The method of claim 1, where Q is pyridazin-3-yl or 1,2,4-triazin-3-yl.

3. The method of claim 2, where Q is pyridazin-3-yl.

4. The method of claim 1, where R is hydro.

5. The method of claim 1, where $R^1$ is hydro.

6. The method of claim 1, where $R^1$ is methoxy, difluoromethoxy or trifluoromethoxy.

7. The method of claim 6, where $R^1$ is methoxy.

8. The method of claim 1, where $R^2$ is methyl.

9. The method of claim 1, where $R^2$ is ethyl.

10. The method of claim 1, where the compound is selected from the group consisting of:
(2S)-2-Methoxy-2-phenyl-N-[5-[[(3R)-1-(1,2,4-triazin-3-yl)pyrrolidin-3-yl]amino]-1,3,4-thiadiazol-2-yl]acetamide;
(2R)-2-Methoxy-2-phenyl-N-[5-[[(3R)-1-(1,2,4-triazin-3-yl)pyrrolidin-3-yl]amino]-1,3,4-thiadiazol-2-yl]acetamide;
(2S)-2-Methoxy-2-phenyl-N-[5-[[(3R)-1-pyridazin-3-ylpyrrolidin-3-yl]amino]-1,3,4-thiadiazol-2-yl]acetamide;
(2R)-2-Methoxy-2-phenyl-N-[5-[[(3R)-1-pyridazin-3-ylpyrrolidin-3-yl]amino]-1,3,4-thiadiazol-2-yl]acetamide;
(2S)-2-Methoxy-2-phenyl-N-[5-[[(3R)-1-(1,2,4-triazin-6-yl)pyrrolidin-3-yl]amino]-1,3,4-thiadiazol-2-yl]acetamide;
(2S)-2-Methoxy-2-(3-methoxyphenyl)-N-[5-[[(3R)-1-(1,2,4-triazin-3-yl)pyrrolidin-3-yl]amino]-1,3,4-thiadiazol-2-yl]acetamide;
(2R)-2-Methoxy-2-(3-methoxyphenyl)-N-[5-[[(3R)-1-(1,2,4-triazin-3-yl)pyrrolidin-3-yl]amino]-1,3,4-thiadiazol-2-yl]acetamide;
(2S)-2-Methoxy-2-(3-methoxyphenyl)-N-[5-[[(3R)-1-pyridazin-3-ylpyrrolidin-3-yl]amino]-1,3,4-thiadiazol-2-yl]acetamide;
(2R)-2-Methoxy-2-(3-methoxyphenyl)-N-[5-[[(3R)-1-pyridazin-3-ylpyrrolidin-3-yl]amino]-1,3,4-thiadiazol-2-yl]acetamide;
(2S)-2-[3-(Difluoromethoxy)phenyl]-2-methoxy-N-[5-[[(3R)-1-(1,2,4-triazin-3-yl)pyrrolidin-3-yl]amino]-1,3,4-thiadiazol-2-yl]acetamide;
(2R)-2-[3-(Difluoromethoxy)phenyl]-2-methoxy-N-[5-[[(3R)-1-(1,2,4-triazin-3-yl)pyrrolidin-3-yl]amino]-1,3,4-thiadiazol-2-yl]acetamide;
(2S)-2-[3-(Difluoromethoxy)phenyl]-2-methoxy-N-[5-[[(3R)-1-pyridazin-3-ylpyrrolidin-3-yl]amino]-1,3,4-thiadiazol-2-yl]acetamide;
(2R)-2-[3-(Difluoromethoxy)phenyl]-2-methoxy-N-[5-[[(3R)-1-pyridazin-3-ylpyrrolidin-3-yl]amino]-1,3,4-thiadiazol-2-yl]acetamide;
(2S)-2-Methoxy-N-[5-[[(3R)-1-(1,2,4-triazin-3-yl)pyrrolidin-3-yl]amino]-1,3,4-thiadiazol-2-yl]-2-[3-(trifluoromethoxy)phenyl]acetamide;
(2R)-2-Methoxy-N-[5-[[(3R)-1-(1,2,4-triazin-3-yl)pyrrolidin-3-yl]amino]-1,3,4-thiadiazol-2-yl]-2-[3-(trifluoromethoxy)phenyl]acetamide;
(2S)-2-Methoxy-N-[5-[[(3R)-1-pyridazin-3-ylpyrrolidin-3-yl]amino]-1,3,4-thiadiazol-2-yl]-2-[3-(trifluoromethoxy)phenyl]acetamide;
(2R)-2-Methoxy-N-[5-[[(3R)-1-pyridazin-3-ylpyrrolidin-3-yl]amino]-1,3,4-thiadiazol-2-yl]-2-[3-(trifluoromethoxy)phenyl]acetamide;
(2S)-2-Ethoxy-2-phenyl-N-[5-[[(3R)-1-pyridazin-3-ylpyrrolidin-3-yl]amino]-1,3,4-thiadiazol-2-yl]acetamide;
(2S)-2-Methoxy-2-(4-methoxyphenyl)-N-[5-[[(3R)-1-pyridazin-3-ylpyrrolidin-3-yl]amino]-1,3,4-thiadiazol-2-yl]acetamide;
(2R)-2-Ethoxy-2-phenyl-N-[5-[[(3R)-1-pyridazin-3-ylpyrrolidin-3-yl]amino]-1,3,4-thiadiazol-2-yl]acetamide;
(2S)-2-(4-Fluorophenyl)-2-methoxy-N-[5-[[(3R)-1-pyridazin-3-ylpyrrolidin-3-yl]amino]-1,3,4-thiadiazol-2-yl]acetamide;
(2R)-2-(4-Fluorophenyl)-2-methoxy-N-[5-[[(3R)-1-pyridazin-3-ylpyrrolidin-3-yl]amino]-1,3,4-thiadiazol-2-yl]acetamide;
(2S)-2-Ethoxy-2-(4-fluorophenyl)-N-[5-[[(3R)-1-pyridazin-3-ylpyrrolidin-3-yl]amino]-1,3,4-thiadiazol-2-yl]acetamide;
(2R)-2-Ethoxy-2-(4-fluorophenyl)-N-[5-[[(3R)-1-pyridazin-3-ylpyrrolidin-3-yl]amino]-1,3,4-thiadiazol-2-yl]acetamide;
(2S)-2-(4-Fluoro-3-methoxy-phenyl)-2-methoxy-N-[5-[[(3R)-1-pyridazin-3-ylpyrrolidin-3-yl]amino]-1,3,4-thiadiazol-2-yl]acetamide;
(2R)-2-(4-Fluoro-3-methoxy-phenyl)-2-methoxy-N-[5-[[(3R)-1-pyridazin-3-ylpyrrolidin-3-yl]amino]-1,3,4-thiadiazol-2-yl]acetamide;

(2S)-2-[3-(Difluoromethoxy)phenyl]-2-ethoxy-N-[5-[[(3R)-1-pyridazin-3-ylpyrrolidin-3-yl]amino]-1,3,4-thiadiazol-2-yl]acetamide;

(2R)-2-[3-(Difluoromethoxy)phenyl]-2-ethoxy-N-[5-[[(3R)-1-pyridazin-3-ylpyrrolidin-3-yl]amino]-1,3,4-thiadiazol-2-yl]acetamide;

(2S)-2-Ethoxy-N-[5-[[(3R)-1-pyridazin-3-ylpyrrolidin-3-yl]amino]-1,3,4-thiadiazol-2-yl]-2-[3-(trifluoromethoxy)phenyl]acetamide;

(2R)-2-Ethoxy-N-[5-[[(3R)-1-pyridazin-3-ylpyrrolidin-3-yl]amino]-1,3,4-thiadiazol-2-yl]-2-[3-(trifluoromethoxy)phenyl]acetamide;

(2S)-2-(4-Fluorophenyl)-2-methoxy-N-[5-[[(3R)-1-(1,2,4-triazin-3-yl)pyrrolidin-3-yl]amino]-1,3,4-thiadiazol-2-yl]acetamide;

(2R)-2-(4-Fluorophenyl)-2-methoxy-N-[5-[[(3R)-1-(1,2,4-triazin-3-yl)pyrrolidin-3-yl]amino]-1,3,4-thiadiazol-2-yl]acetamide;

(2S)-2-Phenyl-N-[5-[[(3R)-1-pyridazin-3-ylpyrrolidin-3-yl]amino]-1,3,4-thiadiazol-2-yl]-2-(trideuteriomethoxy)acetamide;

(2R)-2-Phenyl-N-[5-[[(3R)-1-pyridazin-3-ylpyrrolidin-3-yl]amino]-1,3,4-thiadiazol-2-yl]-2-(trideuteriomethoxy)acetamide;

(2S)-2-[3-(Difluoromethoxy)phenyl]-2-methoxy-N-[5-[[(3R)-1-(1,2,4-triazin-3-yl)pyrrolidin-3-yl]amino]-1,3,4-thiadiazol-2-yl]acetamide;

(2R)-2-[3-(Difluoromethoxy)phenyl]-2-methoxy-N-[5-[[(3R)-1-(1,2,4-triazin-3-yl)pyrrolidin-3-yl]amino]-1,3,4-thiadiazol-2-yl]acetamide;

(2S)-2-Deuterio-2-phenyl-N-[5-[[(3R)-1-pyridazin-3-ylpyrrolidin-3-yl]amino]-1,3,4-thiadiazol-2-yl]-2-(trideuteriomethoxy)acetamide;

(2R)-2-Deuterio-2-phenyl-N-[5-[[(3R)-1-pyridazin-3-ylpyrrolidin-3-yl]amino]-1,3,4-thiadiazol-2-yl]-2-(trideuteriomethoxy)acetamide;

(2S)-2-Methoxy-2-(3-methoxyphenyl)-N-[5-[[(3R)-1-(1,2,4-triazin-6-yl)pyrrolidin-3-yl]amino]-1,3,4-thiadiazol-2-yl]acetamide;

(2R)-2-Methoxy-2-(3-methoxyphenyl)-N-[5-[[(3R)-1-(1,2,4-triazin-6-yl)pyrrolidin-3-yl]amino]-1,3,4-thiadiazol-2-yl]acetamide;

(2S)-2-Methoxy-N-[5-[[(3R)-1-(1,2,4-triazin-6-yl)pyrrolidin-3-yl]amino]-1,3,4-thiadiazol-2-yl]-2-[3-(trifluoromethoxy)phenyl]acetamide;

(2R)-2-Methoxy-N-[5-[[(3R)-1-(1,2,4-triazin-6-yl)pyrrolidin-3-yl]amino]-1,3,4-thiadiazol-2-yl]-2-[3-(trifluoromethoxy)phenyl]acetamide;

(2S)-2-[3-(Difluoromethoxy)phenyl]-2-methoxy-N-[5-[[(3R)-1-(1,2,4-triazin-6-yl)pyrrolidin-3-yl]amino]-1,3,4-thiadiazol-2-yl]acetamide;

(2R)-2-[3-(Difluoromethoxy)phenyl]-2-methoxy-N-[5-[[(3R)-1-(1,2,4-triazin-6-yl)pyrrolidin-3-yl]amino]-1,3,4-thiadiazol-2-yl]acetamide;

(2S)-2-Methoxy-2-(4-methoxyphenyl)-N-[5-[[(3R)-1-(1,2,4-triazin-3-yl)pyrrolidin-3-yl]amino]-1,3,4-thiadiazol-2-yl]acetamide;

(2S)-2-(3,4-Dimethoxyphenyl)-2-methoxy-N-[5-[[(3R)-1-pyridazin-3-ylpyrrolidin-3-yl]amino]-1,3,4-thiadiazol-2-yl]acetamide;

(2R)-2-(3,4-Dimethoxyphenyl)-2-methoxy-N-[5-[[(3R)-1-pyridazin-3-ylpyrrolidin-3-yl]amino]-1,3,4-thiadiazol-2-yl]acetamide;

(2S)-2-(3,4-Dimethoxyphenyl)-2-methoxy-N-[5-[[(3R)-1-(1,2,4-triazin-3-yl)pyrrolidin-3-yl]amino]-1,3,4-thiadiazol-2-yl]acetamide;

(2R)-2-(3,4-Dimethoxyphenyl)-2-methoxy-N-[5-[[(3R)-1-(1,2,4-triazin-3-yl)pyrrolidin-3-yl]amino]-1,3,4-thiadiazol-2-yl]acetamide;

(2S)-2-Ethoxy-2-(3-methoxyphenyl)-N-[5-[[(3R)-1-(1,2,4-triazin-3-yl)pyrrolidin-3-yl]amino]-1,3,4-thiadiazol-2-yl]acetamide;

(2R)-2-Ethoxy-2-(3-methoxyphenyl)-N-[5-[[(3R)-1-(1,2,4-triazin-3-yl)pyrrolidin-3-yl]amino]-1,3,4-thiadiazol-2-yl]acetamide;

(2S)-2-Ethoxy-2-(4-methoxyphenyl)-N-[5-[[(3R)-1-pyridazin-3-ylpyrrolidin-3-yl]amino]-1,3,4-thiadiazol-2-yl]acetamide;

(2R)-2-Ethoxy-2-(4-methoxyphenyl)-N-[5-[[(3R)-1-pyridazin-3-ylpyrrolidin-3-yl]amino]-1,3,4-thiadiazol-2-yl]acetamide;

(2S)-2-Ethoxy-2-(4-methoxyphenyl)-N-[5-[[(3R)-1-(1,2,4-triazin-3-yl)pyrrolidin-3-yl]amino]-1,3,4-thiadiazol-2-yl]acetamide;

(2R)-2-Ethoxy-2-(4-methoxyphenyl)-N-[5-[[(3R)-1-(1,2,4-triazin-3-yl)pyrrolidin-3-yl]amino]-1,3,4-thiadiazol-2-yl]acetamide;

(2S)-2-Ethoxy-2-(3-methoxyphenyl)-N-[5-[[(3R)-1-pyridazin-3-ylpyrrolidin-3-yl]amino]-1,3,4-thiadiazol-2-yl]acetamide;

(2R)-2-Ethoxy-2-(3-methoxyphenyl)-N-[5-[[(3R)-1-pyridazin-3-ylpyrrolidin-3-yl]amino]-1,3,4-thiadiazol-2-yl]acetamide;

(2S)-2-Ethoxy-2-(4-fluoro-3-methoxy-phenyl)-N-[5-[[(3R)-1-pyridazin-3-ylpyrrolidin-3-yl]amino]-1,3,4-thiadiazol-2-yl]acetamide;

(2R)-2-Ethoxy-2-(4-fluoro-3-methoxy-phenyl)-N-[5-[[(3R)-1-pyridazin-3-ylpyrrolidin-3-yl]amino]-1,3,4-thiadiazol-2-yl]acetamide;

(2S)-2-(4-Fluoro-3-methoxy-phenyl)-2-methoxy-N-[5-[[(3R)-1-(1,2,4-triazin-3-yl)pyrrolidin-3-yl]amino]-1,3,4-thiadiazol-2-yl]acetamide;

(2R)-2-(4-Fluoro-3-methoxy-phenyl)-2-methoxy-N-[5-[[(3R)-1-(1,2,4-triazin-3-yl)pyrrolidin-3-yl]amino]-1,3,4-thiadiazol-2-yl]acetamide;

(2S)-2-Ethoxy-2-(4-fluoro-3-methoxy-phenyl)-N-[5-[[(3R)-1-(1,2,4-triazin-3-yl)pyrrolidin-3-yl]amino]-1,3,4-thiadiazol-2-yl]acetamide;

(2R)-2-Ethoxy-2-(4-fluoro-3-methoxy-phenyl)-N-[5-[[(3R)-1-(1,2,4-triazin-3-yl)pyrrolidin-3-yl]amino]-1,3,4-thiadiazol-2-yl]acetamide;

(2S)-2-Ethoxy-2-phenyl-N-[5-[[(3R)-1-(1,2,4-triazin-3-yl)pyrrolidin-3-yl]amino]-1,3,4-thiadiazol-2-yl]acetamide;

(2R)-2-Ethoxy-2-phenyl-N-[5-[[(3R)-1-(1,2,4-triazin-3-yl)pyrrolidin-3-yl]amino]-1,3,4-thiadiazol-2-yl]acetamide;

(2S)-2-Ethoxy-2-(4-fluorophenyl)-N-[5-[[(3R)-1-(1,2,4-triazin-3-yl)pyrrolidin-3-yl]amino]-1,3,4-thiadiazol-2-yl]acetamide; and (2R)-2-Ethoxy-2-(4-fluorophenyl)-N-[5-[[(3R)-1-(1,2,4-triazin-3-yl)pyrrolidin-3-yl]amino]-1,3,4-thiadiazol-2-yl]acetamide.

11. A method for treating cancer mediated by GLS1 in a warm-blooded animal having said cancer, which comprises administering to said warm-blooded animal a therapeutically effective amount of (2S)-2-methoxy-2-phenyl-N-[5-[[(3R)-1-pyridazin-3-ylpyrrolidin-3-yl]amino]-1,3,4-thiadiazol-2-yl]acetamide.

* * * * *